(12) United States Patent
Mousseau et al.

(10) Patent No.: US 12,217,844 B2
(45) Date of Patent: Feb. 4, 2025

(54) SYSTEMS, DEVICES AND METHODS FOR DETECTING AND TRACKING DRUG EXTRACTION

(71) Applicant: 3D BRIDGE SOLUTIONS INC., Vancouver (CA)

(72) Inventors: Gary Mousseau, Waterloo (CA); Karima Bawa, Vancouver (CA)

(73) Assignee: 3D Bridge Solutions Inc., Vancouver (CA)

(*) Notice: Subject to any disclaimer, the term of this patent is extended or adjusted under 35 U.S.C. 154(b) by 157 days.

(21) Appl. No.: 17/743,299

(22) Filed: May 12, 2022

(65) Prior Publication Data

US 2022/0367022 A1    Nov. 17, 2022

Related U.S. Application Data

(60) Provisional application No. 63/187,776, filed on May 12, 2021.

(51) Int. Cl.
*G16H 20/10*    (2018.01)

(52) U.S. Cl.
CPC .................. *G16H 20/10* (2018.01)

(58) Field of Classification Search
None
See application file for complete search history.

(56) References Cited

U.S. PATENT DOCUMENTS

2020/0024047 A1*  1/2020  McNannay .......... B65D 75/367
2021/0038478 A1*  2/2021  Mohamed Elmahdy ....................
                                                    G16H 20/13

* cited by examiner

*Primary Examiner* — Devin C Hein
(74) *Attorney, Agent, or Firm* — Norton Rose Fulbright Canada LLP; Maya Medeiros

(57) ABSTRACT

Methods and systems for detecting and tracking drug extraction from one or more drug storage apparatus at a central server. The system involves one or more authenticated drug storage apparatus and the central server. An access detection computer circuit integrates with packaged drugs, creating detectable drug packaging. The access detection computer circuit provides drug access detection trigger signals when drugs are accessed from the detectable drug packaging. There is a communication device for transmitting secure communication messages between the components.

20 Claims, 19 Drawing Sheets

SYSTEMS, DEVICES AND METHODS FOR DETECTING AND TRACKING DRUG EXTRACTION

FIELD

Embodiments relate to systems and methods for detecting and tracking drug extraction activity from one or more drug containment apparatuses at a central server. In particular, embodiments relate to systems and methods for authenticating one or more drug containment apparatuses within the central server and subsequently detecting and tracking drug extraction activity from packaged drugs by drug consumers.

INTRODUCTION

Drugs can be packaged or re-packaged into containment apparatuses (in many places and in many ways) to help regulate dosing and/or prevent diversion of the drugs. There exists a need for methods that detect removal of any of the drugs contained within the containment apparatus. The containment apparatus provides protection of the drugs. A dosing regimen can be established for a drug consumer to assist them in adhering to drug consumption information and prevent diversion.

There exists a need to help support prescription drug users for medication consumption and improve adherence to a dosing regimen and prevent diversion, or at least alternative solutions.

SUMMARY

In an aspect, embodiments described herein provide a system for detecting and tracking drug extraction from one or more drug storage apparatus at a central server. The system has one or more authenticated drug storage apparatus having at least one access detection computer circuit that integrates with drug packaging containing one or more medication storage areas, the access detection computer circuit providing drug access detection trigger signals. The drug storage apparatus has a storage unit that couples to the access detection computer circuit, and has a hardware processor that receives control commands. The drug storage apparatus has a communication device for transmitting secure communication data messages, the access detection trigger signals, and an authentication request containing a device-identity value for receiving one or more confirmation messages from a central server for verification of the authenticated drug storage apparatus and verification of assignment of the drug storage apparatus, wherein the communication device relays the one or more confirmation messages to the hardware processor. The drug storage apparatus has an user-identity input device having an identity input circuit to cause a secure user-identity captured message to be sent by the communication device to the central server confirming that a drug consumer's identity is stored in a drug storage apparatus memory to create an authorized drug consumer record for granting access permission. The system has a device with a user interface for selecting an authenticated and unassigned drug storage apparatus and defining authorized drug monitoring entities and drug regimen parameters to establish a drug consumption regimen for a drug consumer by generating regimen encoded files with instructions for specific access periods for the authorized drug storage apparatus.

The system has a central server having: a non-transitory memory storing a database of device-identity values for storage units for verifying the authentication request with the device-identity value for the storage unit and generating confirmation messages for the verification of the authenticated drug storage apparatus. There is a communication device that receives the authentication request, the identity captured message and the drug access detection trigger signals from the communication device for identified access attempts; transmits the authentication confirmation messages for the verification of the authenticated drug storage apparatus; transmitting the assignment confirmation message to provide the identification of an assigned drug consumer for identity capture; transmitting the drug regimen encoded files securely to the communication device to provide the instructions for the specific access periods for the authenticated drug storage apparatus; transmits a commence dosing message to trigger the start of drug dosing operation when both the drug regimen encoded files are downloaded and when the identity captured message is received related to the authorized drug consumer assigned to the authenticated drug storage apparatus; and receives the drug access detection trigger signals from the communication computer for identified access attempts. The central server has a hardware processor that: relays the drug consumption information and alarm messages onto the defined authorized drug monitoring entities.

In some embodiments, the system has a plurality of access detection computer circuits corresponding to a plurality of medication storage areas of the detectable drug packaging, each of the storage medication areas having a corresponding access detection computer circuit.

In some embodiments, the system disables an access detection computer circuit for the corresponding storage medication area.

In some embodiments, a user action to access the storage medication area disables access detection computer circuit for the corresponding storage medication area.

In some embodiments, the central server having the hardware processor receives the drug access detection signals from the communication device and computes drug adherence and drug consumption metrics by processing the drug access detection trigger signals in relation to the drug regimen parameters for one or more authenticated drug storage apparatus.

In some embodiments, the central server having the hardware processor receives and processes activity messages from the known storage unit's identity with severity indicators that are used to select alarm messages.

In some embodiments, the system has a main access detection computer circuit having an overall unique identity, and a plurality of access detection computer circuits corresponding to a plurality of individual medication storage areas of the detectable drug packaging.

In some embodiments, the storage unit has a lock to enable a closed locked position and an open unlocked position, wherein the control commands trigger the lock to enable the unlocked open position in response to an assignment confirmation message, the storage unit in the open unlocked position capable of containing the detectable drug packaging, the lock further triggering to the closed locked position by detecting the detectable drug packaging in the storage unit, the lock further resists and detects unauthorized access attempts using user-identity input.

In some embodiments, the storage unit has a device-identity known to the central server.

In some embodiments, the user interface further requires the authorized drug manager to enter a verification code of the authenticated storage apparatus before being allowed to assign the authenticated drug storage apparatus to a drug consumer.

In some embodiments, the drug regimen parameters are provided from an external system and exchanged with the central server.

In some embodiments, drug adherence and drug consumption information is further relayed onto external systems over a secure link for further analysis and presentation.

In some embodiments, the drug storage apparatus sends a message to trigger a secondary event; wherein the secondary event may be one or more of making an emergency call, and triggering a secondary drug storage apparatus to begin operation.

In some embodiments, the user interface receives input for a number of drugs for the drug packaging and the central servers sends the input.

In some embodiments, the access detection computer circuit further sends a secure communication message to the central server indicating a type and quantity of drugs for the drug packaging.

In some embodiments, the drug monitoring entities comprise a drug consumer computer.

In some embodiments, the system has a logging system that collects historical information from the drug monitoring entities to create statistical models around drug adherence by drug consumers.

In some embodiments, the authenticated drug storage unit unlock mechanism can be triggered when the packaged drugs inside the authenticated drug storage unit are exhausted.

In another aspect, there is provided a central server for detecting and tracking drug extraction from a plurality of drug storage apparatuses, each drug storage apparatus integrating packaged drugs and an access detection device for transmitting drug access detection trigger signals when drugs are accessed from packaging.

The central server has a user interface for receiving a verification code for an authorized drug storage apparatus and input defining drug regimen parameters to establish a drug consumption regimen for a drug consumer by generating regimen encoded files with instructions for specific access periods when drugs can be accessed from the authorized drug storage apparatus. The system has non-transitory memory storing a database of identity values for drug storage apparatuses for verifying the authentication request with the identity value for the drug storage apparatus and generating confirmation messages for the verification of the drug storage apparatus.

The system has a communication interface for: transmitting the confirmation messages for the verification of the drug storage apparatus; transmitting the drug regimen encoded files securely to the communication device to provide the instructions for the specific access periods when the packaged drugs can be accessed by an authorized drug consumer from the authenticated drug storage apparatus; transmitting a commence dosing message to trigger the start of drug dosing operation when both the drug regimen encoded files are downloaded and when the identity captured message is received related to drugs held by the authenticated drug storage apparatus; receiving the drug access detection trigger signals from the communication device for identified attempts to access the drugs within the packaging; and a hardware processor that uses statistical analysis to compute drug consumption information using the access signals and the dosing regimen information and relays the drug consumption information onto the defined authorized drug monitoring entities.

In another aspect, there is provided a method for detecting and tracking drug extraction from a plurality of drug storage apparatuses. The method involves: at one or more authenticated drug storage apparatus, providing drug access detection trigger signals using an access detection computer circuit that integrates with packaged drugs when drugs are accessed from detectable drug packaging; sending control commands to a hardware processor of a storage unit that couples to the access detection computer circuit; transmitting, by a communication device, secure communication data messages, the access detection trigger signals, and an authentication request containing a device-identity value for receiving one or more confirmation messages from a central server for verification of the authenticated drug storage apparatus and verification of assignment of the drug storage apparatus; relaying, by the communication device, the one or more confirmation messages to the hardware processor; sending a secure user-identity captured message by an identity input circuit and the communication device to the central server confirming that a drug consumer's identity is stored in a drug storage apparatus memory to create an authorized drug consumer record for granting access permission; selecting an authenticated and unassigned drug storage apparatus and defining authorized drug monitoring entities and drug regimen parameters at a user interface of the central server to establish a drug consumption regimen for a drug consumer by generating regimen encoded files with instructions for specific access periods when drugs can be accessed from the authorized drug storage apparatus; storing a database of device-identity values at storage units of non-transitory memory for verifying the authentication request with the device-identity value for the storage unit and generating confirmation messages for the verification of the authenticated drug storage apparatus; receiving, at a communication interface, the authentication request, the identity captured message and the drug access detection trigger signals from the communication device for identified access attempts; transmitting the authentication confirmation messages for the verification of the authenticated drug storage apparatus; transmitting the assignment confirmation message; transmitting the drug regimen encoded files securely to the communication device to provide the instructions for the specific access periods for an authorized consumer from the authenticated drug storage apparatus; transmitting a commence dosing message to trigger the start of drug dosing operation when both the drug regimen encoded files are downloaded and when the identity captured message is received related to the authorized drug consumer assigned to the authenticated drug storage apparatus; receiving the drug access detection trigger signals from the communication computer for identified access attempts; computing, at a hardware processor, drug adherence and drug consumption metrics by processing the drug access detection trigger signals in relation to the drug regimen parameters for one or more authenticated drug storage apparatus; receiving and processing activity messages from the known storage unit's identity with severity indicators that are used to select alarm messages; and relaying the drug consumption information and alarm messages onto the defined authorized drug monitoring entities.

In some embodiments, the storage unit has a lock to enable a closed locked position and an open unlocked position to trigger the lock to enable the unlocked open position in response to an assignment confirmation message, the storage unit in the open unlocked position capable of containing the detectable drug packaging, the lock further triggering to the closed locked position by detecting presence of the detectable drug packaging in the storage unit, the lock further resists and detects unauthorized access attempts using user-identity input.

In another aspect, there is provided a system for detecting and tracking drug extraction from one or more drug storage apparatus at a central server. The system has one or more authenticated drug storage apparatus having: an access detection computer circuit that integrates with drug packaging containing one or more medication storage areas, the access detection computer circuit providing drug access detection trigger signals. The system has a storage unit that couples to the access detection computer circuit and has a hardware processor that receives control commands. The system has a communication device for transmitting secure communication data messages, the access detection trigger signals, and an authentication request containing an identity value for receiving confirmation messages from a central server for verification of the authenticated drug storage apparatus. The system has an identity input device having an identity input circuit to cause a secure identity captured message to be sent by the communication computer to the central server confirming that a drug consumer's identity is stored in memory to create an authorized drug consumer record for granting access permission.

The system has a central server having: a user interface for receiving a drug storage apparatus verification code and input defining authorized drug monitoring entities and drug regimen parameters to establish a drug consumption regimen for a drug consumer by generating regimen encoded files with instructions for specific access periods when drugs can be accessed from the authorized drug storage apparatus; non-transitory memory storing a database of device-identity values for drug storage apparatuses for verifying the authentication request with the device-identity value for the drug storage apparatus and generating confirmation messages for the verification of the authenticated drug storage apparatus. The system has a communication interface for: transmitting the confirmation messages for the verification of the authenticated drug storage apparatus; transmitting the drug regimen encoded files securely to the communication computer to provide the instructions for the specific access periods for the authenticated drug storage apparatus; transmitting dosing messages to trigger the start of drug dosing operation when both the drug regimen encoded files are downloaded and when the identity captured message is received for the authenticated drug storage apparatus; receiving the drug access detection trigger signals from the communication computer for identified access attempts. The system has a hardware processor that computes drug consumption information using the access signals and relays the drug consumption information onto the defined authorized drug monitoring entities.

In some embodiments, the user interface receives input for a number of drugs for the drug packaging and the central servers sends the input.

In some embodiments, the access detection computer circuit further sends a secure communication message to the central server indicating type and quantity of drugs.

In some embodiments, the drug monitoring entities comprise a drug consumer computer.

In some embodiments, the system has a logging system that collects historical information from the drug monitoring entities to create statistical models around drug adherence by drug consumers.

In some embodiments, the system has an unlock device that triggers when the central server sends a confirmation message indicating verification of the authenticated drug storage apparatus; a locking device that triggers by the access detection computer circuit; wherein the unlock device can be triggered when the packaged drugs inside the authenticated drug storage unit are exhausted.

In another aspect, there is provided a central server for detecting and tracking drug extraction from a plurality of drug storage apparatuses, each drug storage apparatus integrating drug packaging and an access detection device for transmitting drug access detection trigger signals. The central server has a user interface for inputting defining drug regimen parameters to establish a drug consumption regimen for a drug consumer by generating regimen encoded files with instructions for specific access periods when drugs can be accessed from the authorized drug storage apparatus. The server has non-transitory memory storing a database of device-identity values for drug storage apparatuses for verifying the authentication request with the device-identity value for the drug storage apparatus and generating confirmation messages for the verification of the drug storage apparatus. The server has a communication interface for: transmitting the confirmation messages for the verification of the drug storage apparatus; transmitting the drug regimen encoded files securely to the communication computer to provide the instructions for the specific access periods when the packaged drugs can be accessed by an authorized drug consumer from the authenticated drug storage apparatus; transmitting dosing messages to trigger the start of drug dosing operation when both the drug regimen encoded files are downloaded and when the identity captured message is received related to drugs held by the authenticated drug storage apparatus; receiving the drug access detection trigger signals from the communication computer for identified access attempts. The server has a hardware processor that computes drug consumption information using the access signals and relays the drug consumption information onto the defined authorized drug monitoring entities.

In some embodiments, the central server further saves and aggregates all drug access attempts historic access attempts to show statistical information related to drug consumption adherence.

In some embodiments, the access detection computer circuit is a low-frequency radio frequency identification (RFID) computer circuit.

In some embodiments, the access detection computer circuit is a paper-based computer circuit capable of carrying an electrical signal.

In some embodiments, the secure drug storage unit and the drug consumer computer are contained within the same physical housing.

In some embodiments, the drug consumer computer is a cell phone.

In some embodiments, the relay of drug consumption information can include alarms when the drug access regimen is violated.

In some embodiments, the server has a plurality of access detection computer circuits and a corresponding plurality of secure drug storage units, wherein the central server receives access signals generated by the plurality of access detection computer circuits.

In another aspect, there is provided a method for detecting and tracking drug extraction from a plurality of drug storage apparatuses. The method has: at one or more authenticated drug storage apparatuses, providing drug access detection trigger signals using an access detection computer circuit that integrates with drug packaging to create detectable drug packaging; sending control commands using a hardware processor of a storage unit to trigger an assigned mode in response to an assignment confirmation message, the storage unit coupling to the detectable drug packaging, the assignment further detecting the presence of individual drug packaging compartments correlated to the detectable drug packaging; transmitting, by a communication device, secure communication data messages, the access detection trigger signals, and an authentication request containing a device-identity value for receiving one or more confirmation messages from a central server for verification of the authenticated drug storage unit and verification of assignment of the drug storage unit; relaying, by the communication device, the one or more confirmation messages to the hardware processor; sending a secure user-identity captured message by an identity input circuit and the communication device to the central server confirming that a drug consumer's identity is stored in a drug storage apparatus memory to create an authorized drug consumer record for confirming access to loaded drugs in the storage unit; selecting an authenticated and unassigned drug storage unit and defining authorized drug monitoring entities and drug regimen parameters at a user interface of the central server to establish a drug consumption regimen for a drug consumer by generating regimen encoded files with instructions for specific access periods when drugs can be accessed from the authorized drug storage unit; storing a database of device-identity values at storage units of non-transitory memory for verifying the authentication request with the device-identity value for the storage unit and generating confirmation messages for the verification of the authenticated drug storage apparatus; receiving, at a communication interface, the authentication request, the identity captured message and the drug access detection trigger signals from the communication device for identified attempts to access the drugs within the storage unit; transmitting the authentication confirmation messages for the verification of the authenticated drug storage unit; transmitting the assignment confirmation message to trigger the assignment of the storage unit; transmitting the drug regimen encoded files securely to the communication device to provide the instructions for the specific access periods when the packaged drugs should be accessed by an authorized drug consumer from the authenticated drug storage unit; transmitting a commence dosing message to trigger the start of drug dosing operation when both the drug regimen encoded files are downloaded and when the identity captured message is received related to the authorized drug consumer assigned to the authenticated drug storage unit; receiving the drug access detection trigger signals from the communication computer for identified attempts to access the drugs within the storage unit; computing, at a hardware processor, drug adherence and drug consumption data by processing the drug access detection trigger signals in relation to the drug regimen parameters for one or more authenticated drug storage apparatus; receiving and processing activity messages from the known storage unit's identity with severity indicators that are used to select alarm messages; and relaying the drug consumption data and alarm messages onto the defined authorized drug monitoring entities.

In another aspect, there is provided a system for detecting and tracking drug extractions at one or more drug storage apparatus. The system has: a central server having a hardware processor and memory storing drug consumption data. The system has a drug storage apparatus having: a storage unit that couples to an access detection computer circuit that integrates with drug packaging containing one or more medication storage areas, the storage unit containing a device-identity known to the central server. The central server authorizes the drug storage apparatus using the storage unit device-identity. The authorized drug storage apparatus communicates with the central server and exchanges authorization and configuration parameters. The hardware processor has a user interface for defining drug regimen parameters to establish a drug consumption regimen for a drug consumer by generating non-transitory computer readable media storing regimen encoded files with instructions for specific access periods when drugs can be accessed from the authorized drug storage apparatus. The system has a communication interface for the drug storage apparatus and the central server. The communication interface: transmits the confirmation messages for the authorization of the drug storage apparatus; securely transmits the drug regimen encoded files to the authorized drug storage apparatus with instructions for the specific access periods when the packaged drugs can be accessed by an authorized drug consumer from the authenticated drug storage apparatus; transmits a commence dosing message to trigger the start of drug dosing operation when both the drug regimen encoded files are downloaded and when the identity captured message is received related to drugs held by the authenticated drug storage apparatus; receives the drug access detection trigger signals for identified attempts to access the drugs within the packaging. The hardware processor in the central server computes and updates the drug consumption data stored in the memory using the access signals and the dosing regimen information and relays the drug consumption information onto the defined authorized drug monitoring entities.

In some embodiments, the system has a plurality of access detection computer circuits corresponding to a plurality of medication storage areas of the detectable drug packaging, wherein each of the storage medication areas having a corresponding access detection computer circuit.

In some embodiments, the system disables an access detection computer circuit for the corresponding storage medication area.

In some embodiments, a user action to access the storage medication area disables access detection computer circuit for the corresponding storage medication area.

In some embodiments, a main access detection computer circuit has an overall unique identity, and a plurality of access detection computer circuits corresponding to a plurality of individual medication storage areas of the detectable drug packaging.

In some embodiments, the storage unit has a lock to enable a closed locked position and an open unlocked position, wherein the control commands trigger the lock to enable the unlocked open position in response to an assignment confirmation message, the storage unit in the open unlocked position capable of containing the detectable drug packaging, the lock further triggering to the closed locked position by detecting the detectable drug packaging in the storage unit, the lock further resists and detects unauthorized access attempts using user-identity input.

In some embodiments, the storage unit has a device-identity known to the central server.

In some embodiments, the user interface further requires the authorized drug manager to enter a verification code of the authenticated storage apparatus before being allowed to assign the authenticated drug storage apparatus to a drug consumer.

In some embodiments, the drug regimen parameters are provided from an external system and exchanged with the central server.

In some embodiments, drug adherence and drug consumption information is further relayed onto external systems over a secure link for further analysis and presentation.

In some embodiments, the drug storage apparatus sends a message to trigger a secondary event; wherein the secondary event may be one or more of making an emergency call, and triggering a secondary drug storage apparatus to begin operation.

In some embodiments, the central server having the hardware processor receives and processes activity messages from the known storage unit's identity with severity indicators that are used to select alarm messages.

In some embodiments, a main access detection computer circuit having an overall unique identity, and a plurality of access detection computer circuits corresponding to a plurality of individual medication storage areas of the detectable drug packaging.

In an aspect, embodiments described herein provide a system for detecting and tracking drug extraction from one or more drug storage apparatus(es) at a central server. The system with one or more authenticated drug storage apparatus having: an access detection computer circuit that integrates with packaged drugs to create detectable drug packaging, the access detection computer circuit providing drug access detection trigger signals when drugs are accessed from the detectable drug packaging; a storage unit having a lock to enable a closed locked position and an open unlocked position, and having a hardware processor that sends control commands to trigger the lock to enable the unlocked open position in response to an assignment confirmation message, the storage unit in the open unlocked position capable of containing the detectable drug packaging, the lock further triggering to the closed locked position by detecting the detectable drug packaging in the storage unit, the lock further resists and detects unauthorized access attempts using user-identity input; a communication device for transmitting secure communication data messages, the access detection triggers signals, and an authentication request containing an identity value for receiving one or more confirmation messages from a central server for verification of the authenticated drug storage apparatus and verification of assignment of the drug storage apparatus, wherein the communication device relays the one or more confirmation messages to the hardware processor; an user-identity input device having an identity input circuit to cause a secure user-identity captured message to be sent by the communication device to the central server confirming that a drug consumer's identity is stored in a drug storage apparatus memory to create an authorized drug consumer record for granting permission to access loaded drugs in the storage unit. The packaged drugs can be pre-packaged or re-packaged drugs, for example. The packaged drugs can be in different formats, such as blister packs of solid oral dosage forms, inhalers, nasal sprays, eye drops (multi-dose & unit-dose), injectables, patches, and so on.

The system involves the central server having a user interface for selecting an authenticated and unassigned drug storage apparatus and defining authorized drug monitoring entities and drug regimen parameters to establish a drug consumption regimen for a drug consumer by generating regimen encoded files with instructions for specific access periods when drugs can be accessed from the authorized drug storage apparatus; a non-transitory memory storing a database of device-identity values for storage units for verifying the authentication request with the device-identity value for the storage unit and generating confirmation messages for the verification of the authenticated drug storage apparatus; a communication interface that: receives the authentication request, the identity captured message and the drug access detection trigger signals from the communication device for identified attempts to access the drugs within the storage unit; transmits the authentication confirmation messages for the verification of the authenticated drug storage apparatus; transmitting the assignment confirmation message to trigger the unlock open position of the storage unit; transmitting the drug regimen encoded files securely to the communication device to provide the instructions for the specific access periods when the packaged drugs can be accessed by an authorized drug consumer from the authenticated drug storage apparatus; transmits a commence dosing message to trigger the start of drug dosing operation when both the drug regimen encoded files are downloaded and when the identity captured message is received related to the authorized drug consumer assigned to the authenticated drug storage apparatus; receiving the drug access detection trigger signals from the communication computer for identified attempts to access the drugs within the storage unit; a hardware processor that: computes drug adherence and drug consumption metrics by processing the drug access detection trigger signals in relation to the drug regimen parameters for one or more authenticated drug storage apparatus; and receives and processes activity messages from the known storage unit's identity with severity indicators that are used to select alarm messages, relays the drug consumption information and alarm messages onto the defined authorized drug monitoring entities.

In some embodiments, the central server interface further requires the authorized drug manager to enter a verification code of the authenticated storage apparatus before being allowed to assign the authenticated drug storage apparatus to a drug consumer.

In an aspect, embodiments described herein provide a central server for detecting and tracking drug extraction from a plurality of drug storage apparatuses, each drug storage apparatus integrating packaged drugs and an access detection device for transmitting drug access detection trigger signals when drugs are accessed from packaging. The central server has a user interface for receiving a verification code for an authorized drug storage apparatus and input defining drug regimen parameters to establish a drug consumption regimen for a drug consumer by generating regimen encoded files with instructions for specific access periods when drugs can be accessed from the authorized drug storage apparatus; non-transitory memory storing a database of identity values for drug storage apparatuses for verifying the authentication request with the identity value for the drug storage apparatus and generating confirmation messages for the verification of the drug storage apparatus; a communication interface for: transmitting the confirmation messages for the verification of the drug storage apparatus; transmitting the drug regimen encoded files securely to the communication device to provide the instructions for the specific access periods when the packaged drugs can be accessed by an authorized drug consumer from the authenticated drug storage apparatus; transmitting a commence dosing message to trigger the start of drug dosing operation when both the drug regimen encoded files are downloaded and when the identity captured message is received related to drugs held by the authenticated drug storage apparatus; receiving the drug access detection trigger signals from the communication device for identified attempts to access the drugs within the packaging; and a hardware processor that uses statistical analysis to compute drug consumption information using the access signals and the dosing regimen information and relays the drug consumption information onto the defined authorized drug monitoring entities.

In an aspect, embodiments described herein provide a method for detecting and tracking drug extraction from a plurality of drug storage apparatuses. The method involves: at one or more authenticated drug storage apparatus, providing drug access detection trigger signals using an access detection computer circuit that integrates with packaged drugs when drugs are accessed from detectable drug packaging; sending control commands using a hardware processor of a storage unit having a lock to enable a closed locked position and an open unlocked position to trigger the lock to enable the unlocked open position in response to an assignment confirmation message, the storage unit in the open unlocked position capable of containing the detectable drug packaging, the lock further triggering to the closed locked position by detecting presence of the detectable drug packaging in the storage unit, the lock further resists and detects unauthorized access attempts using user-identity input; transmitting, by a communication device, secure communication data messages, the access detection trigger signals, and an authentication request containing an identity value for receiving one or more confirmation messages from a central server for verification of the authenticated drug storage apparatus and verification of assignment of the drug storage apparatus; relaying, by the communication device, the one or more confirmation messages to the hardware processor; sending a secure user-identity captured message by an identity input circuit and the communication device to the central server confirming that a drug consumer's identity is stored in a drug storage apparatus memory to create an authorized drug consumer record for granting permission to access loaded drugs in the storage unit; selecting an authenticated and unassigned drug storage apparatus and defining authorized drug monitoring entities and drug regimen parameters at a user interface of the central server to establish a drug consumption regimen for a drug consumer by generating regimen encoded files with instructions for specific access periods when drugs can be accessed from the authorized drug storage apparatus; storing a database of device-identity values at storage units of non-transitory memory for verifying the authentication request with the device-identity value for the storage unit and generating confirmation messages for the verification of the authenticated drug storage apparatus; receiving, at a communication interface, the authentication request, the identity captured message and the drug access detection trigger signals from the communication device for identified attempts to access the drugs within the storage unit; transmitting the authentication confirmation messages for the verification of the authenticated drug storage apparatus; transmitting the assignment confirmation message to trigger the unlock open position of the storage unit; transmitting the drug regimen encoded files securely to the communication device to provide the instructions for the specific access periods when the packaged drugs can be accessed by an authorized drug consumer from the authenticated drug storage apparatus; transmitting a commence dosing message to trigger the start of drug dosing operation when both the drug regimen encoded files are downloaded and when the identity captured message is received related to the authorized drug consumer assigned to the authenticated drug storage apparatus; receiving the drug access detection trigger signals from the communication computer for identified attempts to access the drugs within the storage unit; computing, at a hardware processor, drug adherence and drug consumption metrics by processing the drug access detection trigger signals in relation to the drug regimen parameters for one or more authenticated drug storage apparatus; receiving and processing activity messages from the known storage unit's identity with severity indicators that are used to select alarm messages; and relaying the drug consumption information and alarm messages onto the defined authorized drug monitoring entities.

In an aspect, embodiments described herein provide a system for detecting and tracking drug extraction from one or more drug storage apparatus at a central server. The system involves one or more authenticated drug storage apparatus having: an access detection computer circuit that integrates with packaged drugs, the access detection computer circuit providing drug access detection trigger signals when drugs are accessed from the packaging to resist and detect unauthorized access attempts, a storage unit for containing packaged drugs; a communication device for transmitting secure communication data messages, the access detection trigger signals, and an authentication request containing an identity value for receiving confirmation messages from a central server for verification of the authenticated drug storage apparatus; an unlock device that triggers when the central server sends a confirmation message indicating verification of the authenticated drug storage apparatus; a locking device that triggers by the access detection computer circuit; an identity input device having an identity input circuit to cause a secure identity captured message to be sent by the communication computer to the central server confirming that a drug consumer's identity is stored in memory to create an authorized drug consumer record for granting permission to access loaded drugs on the authenticated drug storage apparatus. The system involves the central server having a user interface for receiving a drug storage apparatus verification code and input defining authorized drug monitoring entities and drug regimen parameters to establish a drug consumption regimen for a drug consumer by generating regimen encoded files with instructions for specific access periods when drugs can be accessed from the authorized drug storage apparatus; non-transitory memory storing a database of identity values for drug storage apparatuses for verifying the authentication request with the identity value for the drug storage apparatus and generating confirmation messages for the verification of the authenticated drug storage apparatus. The system involves a communication interface for: transmitting the confirmation messages for the verification of the authenticated drug storage apparatus; transmitting the drug regimen encoded files securely to the communication computer to provide the instructions for the specific access periods when the packaged drugs can be accessed by an authorized drug consumer from the authenticated drug storage apparatus; transmitting dosing messages to trigger the start of drug dosing operation when both the drug regimen encoded files are downloaded and when the identity captured message is received related to drugs held by the authenticated drug storage apparatus; receiving the drug access detection trigger signals from the communication computer for identified attempts to access the drugs within the packaging; and a hardware processor that computes drug consumption information using the access signals and relays the drug consumption information onto the defined authorized drug monitoring entities.

In some embodiments, the user interface receives input for the number of drugs contained within the packaged drug container and the central servers sends the input to the authenticated drug storage unit.

In some embodiments, the access detection computer circuit further sends a secure communication message to the central server indicating the type and quantity of drugs contained within the authentication drug storage unit.

In some embodiments, the drug monitoring entities comprise a drug consumer computer.

In some embodiments, the system has a logging system that collects historical information from drug monitoring entities to create statistical models around drug adherence by drug consumers.

In some embodiments, the authenticated drug storage unit unlock mechanism can be triggered when the packaged drugs inside the authenticated drug storage unit are exhausted.

In an aspect, embodiments described herein provide a central server for detecting and tracking drug extraction from a plurality of drug storage apparatuses, each drug storage apparatus integrating packaged drugs and an access detection device for transmitting drug access detection trigger signals when drugs are accessed from packaging. The central server has a user interface for receiving a verification code for an authorized drug storage apparatus and input defining drug regimen parameters to establish a drug consumption regimen for a drug consumer by generating regimen encoded files with instructions for specific access periods when drugs can be accessed from the authorized drug storage apparatus; non-transitory memory storing a database of identity values for drug storage apparatuses for verifying the authentication request with the identity value for the drug storage apparatus and generating confirmation messages for the verification of the drug storage apparatus; a communication interface for: transmitting the confirmation messages for the verification of the drug storage apparatus; transmitting the drug regimen encoded files securely to the communication computer to provide the instructions for the specific access periods when the packaged drugs can be accessed by an authorized drug consumer from the authenticated drug storage apparatus; transmitting dosing messages to trigger the start of drug dosing operation when both the drug regimen encoded files are downloaded and when the identity captured message is received related to drugs held by the authenticated drug storage apparatus; receiving the drug access detection trigger signals from the communication computer for identified attempts to access the drugs within the packaging; and a hardware processor that computes drug consumption information using the access signals and relays the drug consumption information onto the defined authorized drug monitoring entities.

In some embodiments, the central server further saves and aggregates all drug access attempts historic access attempts to show statistical information related to drug consumption adherence.

In some embodiments, the access detection computer circuit is a low-frequency radio frequency identification (RFID) computer circuit.

In some embodiments, the access detection computer circuit is a paper-based computer circuit capable of carrying an electrical signal.

In some embodiments, the secure drug storage unit and the drug consumer computer are contained within the same physical housing.

In some embodiments, the drug consumer computer is a cell phone.

In some embodiments, the relay of drug consumption information can include alarms when the drug access regimen is violated.

In some embodiments, the system has a plurality of access detection computer circuits and a corresponding plurality of secure drug storage units, wherein the central server receives access signals generated by the plurality of access detection computer circuits.

BRIEF DESCRIPTION OF DRAWINGS

The following detailed description of the invention is better understood when read in conjunction with the included figures. The included figures are intended to illustrate one implementation of the invention for one skilled in the art. These exemplary illustrations are not intended to limit the disclosure to the specific embodiments shown herein.

DETAILED DESCRIPTION OF DRAWINGS

Embodiments relate to systems and methods for detecting and tracking drug extraction activity from one or more drug containment apparatus at a central server. In particular, embodiments relate to systems and methods for authenticating one or more drug containment apparatuses within the central server and subsequently detecting and tracking drug extraction activity from packaged drugs by drug consumers.

Embodiments described herein also relate to systems and methods for controlling drug extraction activity by drug consumers from one or more drug containment apparatuses. Embodiments further described herein relate to the ability to dynamically associate and authorize a drug consumer to an authenticated drug containment apparatus to create a secure relationship for safe and regulated consumption of drugs follow a drug regimen.

A drug consumer is defined as an authorized person to whom the drugs can be entrusted to. In some embodiments this will be the specific individual who will be consuming the drugs. In other embodiments the drug consumer is a proxy for the person consuming the drugs. For example, if a patient is infirmed then a proxy could be an authorized caregiver with the power of care (POC) over the physical drug consumer. In another example, the drug consumer might be an adult for an underage child that is taking a drug, such as a drug that could be considered dangerous or addictive.

Embodiments described herein also relate to how packaged drugs are augmented by a computer circuit and contained within a storage unit to help regulate an individual's dosing regimen for the packaged drugs.

Figure 1:
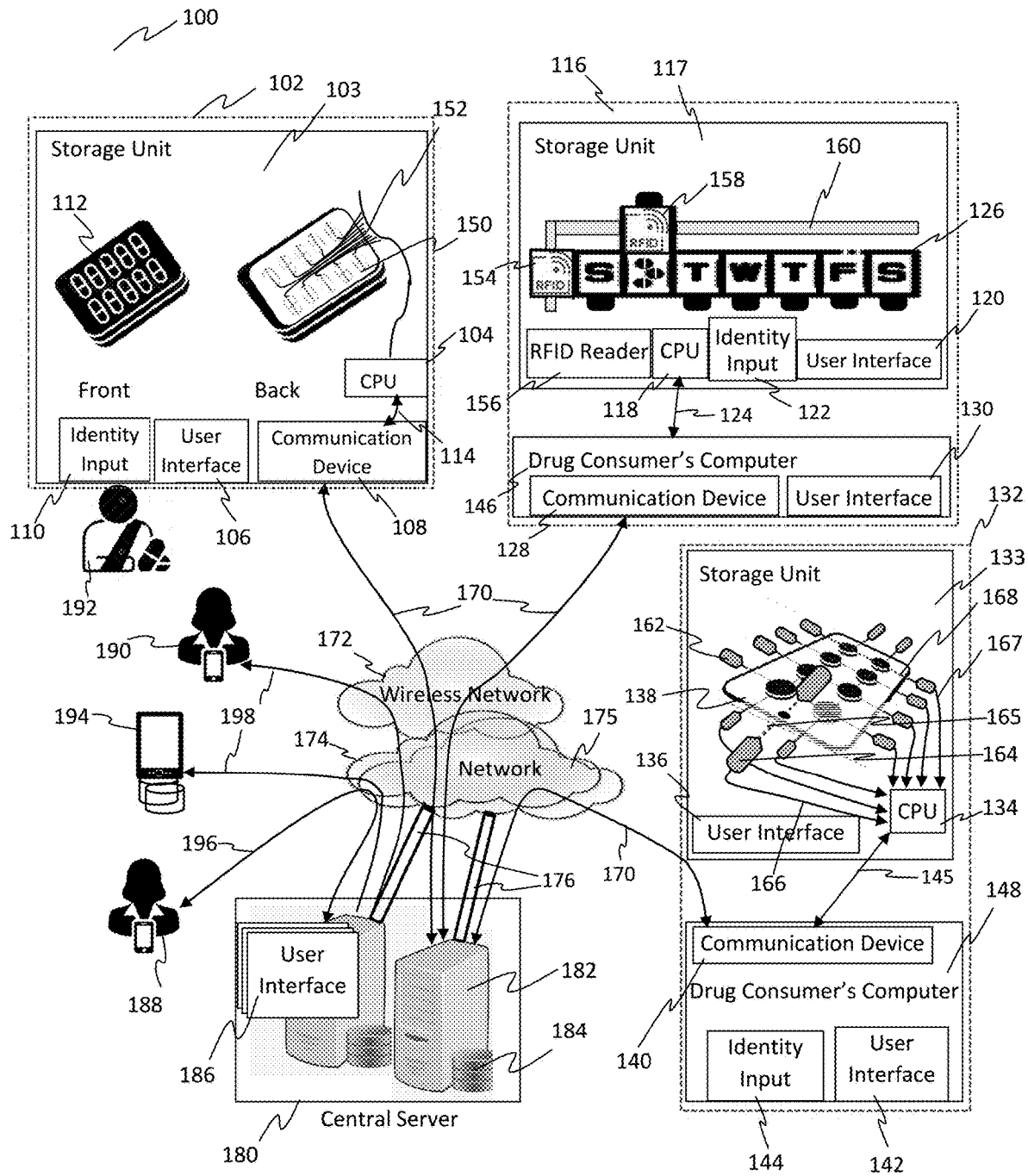
FIG. 1 shows a system for detecting and tracking drug extraction from one or more drug storage apparatus at a central server.

FIG. 1 shows a system 100 for detecting and tracking drug extraction from one or more drug storage apparatuses at a central server.

The system 100 provides for detecting and tracking drug extractions at one or more drug storage apparatus. The system 100 has: a central server having a hardware processor and memory storing drug consumption data. The system 100 has a drug storage apparatus having: a storage unit that couples to an access detection computer circuit that integrates with drug packaging containing one or more medication storage areas. The storage unit contains a device-identity known to the central server. The central server authorizes the drug storage apparatus using the storage unit device-identity. The authorized drug storage apparatus communicates with the central server and exchanges authorization and configuration parameters. The hardware processor has a user interface for defining drug regimen parameters to establish a drug consumption regimen for a drug consumer by generating non-transitory computer readable media storing regimen encoded files with instructions for specific access periods when drugs can be accessed from the authorized drug storage apparatus. The system 100 has a communication interface for the drug storage apparatus and the central server. The communication interface: transmits the confirmation messages for the authorization of the drug storage apparatus; securely transmits the drug regimen encoded files to the authorized drug storage apparatus with instructions for the specific access periods when the packaged drugs can be accessed by an authorized drug consumer from the authenticated drug storage apparatus; transmits a commence dosing message to trigger the start of drug dosing operation when both the drug regimen encoded files are downloaded and when the identity captured message is received related to drugs held by the authenticated drug storage apparatus; receives the drug access detection trigger signals for identified attempts to access the drugs within the packaging. The hardware processor in the central server computes and updates the drug consumption data stored in the memory using the access signals and the dosing regimen information and relays the drug consumption information onto the defined authorized drug monitoring entities.

Drug Storage Apparatus Overview

The system 100 has one or more authenticated drug storage apparatuses 102, 116, 132 that include a storage unit 103, 117, 133 for containing packaged drugs 112, 126, 138 that are augmented by an access detection computer circuit 150, 156, 164 to create detectable drug packaging. Once augmented with packaged drugs, the access detection computer circuit 150, 156, 164 is further able to integrate with storage unit 103, 117, 133 in order to provide drug access detection trigger signals when drugs are accessed from the packaging of the packaged drugs 112, 126, 138.

The system 100 involves use of packaged drugs 112, 126, 138. For the consumption of prescription medication, packaging methods 112, 126, 138 can segregate and isolate drug doses from each other and from the external environment. Different package methods 112, 126, 138 can be used to help guide the drug consumer 192 as to when they should consume their drug doses.

The system 100 addresses concern about the fact that these packaged methods 112, 126, 138 are self-regulating and rely on trust of the drug consumer 192. Additionally, the system addresses concern around drug adherence and the risk of drug consumer 192 harm. The system 100 also helps to eliminate diversion of drugs that is common in the healthcare industry through user-identity and tamper-resistant, tamper-detecting containment methods.

The storage unit 103, 117, 133 is designed and built with a locking mechanism and hardware process to resist and detect unauthorized access attempts using the user-identity input. The locking mechanical design is constructed to allow for loading of the detectable drug packaging and permit specific periods for drug 112, 126, 138 access. Further, the lock mechanism and the hardware processor of the storage unit 103, 117, 133 are able to detect and report on unauthorized access attempts by users whose user-identity does not match the saved user-identity.

In some embodiments, where high risk drugs are in the drug package 112, 126, 138, for example naloxone, multiple user-identities can be saved to allow access to the packaged drugs. For example, this is useful if the primary patient 192 may be suffering from addiction issues and an immediate dose of naloxone is required to treat an overdose. The backup caregiver 190 of the patient can be authorized as a backup drug recipient in order to extract and administer the lifesaving dose of drugs. Such lifesaving drugs 112, 126, 138 can be valuable in the streets and have a high value. Therefore, protecting these types of drugs from theft, and creating a deterrent within a securely locked environment, is an important reason to employ the system 100 described.

The drug storage apparatus 102, 116, 132 has a communication device 108, 128, 140 for transmitting and receiving secure communication data messages 170. Transmitting 170 an authentication request to the central server 180 containing the device-identity value of the storage unit 103, 117, 133, allows the central server 180 to authenticate the drug storage apparatus 102, 116, 132. Access detection trigger signals from the hardware processor within the storage unit 103, 117, 133 are sent 170 to the central server when packaged drugs 112, 126, 138 are extracted by a drug consumer 192.

The drug storage apparatus has a secure storage unit 103, 117, 133 that offers a locking mechanism controlled by the central processing unit (CPU) 104, 118, 134. The lock triggers to unlock the storage unit 103, 117, 133 by receiving a confirmation message 170 at the communication device 108, 128, 140, indicating verification of the authenticated drug storage apparatus 102, 116, 132 has been achieved.

The secure storage unit's 103, 117, 133 locking mechanism can also lock the storage unit 103, 117, 133 by detecting the presence of packaged drugs 112, 126, 138 when augmented by the access detection computer circuit 150, 156, 164 to create detectable drug packaging within the storage unit 103, 117, 133 as discussed herein.

The drug storage apparatus 102, 116, 132 also contains a user-identity input device 110, 130, 144 that allows the capture of a drug consumer's 192 identity. The drug storage apparatus 102, 116, 132 uses the communication device 108, 128, 140 to send a secure "user-identity captured" message 170 to the central server 180 to confirm that a drug consumer's 192 identity is stored in permanent memory of the drug storage apparatus 102, 116, 132. This storage of the drug consumer's 192 identity creates an authorized drug consumer record for granting permission to access loaded drugs 112, 126, 138 loaded in the storage unit 103, 117, 133.

The Central Server Overview

The system 100 has a central server 180 that provides non-transitory memory 184 capabilities for allowing the verification of storage units 103, 117, 133 against a database of all known storage units 103, 117, 133 to create authenticated drug storage apparatuses 102, 116, 132. The central server 180 provides a user interface 186 to allow a drug manager 188 to perform one or more activities with authenticated drug storage apparatuses 102, 116, 132. The user interface 186 also allows the selection of an authenticated drug storage apparatus 102, 116, 132 by the drug manager 188.

In some embodiments, the user interface 186 at the central server 180 allows input of a drug storage apparatus verification code to confirm an authorized drug manager 188 is in possession of an authenticated drug storage apparatus 102, 116, 132.

The user interface 186 at the central server 180 also allows the input of authorized drug monitoring entities 188 for receiving various messages and alerts 198 from the central server 180. The user interface 186 further provides the ability to input drug regimen parameters to establish a drug consumption regimen for a drug consumer 192 by generating regimen encoded files with instructions for specific access periods when drugs 112, 126, 138 can be accessed from the authorized drug storage apparatus 102, 116, 132.

In some embodiments the user interface 186 also allows an authorized drug manager 188 to create files and code that control operations of different drug storage apparatus 102, 116, 132 to implement and control complex drug regimens involving the different drug storage apparatus 102, 116, 132. For example, medications can be correlated. For example, a drug consumer 192 might be taking an inhaled drug like bronchodilator (ex: salbutamol) for an asthma attack if they use this drug they may need to also take the inhaled corticosteroid (ex: fluticasone) just after. There are also complex drug regimen for patients with end-stage cancer treatments, when they are on a long-acting morphine every 12 hours they might be permitted as 'as needed' dose (also known as PRN "pro re nata" in Latin) of short-acting morphine every hour for breakthrough pain. In some embodiments, the PRN does is in a separate dispenser.

In other embodiment the user interface 186 also for a drug manager 188 to define complementary actions based on events happening within the drug storage apparatus 102, 116, 132. For example, if the patient takes a drug like naloxone within the drug storage apparatus 102, 116, 132 then a central server 180 could automatically contact emergency 911 and provide your contact information, location and the nature of the emergency.

In another emergency example, if a drug consumer 192 is taking Nitroglycerin oral spray for the onset of chest pain, the amount of drug consumption could trigger an emergency message to 911. Specifically, if the drug consumer 192 take 1 or 2 sprays, they must wait 5 minutes before taking the third. This limitation can be placed within the drug regimen encoded files 170 given to the drug storage apparatus 102, 116, 132. If the drug consumer 192 attempts to take a fourth spray in less than 15 minutes, then the emergency 911 message should be sent immediately. This Nitroglycerin oral spray only permits three sprays in a 15-minute period, if a fourth spray is attempted sooner it means the drug consumer 192 is still in distress and help is urgently needed.

In another embodiment the user interface 186 can allow the drug manager 188 to set a trigger to turn another a second drug storage apparatus 102, 116, 132 should a drug missed message 170 arrive from a first drug storage apparatus 102, 116, 132.

In some embodiments the user interface 186 allows an authorized drug monitoring entity 188 to access an uploaded drug regimen for a drug consumer as described in FIG. 12. Uploaded drug regimen can come from another system like a Pharmacy Management System (PSM) used by drug managers 188 when prescribing and dispending drugs to drug consumers 192. The drug monitoring entity 188 can then further manipulate, change and assign a drug consumption regimen to an authenticated drug storage apparatus 102, 116, 132.

When the drug regimen contains the names and drug identification number (DIN) of the medicines going into the drug storage apparatus 102, 116, 132 other embodiments are possible for the central server 180. When drug information is present the central server 180 has the ability to compare prescribed drugs within different drug storage apparatuses 102, 116, 132 being used by the same drug consumer 192. This allows for messages and warning to be displayed to the drug manager 188 warning them about drug interactions, conflicts and dangerous prescribing situations. This allows the system to solve a problem within the healthcare industry when a patient coming out of hospital is prescribed medication by a specialist or doctor who is not their family doctor and who fully knowns their medical history.

Packaged drugs can also have barcodes on them identifying what specific drugs are contained within the packaging. When a barcode is present, the drug storage apparatus 102, 116, 132 can have a barcode scanner as part of its system for reading the barcode. Such barcoding information can further assist the system in determining what the drug consumer 192 is taking and will improve the specificity of alerts and alarms should those drugs not be taken on time.

The central server 180 provides a communication interface 176 for receiving authentication requests from drug storage apparatuses 102, 116, 132. The authentication request carries the device-identity of the storage unit 103, 117, 133 that will lead to the authentication of drug storage apparatuses 102, 116, 132. The communication interface 176 also receives the "user-identity captured" message 170 from the authenticated drug storage apparatus 102, 116, 132 when the drug consumer's identity 192 has been captured and stored in the authenticated drug storage apparatus' 102, 116, 132 memory.

The communication interface 176 can transmit confirmation messages 170 verifying the authenticated drug storage apparatus 102, 116, 132, when the device-identity of the storage unit 103, 117, 133 matches a known device-identity from a list of all storage units 103, 117, 133 kept in non-transitory memory at the central server 180.

Further, the communication interface 176 can transmit drug regimen encoded files 170 securely to the communication device 108, 128, 140 associated to the authenticated drug storage apparatus 102, 116, 132. The drug regimen encoded files 170 provide instructions for the specific access periods when the packaged drugs can be accessed by an authorized drug consumer 192 from the authenticated drug storage apparatus 102, 116, 132.

The communication interface 176 at the central server 180 is also capable of transmitting a "commence dosing" message 170 to trigger the start of drug dosing operation when both the drug regimen encoded files are downloaded and the "user-identity captured" message 170 has been received for the authorized drug consumer 192 assigned to the authenticated drug storage apparatus 102, 116, 132. As discussed, in some embodiment the drug consumer 192 is a proxy agent for the specific person who will be ingesting the drugs. Such proxy agents can be needed when a person is infirmed, old, or young for example and assistance is required or is desirable.

The communication interface 176 is further able to receive drug access detection trigger signals 170 from the communication computer 108, 128, 140 for identified attempts to access the drugs 112, 126, 138 within the storage unit 103, 117, 133. The central server 180 further has a hardware processor for computing drug adherence and drug consumption metrics for a drug consumer 192. Various embodiments of calculations can be used to process the drug access detection trigger signals in relation to the drug regimen parameters for one or more authenticated drug storage apparatus 102, 116, 132. For example, calculations can include direct comparisons of dosing times with the times when drugs were extracted from the storage unit 103, 117, 133 by the drug consumer 192, to determine incidents of correct drug consumption, incidents of failed drug consumption, various drug adherence patterns, scatter plots of actual drug consumption times against the recommended configured drug consumption times, and deviations from optimum drug consumption using statistical analysis to name a few methods.

The communication interface 176 can further receive 170 and process activity messages 170 from the authenticated drug storage apparatus 102, 116, 132 with severity indicators that can be used to select alarm messages. Upon selecting an alarm message, the hardware processor can then relay the drug consumption information and alarm messages to defined authorized drug monitoring entities 190, 194.

Drug Storage Apparatus

Different embodiments of drugs storage apparatus 102, 116, 132 shown in FIG. 1 will now be discussed in greater detail. An example is the storage unit 103, 117, 133 that is built and designed to resist unauthorized access attempts. This storage unit 103, 117, 133 is also built to detect attempts to break into the storage unit 103, 117, 133 to access the drugs 112, 126, 138 stored within and send messages 170 to a central server 180 when such an attempt is made. There are different embodiments of the storage unit 103 described herein. The storage unit 103 can have different features, forms and functions for different embodiments.

There are many embodiments to enable this unauthorized access detection that go beyond just using the locking mechanism that secures the drugs behind a locked inner compartment. In some embodiments additional protection is used, for example a light sensor that detects the presence of light when the storage unit 103, 117, 133 should not be opened and exposed to light. This could detect, for example, attacks into the storage unit 103, 117, 133 using drills, saws or other devices that can cut through solid materials like plastic, metal or aluminum. Vibration detection sensors and accelerometers could also be used to detect attempts to smash, drop or damage the unit.

The storage unit 103, 117, 133 contains packaged drugs 112, 126, 138 that are augmented with an access detection computer circuit 150, 154, 164 to create "detectable drug packaging". When used in this application the term "detectable drug packaging" 112, 126, 138 will refer to the combination of packaged drugs and a corresponding access detection computer circuit 150, 154, 164. The detectable drug packaging 112, 126, 138 can also refer to packaged drugs that are brought into proximity of the access detection computer circuit 150, 154, 164 within the storage unit 103, 117, 133 for detection, in order to create the detectable drug packaging 112, 126, 138.

When combined, detectable drug packaging 112, 126, 138 can have various sizes and construction methods. By allowing the insertion of detectable drug packaging 112, 126, 138, the system allows for ease of use and integration with pharmacy systems. The resulting secure storage units 103, 117, 133 can hold many of the current packaging solutions available today, including individual pill blistering, individual pill pouching, liquid vials used within inhaling devices and multipack dispensers (blister packs) to name just a few.

Packing solutions for drugs are designed to provide individual dosing or time-based dosing methods to help regulate and guide the consumption of one or more drugs. In some embodiments a single physical drug could be housed in a single compartment. In other embodiments one or more drugs are housed in multiple dosing compartments that guide the consumer to a time in the day when consuming those drugs is prescribed. In other embodiments a liquid drug can be divided into specific vials or containers to be used in puffer or injection devices.

In some embodiments packaging can also assist with 'as needed' (PRN) type dosing methods. Such packaging might help limit the consumption guidelines to a regulated dosage. For example, such verbal and packaging instructions might include a statement like two pills as needed or take one pill as needed. Such instructions are commonly used with pain management after surgery or many other complicated and painful medical procedures. For example, instructions or conde might specify that a patient should take drugs as needed (in view of defined thresholds, for example) and the dosing can still be tracked and controlled by the system.

Current solutions for these housing methods divide up the drugs to assist in regulation, with verbal instructions for the patient. Such packaging has no direct enforcement or protection of the drugs within the packaging. Without protection or regulation, the drug consumer is left to deal with theft of their product, or the potential of over-medicating for pain management. For example, directions such as 1 or 2 tablets of an acetaminophen/opioid medication as needed could have safety concerns if not regulated difficult problems of over-medicate themselves especially when pain management is involved.

The drug storage apparatus 102, 116, 132 solves the enforcement, reminder and protection problems. It further helps to stop the diversion of drugs that leads to drug abuse, theft and drug addictions. Further, the drug storage apparatus 102, 116, 132 removes reliance on self-regulating of drug consumption and prevents full access to all the prescribed drugs by anyone with physical access to the packaging. By improving drug adherence, the staggering costs to health care, caused from the side effects of improper drug consumption can be mitigated.

When detectable drug packaging 112, 126, 138 is placed within the storage unit 103, 117, 133 that makes up a part of the drug storage apparatus 102, 116, 132, the drug consumer 192 can be guided through a precise dosing regimen, indicating exactly when their drugs 112, 126, 138 are to be consumed. Further, the drug storage apparatus 102, 116, 132 uses the drug consumer's 192 identity information to enforce and confirm the dosing regimen execution. One or more drug storage units 103, 117, 133 can provide individual dosing compartments or multiple dosing compartments within a larger drug storage unit 103, 117, 133, which further restrict and guide the drug consumer 193 as to when to take the drugs 112, 126, 138 contained in each dosing compartment.

The storage unit 103, 117, 133 also provides an added level of secure access to the drugs 112, 126, 138 contained within it. Using the CPU, memory, and various unlocking and locking mechanisms, the storage unit 103, 117, 133 enforces tamper resistance and tamper detection. In cases where the packaged drugs are very expensive or highly addictive, the level and difficulty of breaking into these storage units 103, 117, 133 to steal the detectable drug packaging 112, 126, 138 can be extremely difficult. There are many electronic locking embodiments that can be used in the storage unit 103, 117, 133. For example, a magnetic lock, or mag lock may be used to electronically lock the storage unit 103, 117, 133. This type of lock uses an electrical current to induce magnetic fields that lock or unlock a door.

Another lock embodiment could be the use of a solenoid locking mechanism. The solenoid lock throws a physical bolt or moving a plunger into, and out of a receptacle. This embodiment is especially useful as it can be designed to enter a locked state should all power be taken away from the storage unit 103, 117, 133. This and other solutions can be employed for locking and unlocking the storage unit 103, 117, 133 and for providing drug loading capabilities and drug extraction capabilities.

Other components of the drug storage apparatus 102, 116, 132 include a CPU 104, 118, 134, memory, a user interface 106, 130, 136, a user-identity input device 110, 122, 144, and a communication device 108, 128, 140. The drug storage apparatus 102, 116, 132 may also be battery powered and in some embodiments this battery may be rechargeable. In other embodiments, the drug storage apparatus 102, 116, 132 must be plugged into a power source to operate.

In some embodiments the user interface 106, 130, 136 might be very simple such as one or more LED lights or a small digital display. In other embodiments the user interface 106 might be very complex and provide a full video and audio user interface. In some embodiments there are multiple user interfaces 120, 130, 136, 142 that together provide two levels of user interface for the drug consumer 192. For example, one level might be a simpler LED or audible sound interface to provide notifications and the second level might include a full display with dashboard readouts of drug consumption times and dates.

The Communication Device

The drug storage apparatus 102, 116, 132 contains a communication device 108, 128, 140. There are multiple embodiments for how the drug storage apparatus 102, 116, 132 can make use of a communication device 108, 128, 140. For example, in one embodiment the communication device 108 is contained within the same physical housing as the storage unit 103. In this embodiment, the communication 114 between the storage unit 103 and the communication device 108 can be via a direct computer circuit 114. In some embodiments, multiple CPUs 104 would be used, while in other embodiments a single CPU 104 is powerful enough to perform all the necessary functions of the communication device 108. In some embodiments, the communication device 108 could be an Internet of Things (IoT) based chipset that supports machine-to-machine communication cellular connections to wireless networks 172 such as LTE-M1 type wireless protocols.

In other embodiments, the communication device 128, 140 that makes up part of the drug storage apparatus 116, 132 is housed in a physically separate computer 146, 148 that communicates to the storage unit 117, 133 using a direct communications protocol 124, 145 such as, for example, Bluetooth, NFC, 802.11 (WiFi) or proprietary methods. There are many embodiments for a separate drug consumer's computer 146, 148 such as a personal cell phone, a tablet computer, a laptop computer, a wearable computer such as a smart watch, a reading tablet, and many others. The drug consumer's computer 146, 148 might connect through wireless networks 172 or in some cases through wired networks 174 to reach the central server 180.

There are many embodiments for a drug storage apparatus 102, 116, 132 using a communication device 128, 140 that is not physically in the same housing as the storage unit 117, 133. In some embodiments there is a special drug storage apparatus software program running on the drug consumer's computer 146, 148 monitoring the status of the storage unit 117, 133 and indicating when the drug consumer 192 is permitted to access the drugs 126, 138 stored within. Loading software as an application or cell phone app is commonly done with personal cell phone technology and allows for these types of extensions.

In other embodiments, the user-identity input device 144 is also running on drug consumer's computer 148. In these embodiments, where the user-identity input device 144 is not running in the same physical housing as the storage unit 133, this coupling can be changed at the central server 180 but may not be changeable by the drug consumer 192 as a result of the drug consumer's computer 148 securely storing the drug consumer's identity for drug removal. This user-identity is needed for the drug storage apparatus 132 to function correctly. This kind of secure storage is performed using secure enclave computer chips that are tamper-proof and can retain information without providing outside access. For example, once a biometric like a fingerprint is provided and stored within the secure enclave, subsequent fingerprints are provided to the secure enclave and a match is performed and the result is provided and nothing more.

In embodiments in which the user-identity input 122 is housed with the storage unit 117, it may be possible for the drug consumer 192 to change their computer 146 and re-load any apps that might have been previously loaded to allow full drug storage apparatus 116 operation. The communication path 124 can then be re-established to offer the storage unit 117 a communication device 128 and additional user interface 130 capabilities to complete the authenticated drug storage apparatus 116.

Storage Unit Identification

Each storage unit 103, 117, 133 is built with a unique device-identity that is created during the manufacturing and provisioning process for each unit. This unique device-identity is then exchanged with the central server 180 to save in its non-transitory database 184. This central server database 184 contains a list of all storage units 103, 117, 133 to ensure a secure data communication and message 170 security between the central server 180 and all authenticated drug storage apparatuses 102, 116, 132.

There are many embodiments for creating or extracting a unique device-identity associated with a storage unit 103, 117, 133. For example, in some embodiments an identity chip could be built into the printed circuit board (PCB) of the storage unit 103, 117, 133 and could be read during provisioning and shared with the central server 180. In some embodiments, the storage unit 103, 117, 133 device-identity value might be only shared machine-to-machine while in other embodiments it might be printed on the outside of the storage unit 103, 117, 133 like a serial number. In yet other embodiments, the device-identity value could be shared privately with the central server 180 a serial number, which is printed on the outside of the storage unit 103, 117, 133, can be used by the drug manager 188 to select the drug storage apparatus 102, 116, 132 they wish to take control over.

In some embodiments, the device-identity value is injected into the storage unit 103, 117, 133, for example as an encryption certificate. Encryption certificates are used as the basis for encrypting data and verifying communication entities. In one embodiment, a certification could be created by a third-party certificate authority (CA). In another embodiment the central server 180 acts as a CA and creates a certificate. In these embodiments, the unique certification would be exchanged in a secure location, such as the manufacturing plant as each storage unit 103, 117, 133 is first powered up and tested at the completion of manufacturing.

In other embodiments, a dedicated advanced encryption standard (AES) secure enclave chip is used to hold an unchangeable AES key in tamper-proof memory. This value can be read and shared with the central server 180 at the end of the manufacturing process.

There are also embodiments using unique serial numbers built into CPU chips by the chip manufacturers. Such serial numbers are offered by many of the major chip manufacturers including Intel and AMD. In yet other embodiments in which a hardware network interface device is used in the storage unit 103, 117, 133, a media access control address (MAC address) that is unique and can be used in 802.11, Ethernet, WiFi and Bluetooth implementations may be used as the device-identity value. Internationally, there is also the Electronic Product Code (EPC) that can be built into the PCB and then exchanged with the central server 180 for use as the device-identity value.

The Access Detection Computer

To provide the ability to detect and track drug regimen adherence, the drug storage apparatus 102, 116, 132 includes a storage unit 103, 117, 133 that is coupled with detectable drug packaging 112, 126, 138, comprising an access detection computer circuit 150, 154, 164 combined with packaged drugs. The access detection computer circuit 150, 154, 164, is able to couple with packaged drugs due to its construction and design to create detectable drug packaging 112, 126, 138. Different types of access detection computer circuit 150, 154, 164 designs are discussed and highlighted in FIG. 1. The access detection computer circuit 150, 154, 164 in the detectable drug packaging 112, 126, 138 can detect the presence of the corresponding packaged drugs.

The detectable drug package 112, 126, 138 is coupled to the storage unit 103, 117, 133 to provide the ability to detect access to different doses of drugs contained in the detectable drug packaging 112, 126, 138 and can relay attempts to access the drugs from the detectable drug packaging 112, 126, 138 to the central server 180. This automated solution is directed to problems of adherence tracking when taking packaged drugs. There are several embodiments for how the access detection computer circuit 150, 154, 164 could be integrated into the storage unit 103, 117, 133.

For example, in one embodiment, illustrated in FIG. 1, the access detection computer circuit 150 is composed of an electrically conducting paper circuit that can be adhered onto the back of the container of the packaged drugs to create detectable drug packaging 112. This adhesion can by implemented using a moderately sticky glue or adhesive product and be applied at the pharmacy or by anyone with access to the packaged drugs 112 before loading them into the storage unit 103. In some embodiments a person in authority can add the access detection computer circuit 150, 154, 164 in a nursing home, a long-term care home or even at the drug consumer's home.

In this embodiment, paper circuit traces 152 are built across the perforated openings to each of the dose compartments in the drug packaging, such as a multi-pack dispenser or pill blistering dosing compartments 112. These paper circuit traces 152 are then connected to a printed circuit board (PCB) using various embodiments. In one embodiment the coupling could be on contact when the storage unit 103 is closed. There could be a cabling connector used that couples to the PCB that contains the CPU 104 of the drug storage apparatus 102, 116, 132.

The CPU 104 terminates one or more paper circuit trace lines 152 and provides an electrical current that indicates the circuit is connected, broken or has changed its electrical current. In this embodiment, when the drug consumer 192 breaks open an individual dose compartment, the circuit trace line 152 that covers that access point is affected, sending a signal to the CPU 104. The dosing compartment associated with that unique location, is then identified by the CPU 104 based on the design of the access detection computer circuit 150.

There are many possible configurations for the access detection computer circuit 150 using the paper circuit traces, 152. For example, in some embodiments a multi-pack dispenser allows a drug consumer 192 four doses of drugs per day for a maximum of 7 days. The access detection computer circuit 150 for this packaging method would allow for 28 dosing compartments to be detected when accessed by a drug consumer 192. In other embodiments, the access detection computer circuit 150 might cover two doses per day for 5 days, as shown in FIG. 1 at 112. There could be other access detection computer circuit 150 configurations for different daily dosages and dosing periods.

There are several embodiments that may be used by the CPU 104 to detect a broken electrical trace has taken place. In one embodiment the electrical traces 152 across the drug access slots are broken into days of the week. In this embodiment, when drug consumer access drugs and breaks the electrical trade, the electrical signal strength will vary across a given day to indicate to the CPU 104 that a dose has been taken that day. Based on the size of the change, the CPU 104 will be able to detect which of 'N' doses that day has been removed and relay this to the central server 108.

In another embodiment there is an electrical circuit trace 152 across every dosing compartment. Once any of the trace lines are broken the electrical current through that trace is stopped which is detected by the CPU 104. Although there are many ways to build the circuit path to uniquely identify the dosing compartment, they all result in the same unique identification of a specific dosing compartment. Once the dosing compartment is known, the CPU 104 relays that information to the central server 180 via the communication device 108. In this embodiment, the paper circuit traces 152 that terminate at the CPU 104, make up the access detecting computer circuit 150. Additional details on this solution are provided in subsequent figures.

In another embodiment, also illustrated in FIG. 1, the use of near-field communication (NFC) RFID chips 154, 158 can be used to augment many types of drug packaging to create detectable drug packaging 126. In these NFC and RFID embodiments, when a passive (i.e. non-powered) NFC chip, is moved into proximity to an inductive coil 160, the resulting electromagnetic coupling powers the passive near-field RFID. There are several embodiments that may be used to employ NFC chips 154, 158 as access detection computer circuits.

In one embodiment, a first NFC chip 154 is inserted into a specially designed slot in the packaged drug container 126 and is then used to identity the entire packaged drug container 126 to created detectable drug packaging 126. In the embodiment illustrated in FIG. 1, this first NFC chip 154 extends the length of the drug container 126. In other embodiments this first NFC chip 154 could extend the width of the drug container 126 and there could be many other physical embodiments for holding this first NFC chip 154. When the drug package 126 is placed into the storage unit 117 the first NFC chip 154 is immediately powered on by the inductive coil's 160 presence. When activated, the NFC chip 154 provides its identification to an RFID reader 156 that is coupled to the CPU 118 and detectable drug packaging 126 is enabled. This is especially useful if the number of slots provided by the packaged drugs contain a very large number of drugs. Once the first NFC chip's 154 identity is provided, all other remaining NFC chips 158, in each of the separate compartments, can be assigned an identity number based incrementally from the main NFC chip's 154 identification number. The manufacturer and programming of RFID and NFC chips allow for this ability to cluster RFID identification codes.

In the embodiment illustrated in FIG. 1, each time a compartment is opened, the NFC chip 158 installed in the top-lid of the compartment touches the inductive coil 160 and is powered on to provide its identity number to the RFID reader 156. Once this unique identity number is read by the RFID reader 156, the specific dosing compartment is known based on the between the number and the main RFID's 154 identification number. For example, if the main RFID's 154 identification is 112000 and a compartment's RFID chip 158 identification number read is 1120022, then the CPU 118 knows this is the $22^{nd}$ dose taken by this drug consumer 192. This information 170 is then relayed back to the central server 180 through the communication device 128. In other embodiments each compartment could have the NFC chip 158 installed in another place besides the lid or top of the compartment.

In another embodiment an NFC chip 154 is adhered onto a blister pack and creates detectable drug packaging (this embodiment is not illustrated in FIG. 1). In this embodiment, a pharmacist might adhere the first NFC chip onto the packaged drugs and it cannot be removed without damaging the operation of the RFC chip 154. Therefore, only when a non-damaged RFC chip 154 is loaded and detected will a confirmed detectable drug package allow for normal dispensing operation.

In another embodiment, illustrated in FIG. 1, one or more infrared beam circuits 162, 164, comprising an infrared beam generator capable of generating an infrared beam 165 and an infrared beam receiver that can detect the presence of an infrared, are used in proximity to the packaged drugs to create detectable drug packaging 138. Only when the correct packaged drugs are added and the infrared beam 165 generated by the infrared beam circuit 164 is broken will the infrared beam circuit 164 send the correct signal 166 to the CPU 134 confirming that drugs have been inserted in the detectable drug packaging 138. There are several possible embodiments for the use of infrared beams 165. In one embodiment, when the infrared beam 165 is broken by the drug consumer's 192 actions, a signal 166 is sent to the storage unit's CPU 134.

In another embodiment, the infrared beam 165 starts as non-connected and when the packaged drugs 138 are placed into the correct location it moves an infrared beam block or wall (this embodiment is not shown in FIG. 1). When this block is removed, there is a clear path for the infrared beam 165 to travel between the generator and receiver in the infrared beam circuit 164.

Once detectable drug packaging 138 has been inserted and acknowledged by the CPU 134 of the storage unit 133, the system is enabled for drug extraction by an authorized drug consumer. Additional infrared circuits 162 and infrared beams 168 can be used to send signals 167 to the CPU 134 when any drugs are extracted. In one embodiment, this action could take place when a drug consumer reaches through an infrared beam 168, triggering a break in the beam 168, which causes a signal 167 to be sent to the CPU 134 by the corresponding infrared beam circuit 162. Using a matrix of infrared beams 168, the particular broken beam 168 can be isolated to determine the specific dose that has been taken by the drug consumer 192. This information is passed from the CPU 134 to the communication device 140 to send a message 170 to the central server 180. In another embodiment, when a pill is removed the infrared beam 168 is uninterrupted and the infrared beam circuit 162 sends a signal 167 indicating a pill has been removed. This embodiment is not shown but works best when there is a single line of pills rather than a grid of pills in both an X axis and a Y axis.

In another embodiment not illustrated in FIG. 1, the packaged drug is a vial containing a drug formulation. Originally mass produced, the drug is then divided into smaller vials to allow for individual dosing requirements. In some embodiments, the vial contains a drug that will be inhaled by a puffer or inhaler type device. In other embodiments the packaged vial might be for an insulin injection pump or digital injection system. In this embodiment the vial is considered to be the packaged drugs.

The contents of the drug formulation in the vial might be a liquid, vapour or powder-based drug formation. As such there are several different drug storage apparatuses that may be needed to expel the drug formulation. In one embodiment, the drug storage apparatus is a digital inhaling system that has a biometric identity lock that will not allow the inhaler to expel any drug formulation until the user-identity is confirmed. In another embodiment the drug storage apparatus is a digital insulin or biologic immunology injection system that uses a user-identity method to allow injections of insulin or biologic immunology medication. In another embodiment the drug storage apparatus is a pain management system that uses a syringe to inject a liquid formulation into the bloodstream of a drug consumer. When a vial package is placed into each of these drug storage apparatuses one or more methods can be used to detect the package's presence, lock the storage unit and allow the drug storage apparatus to being executing the regimen parameters. In other embodiments eye drop formulations can be held within a vial being inserted. In other embodiments mouth drops, packaged worn drug patches and sublingual film drugs are within the packaging. The drug dispensing apparatus can work with eye drops or a mouth dropper or a patch or a sublingual film, for example.

In one embodiment the storage unit uses an infrared beam within the drug storage apparatus to detect the insertion of the vial of drugs. In another embodiment a passive RFID chip is affixed to the vial before it is inserted into the storage unit to detect the presence of packaged drugs. Other methods might also be used within the storage unit to detect the insertion. For example, a small weight detection chip might be able to detect small weight changes and can detect that a full vial of drugs has been added to the storage unit.

Only when the vial is inserted does the storage unit detect the arrival of the packaged drugs and allow the locking of the storage unit. In some embodiments the infrared beam will become disrupted to detect the presence of the drugs. In other embodiment a passive RFID chip will be detected when it is moved into contact with a RFID inductive coil that powers the chip into an enabled mode and produces an RFID identification number. In another embodiment, the weight calibration reaches a configured level which indicates the correct.

The example continues as the storage unit is locked by detecting the packaged vial drugs. Once downloaded the drug regimen and operational parameters are executed by the drug storage apparatus to allow for the proper dosing of the drugs. As each individual dose is taken, a user-identity is provided, and a drug actuator action is preformed. Each time the actuator action is performed the drug storage apparatus reports that a dose has been extracted. In some embodiments the actuator action is detected by depressing the inhaler that expels the vapour to be inhaled by the drug consumer. In another embodiment the actuator action is the depressing of a plunger or piston to expel a controlled amount of the vial contents. In another embodiment, a small weight detection method is used that detects the change in weight equivalent to one or more doses of a drug being taken by the drug consumer. Each of these embodiments causes an indication of drug consumption back to the central server 180.

In embodiments with a lockable actuator, both vapours and injectables, the ability limit the timing of consumption can make the difference between life and death. For example, as mentioned, a nitroglycerin oral spray can only be taken 3 times in a 15 minute time period. Even the third dose must be taken 5 minutes after the first two sprays. In an emergency when a drug consumer 192 is experiencing severe chest pain, it is extremely difficult to time exactly when 5 and 15 minutes have expired. The drug storage apparatus 102, 116, 132 offers a solution to this difficult problem and can remove the chance of accidental death caused by over-consumption of a strong drug like nitroglycerin.

User-Identity Input

The drug storage apparatus 102, 116, 132 encompasses a user-identity input 110, 122, 144 component. In some embodiments a user-identity input 110, 122 component is integrated into the storage unit 103, 117. In other embodiments the user-identity input circuit 144 is provided by the drug consumer's computer 148. As mentioned previously, drug consumer's computers 146, 148 like cell phones, smart phones, tablets, laptop computers, wearable computers like watches and other future computer systems can be used in conjunction with the storage units 117, 133.

The drug consumer 192 user-identity may be established according to several embodiments. For example, this might take place through biometric input such as fingerprint, eye scans, facial recognition, voice recognition or many other methods. The drug consumer 192 might also have a sub-dermal, embedded user-identity chip for their identification and the user-identity input 110, 122, 144 can read this sub-dermal chip. There could be other embodiments where a photograph must be transmitted back to the central server 180 and a trained professional acting as the drug manager 188 must confirm the drug consumer's 192 user-identity in conjunction with a fingerprint or other biometric scan from the user-identity input mechanism 110, 122, 144.

The drug storage apparatus' 102, 116, 132 uses the user-identity input is to store the user-identity of the drug consumer 192 into a non-transitory memory. Then, once stored, it can be used later for drug extraction by matching the same user-identity of the drug consumer 192. Storage of drug consumer's user-identity can take place in tamper-proof memory solutions. For example, the use of secure enclave storage methods results in tamper-proof, completely private storage of biometric information. These and other solutions allow the drug storage apparatus 102, 116, 132 to confirm the presence of the drug consumer's user-identity 192 via a secure "user-identity captured" message 170.

The Central Server

The central server 180 and its associated database 184 can be implemented according to many embodiments. In one embodiment, one or more CPUs 182 are placed in an Internet central cluster location for public rental. This can be referred to as a cloud-computer product offering. These cloud-based solutions offer high reliability, great flexibility, excellent speed, and the ability to expand CPU requirements as needed. In another embodiment, the central server 180 is housed within a large corporation and provides a dedicated server to an organization. This might be a research facility, a hospital or a major drug manufacturer. Such central servers 180 would be ideally suited for clinical drug trials and other environments where drug tracking and drug adherence is important.

The central server 180 provides a communication interface 176 which connects to one or more networks 174, 175. These networks 174, 175 could include multiple links to a public network like the Internet. The practice of using multiple communication interfaces 176 can be used to achieve fault-tolerance and faster throughput speeds between the central server 180 and the networks 174, 175. In other embodiments, the one or more communication interfaces 176 could include a virtual private network (VPN) 174, a local area network (LAN) 175 or some combination of different networks 174, 175, including both public and private networks. In some embodiments, the central server 180 might be operating in a network serving a large hospital or medical facility, or many other types of networks. A communication path 170 is formed from the central server

180 to the communication device 108, 128, 140 through one or more networks 174, 175, 172 to allow the exchange of secure messages.

In some embodiments, a wireless network 172 is used to provide a link to the communication devices 108, 128, 140. Mobility is an advantage for communication devices 108, 128, 140 when supporting drug storage apparatuses 102, 116, 132 and the storage unit 103, 117, 133. In some embodiments, the communication device 108 uses an Internet of Things (IoT) embedded chipset to communicate to a wireless network 172. There are different cellular communication options that could be employed, including GSM, GPRS, EDGE, LTE, UMTS, 3G, 4G, and 5G options. These might be combined with an 802.11 (WiFi) link or Bluetooth depending on the coverage of various networks in different locations. In other embodiments, there could be a fixed link, such as an Ethernet cable used from a laptop or desktop computer system 146, 148.

This communication path allows the communication device 108, 128, 140 to exchange secure messages 170 through the communication interface 176 at the central server 180. If a secure communications protocol such as AES, TLS, DTLS or another transport secure protocol cannot be used, then end-to-end encryption methods can be employed to ensure security. In some embodiments, a combination of transport security and private end-to-end encryption methods can be used to ensure exchanged data stays encrypted through all transfer points and all network hops. These embodiments could use a symmetrical key installed during manufacturing. The two ends could also negotiate a new key and use an asymmetrical security method, such as, for example, elliptical curve cryptography. In some embodiments, the storage unit 103, 177, 133 device-identity value acts as a seed value for negotiating a shared symmetrical key, for example in an encryption key negotiation solution such as simple password exponential key exchange (SPEKE), elliptical-curve Diffie-Hellman key exchange, or quantum-safe negotiated symmetrical keys.

The central server 180 also acts as a trigger point for specific events that can take place at the drug storage apparatus 102, 116, 132. These trigger points will be discussed later in detail but can support a wide array of complex drug regimen, clinical drug trial requirements and sensitive drug situations (for example in the case of addictive drugs, drugs that are at risk of diversion or drugs which necessitate a high degree of adherence or some other action to be taken after they are consumed). Using the secure and authenticated connection between the central server 180 and the drug storage apparatus 102, 116, 132 a strong cause and effect set of actions can be defined using events within the drug storage apparatus 102, 116, 132.

For example, triggers can be set for events like first drug extracted from the device, every drug extracted from the device, a missed dose not taken from the device, all drugs being exhausted from the device, a failure in the device and many others. Configuration by drug managers 188 can allow them to create actions when these triggers are detected by the central server 180. For example, when a first drug is taken from a device, the central server 180 should make a call to 9-1-1 to alert emergency personal. Taking two or three drugs too close together, might trigger a second drug storage apparatus 102, 116, 132 to deploy and start dispensing drugs. If the drug consumer 192 misses a drug dose this might trigger a second drug storage apparatus 102, 116, 132 to deploy and start dispensing a milder form of the drug, and many other combinations.

Device Authorization

Across this secure link, the drug storage apparatus 102, 116, 132 can attempt to utilize the communication device 108, 128, 140 to initially send an authentication request 170 containing the unique device-identity of the storage unit 103, 117, 133. As discussed above, this device-identity is unique, created during the manufacturing and provisioning process for each unit, and shared with the central server 180. The secure transmission of the storage unit's 103, 117, 133 unique device-identity makes the presence of the drug storage apparatus 102, 116, 132 captured and stored in data at the central server 180.

This step indicates to the central server 180 that the storage unit 103, 117, 133 is now powered on, and that all elements are connected for communicating secure messages 170. The drug storage apparatus 102, 116, 132 leverages the storage unit's 103, 117, 133 shared device-identity value held in non-transitory memory at the central server 180 to build trust. By utilizing the capabilities of a communication device 108, 128, 140, the storage unit 103, 117, 133 is able to send and receive messages allowing it to confirm its ability to exchange secure messages 170.

When the storage unit 103, 117, 133 is first utilized by a drug consumer 192, this initial step starts the process of first use. The reception of a confirmation message 170 from the central server 180, informs the drug storage apparatus 102, 116, 132 that it has been authenticated and that the storage unit 103, 117, 133 is known. In some embodiments, the drug storage apparatus 102, 116, 132 will then make this successful step known through one or all of its user interfaces 106, 120, 130, 136, 142 to the drug consumer 192 or owner of the drug storage apparatus 102, 116, 132.

In some embodiments, the user interface 106, 120, 136 might be simple, such as a green LED which illuminated to indicate that the drug storage apparatus 102, 116, 132 is ready to operate. In other embodiments, a larger and more complex interface 130, 142 might be utilized by the drug storage apparatus 116, 132 to display a detailed status message and/or storage unit 103, 133 information, and to indicate the system is ready to proceed with the drug regimen configuration stage.

Central Server User Interface

The central server 180 can offer one or more user interfaces 186 to perform a range of functions. The user interface 186 might support Internet browser style of interactions 196, using HTTP and HTML type protocols. The user interface 186 could also support advanced JSON application program interface (API) type procedures used with a web framework like React and React-native. In some embodiments, the user interface 186 supports interactions from mobile devices such as cell phones, tablets and wearable computers.

Drug Manager Confirmation

The central server's 180 user interface 186 can be used to authorized drug managers 188 and provide them access into the drug storage apparatus 102, 116, 132 management area. There are many embodiments as to how this can be achieved, depending on the installation and environment in which the central server 180 is running. Since the drug manager 188 can effectively be anyone, there are several methods can be used to validate them and ensure safety for the drug consumer 192 and drug storage apparatuses 102, 116, 132.

In one embodiment, the drug manager's 188 authority could be linked to the method used to connect 196 to the central server 180. For example, a connection may be rejected or approved based on whether it was made through an approved network with pre-established secure login parameter for trusted users. In such an embodiment, if a connection 196 was attempted via a private VPN type network 174, for example through a closed WiFi network within a hospital accessible only through pre-establish staff logins and passwords, then the connection would be approved. However, if the connection 196 was attempted using a public network like the Internet 174, then verification would not be possible and the connection would be rejected.

In some embodiments, the drug manager 188 might be a pharmacist, doctor, nurse, or another trained professional. These professionals are familiar with prescribing prescription drugs and packaged drugs. They could be granted access through a regulated organization for their profession, for example like the College of Doctor's and Physicians. They could have been granted access through a government organization, for example through a public security offering like PrescribeIT™ in Canada, or through some other secure mechanism.

In other embodiments, the drug manager 188 is a caregiver or the drug consumer 192 themselves. In those embodiments where the drug manager 188 is also the drug consumer 192, they might wish to prevent children in the home from consuming their drugs, they might want to have a strong reminder process in place for their drug use, or they could be protecting themselves from abusing the drugs they have been prescribed. In some embodiments, the user interface 186 at the central server 180 requires nothing more than the drug manager 188 to create a login and password for themselves in order to grant access to the central server's 180 managed drug storage apparatuses 102, 116, 132.

In some embodiments a caregiver or parent might act as a proxy for the drug consumer 192. In this way the drugs are protected from the drug consumer 192 who could be at risk of becoming addicted or might divert the drugs. The system provides methods to allow a proxy drug consumer to extract a dose of drugs and provide them to another person in a very careful and guarded way. In other circumstances the drug consumer 192 might have a mental disorder like dementia or severe arthritis and may need a great deal of support in their drug consumption needs.

Drug Storage Apparatus Verification

Only after the central server 180 has confirmed that a known storage unit 103, 117, 133 has made its presence known inside of a drug storage apparatus 102, 116, 132, the data for the storage unit 103, 117, 133 can be located within the central server's 180 database 184. A known storage unit 103, 117, 133 cannot be selected by a drug manager 188 to perform some action until it connects 170 to authenticate the drug storage apparatus 102, 116, 132. In some cases, the drug manager 188 might be attempting to assign the drug storage apparatus 102, 116, 132 to a patient for the first time. In other cases they might be modifying the dosing regimen or some other behavioural configuration setting for that drug storage apparatus 102, 116, 132.

As previously mentioned, the drug manager 188 can verify a drug storage apparatus by logging into the central server 180 and selecting the correct drug storage apparatus 102, 116, 132. In some embodiments, the drug manager 188 may can scan a bar code or a QR code on a drug storage unit 103, 117, 133 that encodes the unique device-identity to complete verification. This may be useful, for example, in cases where a drug manager 188 must verify a large volume of drug storage apparatuses, as this improves speed and reduces the likelihood of input errors as compared to other verification methods, for example manual input of a serial number. This procedure results in the scanned bar code being placed into the field needed for identification and no further verification is required.

In other embodiments, there is an layer of security to ensure the drug manager 188 are in possession of a valid and authenticated drug storage apparatus 102, 116, 132. This helps to protect from nefarious individuals that might be trying to hack the system and disrupt the operation of drug storage apparatuses 102, 116, 132. In some embodiments a drug manager 188 might simply be able to scan a bar codes or a QR code to prove they have a specific drug storage apparatus 102, 116, 132 in hand. In other embodiments the drug manager 188 may have to go through a verification process to confirm they are in possession of an authenticated drug storage apparatus 102, 116, 132. In other embodiments the drug manager 188 can first scan a bar code or QR code and then still have to perform the verification process to ensure they are holding the drug storage apparatus 102, 116, 132 in hand. Different levels and types of security measures can be employed to protect the integrity and the operational state of the drug storage apparatus 102, 116, 132.

In embodiments with additional security layers, the drug manager 188 first selects a drug storage apparatus 102, 116, 132 from a list of connected and authorized drug storage apparatuses 102, 116, 132. For example, the drug manager 188 could read a serial number off the side of the storage unit 103, 117, 133 and type it correctly into the user interface 186 at the central server 180. Once the serial number or identification number of the drug storage apparatus 102, 116, 132 is entered, a display code is sent to the drug storage apparatus 102, 116, 132 in a "verification required" messages 170. In some embodiments, a display code could sent to any available user interface 106, 120, 130, 136, 142 associated to the drug storage apparatus 102, 116, 132. The drug manager 188 would then enter that exact same code into the user interface 186 at the central server 180 to confirm they are holding the exact same drug storage apparatus 102, 116, 132 that is known and currently being managed by the central server 180. In other embodiments, the verification code may be sent only to the user interface 106, 120, 136 associated directly with the storage unit 103, 117, 133 to ensure only the storage unit 103, 117, 133 receives the verification code and acts upon it.

The verification code might be one or more numbers, one or more letters, a combination of numbers and letters, a visual LED display sequence, or a series of tones and beeps. Each verification code is randomly selected by the central server 180 to ensure it cannot be guessed or anticipated. Once the drug manager 188 has entered the matching verification code. the central server 180 sends a confirmation message 170 back to the corresponding authenticated drug storage apparatus 102, 116, 132 to unlock the main compartment of the storage unit 103, 117, 133 so that packaged drugs 112, 126, 138 can be loaded.

Loading Detectable Drug Packaging

Once the storage unit 103, 117, 133 is unlocked, the drug manager 188 can load specially prepared detectable drug packaging 112, 126, 138. As discussed, there are several methods for packaging drugs for drug consumers 192, including individual blisters, multi-pack dispensers, packets, vials, canisters and others.

Locking the Storage Unit

Once a recognizable detectable drug packaging 112, 126, 138 unit is placed in the storage unit 103, 117, 133, the storage unit 103, 117, 133 sends a signal to the CPU 104, 118, 134 using the method described earlier, which depend on the design of the storage unit 103, 117, 133 to allow the closing and locking of the storage unit 103, 117, 133. Prior to this point in time the storage unit 103, 117, 133 might have been closed, but it would not have locked as the CPU 104, 118, 134 would not have received the "loaded" signal and would have not enabled the locking mechanism to engage.

Once confirmed and closed, the drug storage apparatus 102, 116, 132 sends a message 170 to the central server 180 to indicate it is closed and locked with specific detectable drug packaging 112, 126, 138 contained within. In some embodiments, the number of drugs in the detectable drug packaging 112, 126, 138 is not known. In those embodiments, the drug manager 188 will supply that information at the central server 180 through the user interface 186. In those embodiments where the number of drugs in the detectable drug packaging 112, 126, 138 is known, this information will be passed automatically to the central server 180.

Authorizing a Drug Consumer

Once the storage unit 103, 117, 133 is loaded, it is not able to perform any functions until a drug consumer 192 is authorized for drug extraction. There are several possible embodiments for storing and confirming the user-identity of the drug consumer 192. These embodiments were discussed earlier in the section discussing the user-identity input 110, 122, 144. To review, the drug consumer 192 may provide their user-identity through biometric inputs, a body scan of embedded sub-dermal user-identity chips, or using many other user-identity confirmation methods. All of these user-identity capture methods result in a secure "user-identity captured" message 170 being sent to the central server 180 confirming the drug consumer's 192 user-identity.

Drug Consumption Regimen

One of the responsibilities of the drug manager 188 is to establish a drug consumption regimen and dosing guidance regimen for the drug consumer 192. A set of parameters will be referred to as the "drug regimen". Usually, the frequency and timing of drug consumption, time gap between drug doses, optimal drug consumption, drug witnessing and other parameters are established by a trained professional, such as a doctor, pharmacist, nurse practitioner, a trained midwife, a specialist, or many others. This drug regimen information can then be input to the user interface 186 at the central server 180 related to the specific drug storage apparatus 102, 116, 132 assigned to that drug consumer 192. Subsequent figures will present several embodiments for this user interface.

In some embodiments, the drug consumer 192 themselves have entered this information to make use of the drug storage apparatus 102, 116, 132. Once the drug regimen is complete, the central server 180 creates secure regimen code files for download 170 to the communication device 108, 128, 140 of either the storage unit 103 or the drug consumer's computer 146, 148.

Drug regimen information may be input prior to authorizing a drug consumer 192 to use the drug storage apparatus 102, 116, 132. In some embodiments, as shown in FIG. 12, an external system has uploaded the drug regimen into the central server 180 for the drug consumer 192. In these embodiments the drug regimen can be used directly or further modified to refine the parameters for use by the drug consumer 192. For example, the uploaded drug regimen might prescribe taking a drug 4 times daily and the drug manager 188 might further refine the 4 dosing periods to specific times like 8:00 am, 12:00 μm, 5:00 μm and 9:00 μm.

After a drug consumer 192 is authorized to use the drug storage apparatus, 102, 116, 132, if drug regimen information has not yet been input, the central server 180 can prompt the drug manager 188 to complete this information to prepare the regimen encoded files for secure download 170 to the communication device 108, 128, 140 associated with the storage unit 103, 117, 133 for the drug consumer 192 whose user-identity was just captured and confirmed. At any time elements of the drug regimen could be modified, changed or refined with input from the drug consumer 192. For example, if a dosing time is set to 12:00 pm (noon) but the drug consumer 192 often must leave the house by 11:45 am to a special event, the time could be adjusted to 11:45 am each day.

In some embodiments, the drug storage apparatus 102 receives the regimen encoded files 170 via a communications device 108 located within the same physical housing as the user-identity input 110. In other embodiments, the information is relayed 124 from a communication device 128 to the drug storage apparatus 116 that contains a user-identity input 122. In other embodiments, the communication device 140 and the user-identity input 144 are both contained in a device, such as the drug consumer's computer 148, separate from the drug storage apparatus 132 and this device authorizes extraction of drugs.

In some embodiments the drug regimen is very restrictive, for example in the case of opioid agonist therapy drugs like methadone or buprenorphine. With these drugs the drug regimen might require the drug consumer 192 to be physically present on the phone with the drug manager 188 before the drug manager 188 issues a command at the central server 180 to release a single dose of drugs from the drug storage apparatus 102, 116, 132.

Initiating Drug Extraction

Once both the drug consumer's 192 user-identity has been confirmed through the "user-identity captured" message, and the regimen encoded files have been downloaded 170 to the communication device 108, 128, 140, drug extraction can commence according to the drug regimen encoded files. There can be a wide range of guidance in these encoded files including start date and time for drug extraction, daily dosing time periods, grace periods for late dosing, maximum time before doses are considered missed, and many others.

Ongoing Operation

Once dosing operations commence, the central server 180 receives drug consumption messages and other messages 170 from the drug storage apparatus 102, 116, 132 via the communication device 108, 128, 140. Drug consumption information is determined via triggering signals from the access detection computer circuit 150, 154, 164 used with the detectable drug packaging 112, 126, 138. These messages identify when the drug consumer 192 attempts to extract drugs from the detectable drug packaging 112, 126, 138. Other messages 170 can include "late dose" messages, "missed dose" messages "intrusion" messages, "drugs exhausted messages, and "battery low" messages, to name a few.

From the drug consumption messages 170, adherence tracking and drug compliance information can be calculated by the central server 180. Calculations can include simple taken versus not taken results based on the established drug regimen for that drug consumer 192. Embodiments can also include statistical analysis including standard deviation, (i.e. how far away from the optimal dosing time did the drug consumer 192 take their medication?), calculations in the area of probability projection calculations, (i.e. how likely is it that the drug consumer 192 will take their medications on time?), and advanced calculations based on data from multiple drug consumers 192, for example showing the normal distribution of drug consumption time deviation based on age, gender or some other selected criterion). Conforming to the drug regimen times and dose levels represent good adherence, failure to match the dosing times or dosing amounts leads to poor adherence.

In other embodiments where different types of drug regimen are established, for example 'as needed' (PRN), other types of analysis could be calculated. For example, there could be calculations to determine when a drug consumer 192 has had surgery, the maximum duration of pain mediation they will require in 90% of cases. Such calculations can improve patient outcomes, reduce excessive drug prescribing, and combat the risk of drug addiction which can occur with pain relief medications.

Authorizing Drug Monitors

As part of the central server's 180 user interface 186, the drug manager 188 can authorize drug monitoring entities 190, 194 to receive adherence information and other messages 198 from the central server 180. There are several possible embodiments for where and how these messages could be sent. In some embodiments, these message 198 may be email messages 198. In other embodiments, messages 198 can be sent via SMS to the cell phones of drug monitoring entities 190. In other embodiments, both email messages and SMS text messages 198 can be sent as configured by the drug manager 188. Other messaging options could be possible with proprietary message delivery equipment.

Authorized drug monitoring entities 190, 194 can include individuals such as doctors, pharmacists, caregivers and even the drug consumer 192 themselves to name a few. In some embodiments, the drug monitoring entity 194 could be a storage computer that collects all adherence data to create historical adherence data for review by related parties. This data can also be anonymized to provide trained professions information as to how to improve drug adherence. The data may also allow for the creation of historical statistical models representing the entire system.

The four illustrations FIG. 2A through FIG. 2D represent four different detailed views of a multi-pack drug blister pack 202 is augmented with an access detection computer circuit 204 to create detectable drug packaging 206. Although a gap is shown in the detectable drug packaging 206, the multi-pack blister pack 202 and access detection computer circuit 204 are brought together and merged.

Figure 2A:
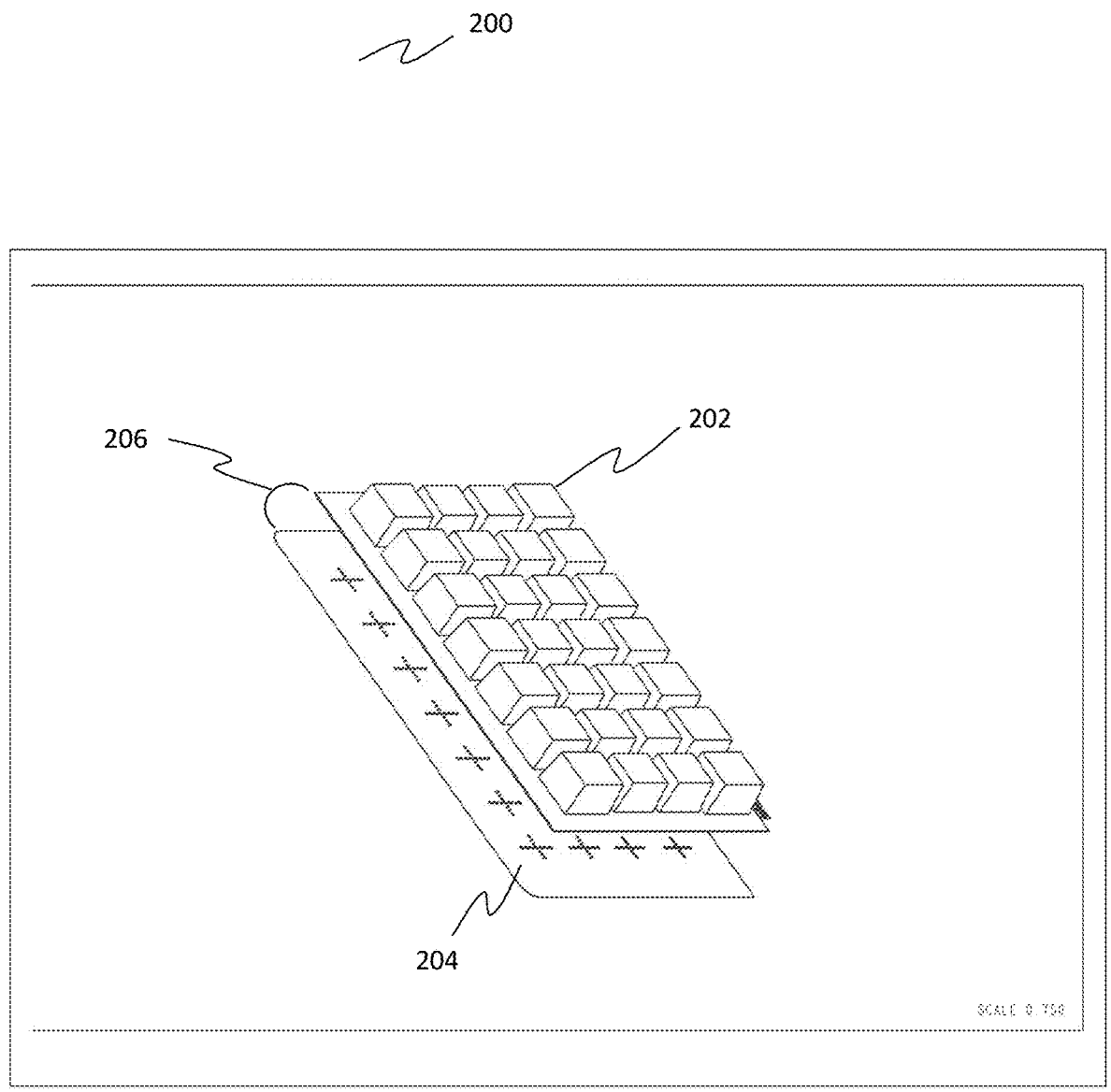
FIG. 2A shows an illustration of a multi-pack blister and an augmented access detection computer circuit.

FIG. 2A is close-up overview of a multi-pack blister 202 with an augmented access detection computer circuit 204. In this illustration, the particular images shows a 7×4 dosing blister 202 merged with a paper circuit 204 on the bottom of the blister 202. In this embodiment, the drug consumer 192 is given 4 doses per day for up to 7 days of drugs, for a total of 28 total doses. There are many configuration options for different numbers of does in a day and length of days supplied. For example, the drug consumer 192 might be given 2 doses per day, with 28 days of drugs provided or many other combinations.

Figure 2B:
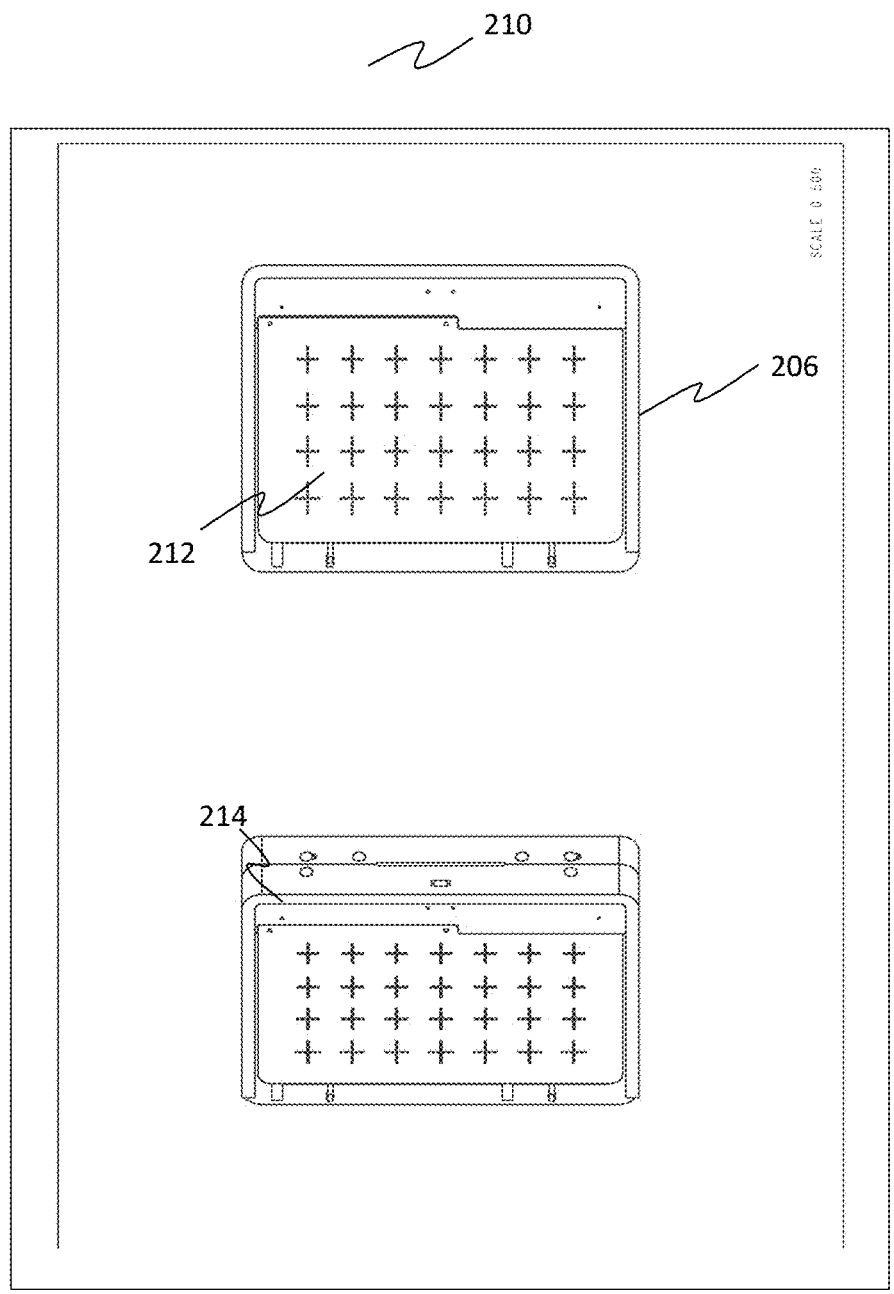
FIG. 2B shows an illustration of the multi-pack blister with the access detection computer circuit placed into a storage unit.

FIG. 2B shows an illustration 210 of the multi-pack blister 202 with an access detection computer circuit 204 so as to be turned into detectable drug packaging 206 and placed into a storage unit 214. In this embodiment, the top of the multi-pack blister 202 cannot be seen and can only be accessed through the top of the storage unit 214. On the bottom of the storage unit 214 all 28 slots are exposed for access. The illustration also showing 28 perforations 212 where drugs would be pushed through to extract them from the multi-pack blister container 202.

Figure 2C:
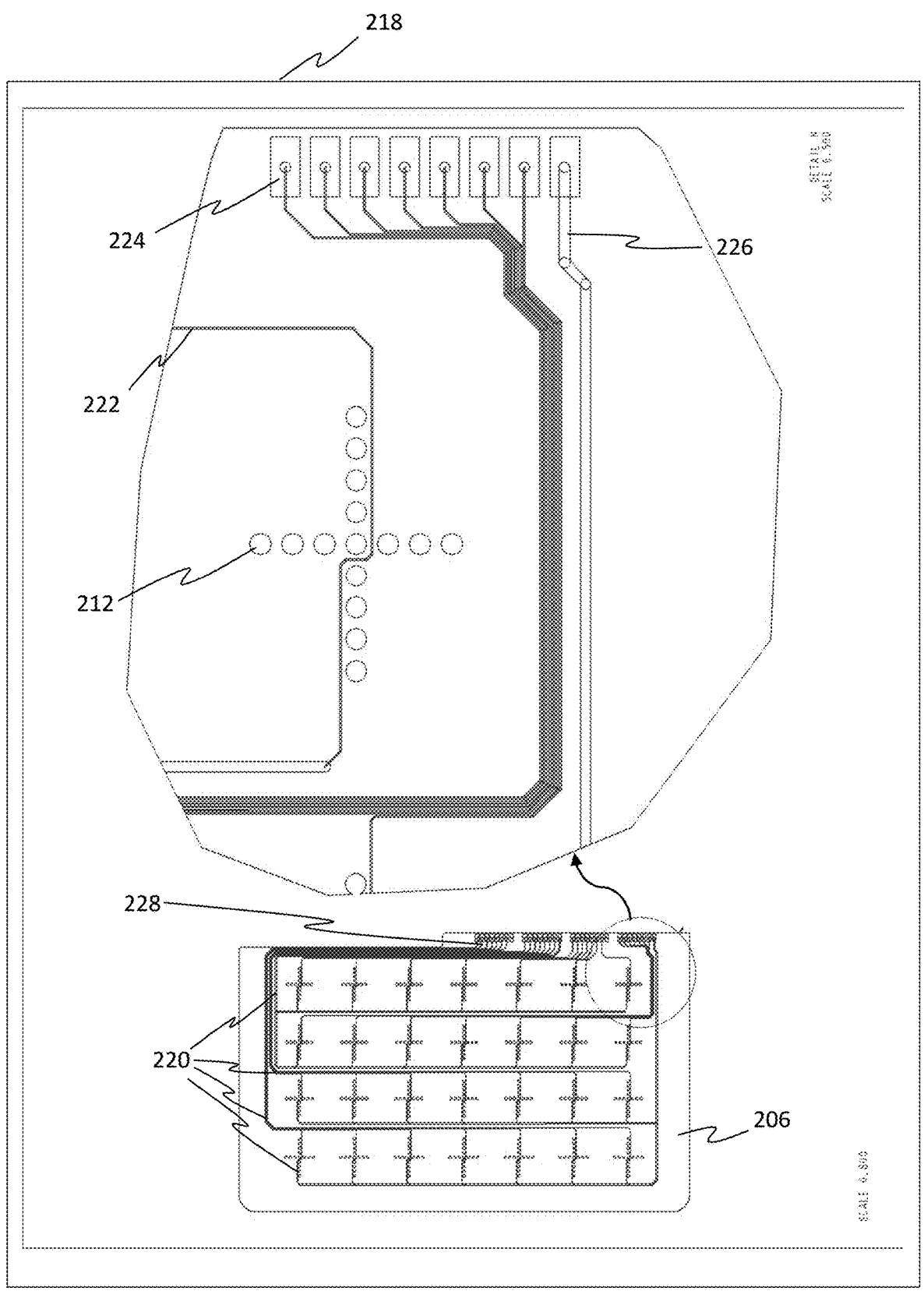
FIG. 2C shows an illustration of the computer circuit trace lines and a close-up of one individual trace running through the perforations of a single compartment.

FIG. 2C shows an illustration 218 of the computer circuit trace lines 220 and a close-up of one individual trace 222 running through the perforations 212 of a single compartment. In this embodiment, if the drug consumer 192 presses up, down or sideways on the packaging, the circuit trace 222 will be broken. The circuit trace 222 stops at a termination point 224 that is connected to a coupling point 228 (PCB). The coupling point 228 represents the connection point between the detectable drug packaging 206 and the CPU of the storage unit 214.

Once brought into proximity, electrical signals can pass from the CPU, through the PCB and into the circuit trace 222. Each of the trace lines 222 illustrated passes through one of the four daily doses (i.e. doses that are to be taken at a specific time of day), and trace lines 222 passing through the same daily dose are grouped together. These four groups of trace lines 220 connect in seven blocks of termination points 224 representing the seven days of the week. Each of the seven termination points 224 connect to the PCB using seven distinct coupling points to distinguish each day of the week from each other. Each of the four blocks of termination points 224, also has a shared ground trace 226 that is used to determine when one of the individual seven traces 222 if any of the group of trace lines 220 are broken.

As discussed previously in this embodiment 218, the doses for each of seven days of the week are in one of four groups 220, representing the four dosing periods in a single day. Accordingly, there are seven trace lines 222 in each of the groups 220 corresponding to the days of the week and forming a larger circuit that connects the trace lines for the same daily doses for each of the seven days of the week. Each trace line 222 in this larger then connects to the connector through its termination point 224. There are several possible embodiments for this connector 224, such as a through-hole connector, a spring connector, or another format suitable for manufacturing and dynamically coupling between the paper circuit and the PCB that holds the CPU.

Figure 2D:
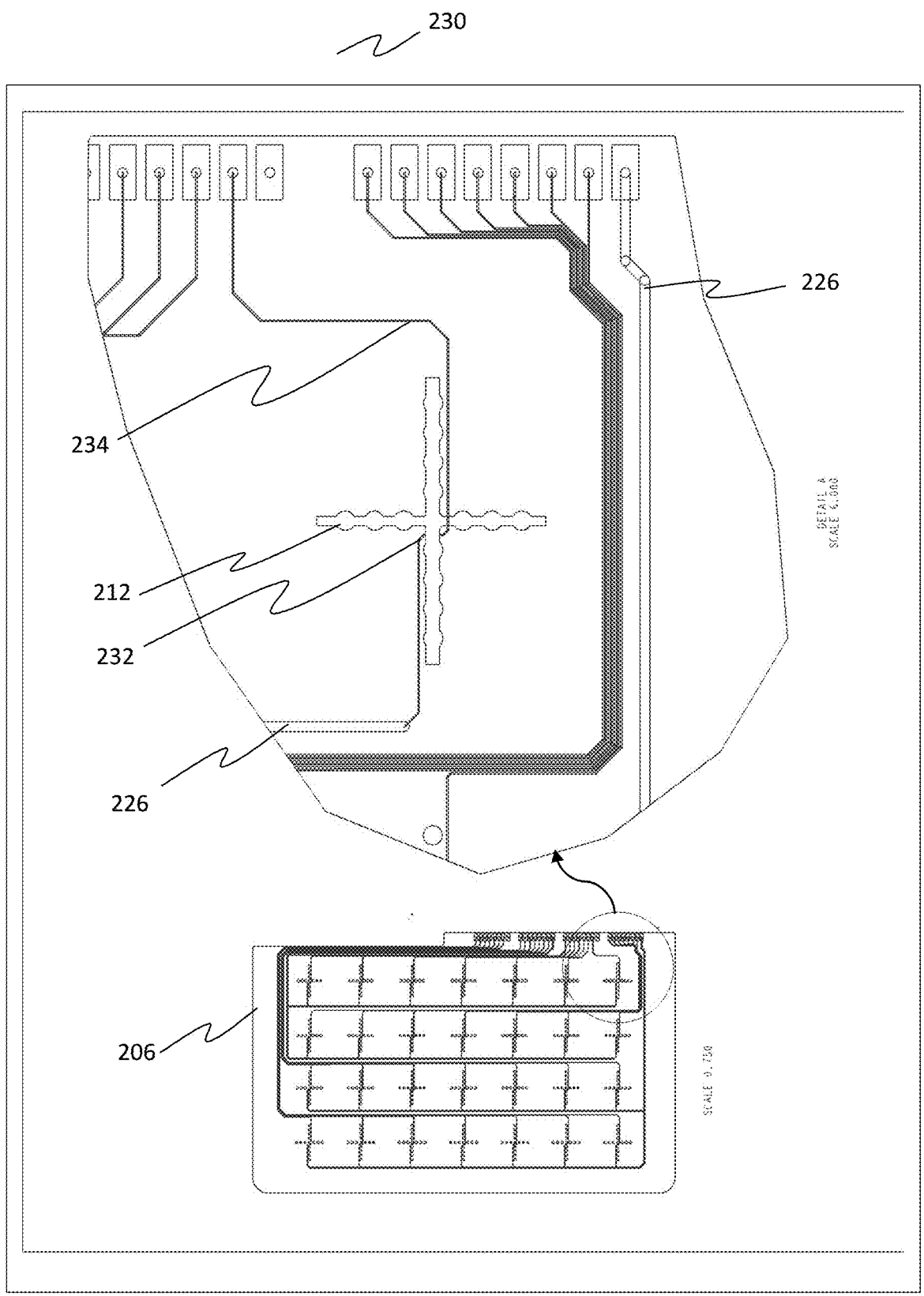
FIG. 2D shows an illustration of broken perforation where drugs have been extracted from the blister-pack.

FIG. 2D shows an illustration 230 of broken perforation 232 where drugs have been extracted from the blister-pack 202. There are many embodiments for how the paper circuit 204 could be utilized to detect which of the dosing slots have been accessed. In one embodiment, there is one shared ground trace 226 for each group of seven traces 220, corresponding to the seven column traces for each day of the week. When a drug consumer 192 breaks the perforation 232, there are two traces which no longer form a complete circuit: the ground trace 226 (which may still be connected in a complete circuit with other traces), and another trace 234 that connects to a termination point specific to that trace. The CPU then determines which perforation has been broken by performing a scan in which each trace in the group of 7 traces 220 by sending a pulse signal. If a trace is not broken, there is a direct path to ground and the CPU detects a "low" signal. If a trace is broken, there is no path to ground and the CPU detects a "high" signal. In this embodiment, the broken trace 232 will only give a "high" signal during a scan and will be left disconnected at all other times. This technique prevents a drug consumer 192 from dropping a metallic object into the box and connecting the trace after it is disconnected.

In this embodiment when the drug consumer 192 accesses the drug dose corresponding to a dose to be taken on Monday at breakfast, they will break the Monday circuit. With the storage unit open and actively dispensing drugs, the CPU scans each slot by pulsing the column traces 234 to determine whether any of them are broken. If a column trace 234 does not drop to ground, then the system knows that it is broken. Once detected, the CPU then sends a message back to the central server 180 to indicate which day or days of the week that the drug consumer has extracted drugs for. If more than one day of the week has been extracted, an alert message is added to the drug extraction message to warn the drug monitoring entities that an incorrect adherence pattern has been detected.

Figure 3:
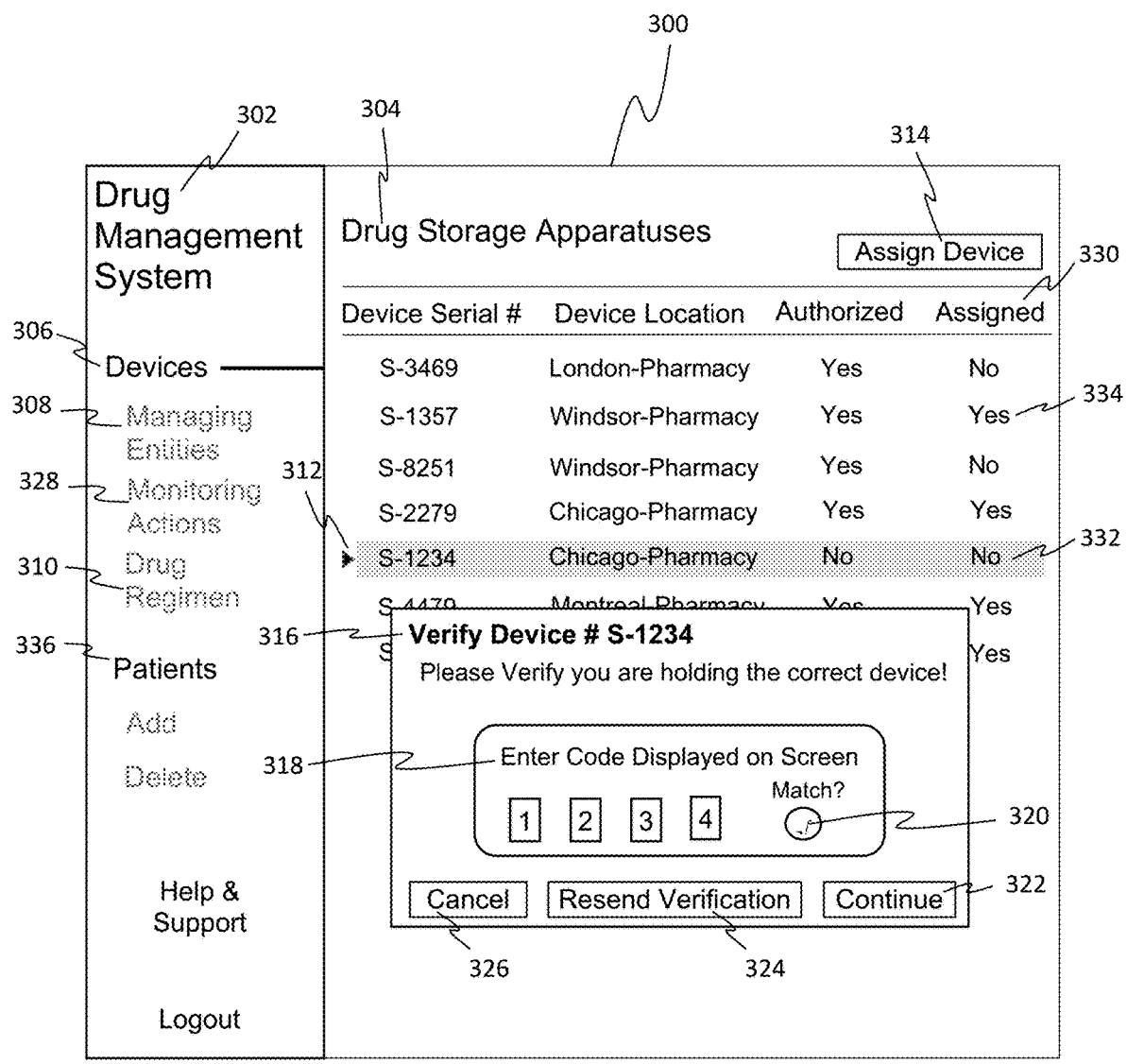
FIG. 3 shows an illustration of a user interface for a list of drug storage apparatuses at the central server.

Turning to FIG. 3 there is shown an illustration of a user interface (UI) 300 for a list of drug storage apparatuses at a central server 180. The drug management system 302 at the central server 180 represents one example embodiment for different UIs that could be built using advanced screens, graphics, options, and choices for a drug manager 188. This UI 300 is built for an authorized drug manager 188 that intends to work with drug storage apparatuses for the purpose of assigning them to a drug consumer 192 ("Patients" 336 in this illustration) for the eventual extraction and consumption of packaged drugs.

In some embodiments, the drug manager 188 is a professional such as a doctor, pharmacist, nurse practitioner, nursing home worker, or another type of individual in authority over a drug consumer 192. In other embodiments, the drug manager 188 is also the drug consumer 192 and they are using the system to ensure they are adherent to drug consumption requirements or protecting their own drug supply from others, like their children that might take or consume their parent's drugs.

In this illustration, the drug manager 188 is presented with a navigation bar 302 on the left side of their UI 300. They can initially only select a devices menu 306 as the Managing Entities menu 308, Monitoring Actions menu 326 and the Drug Regimen menu 310 are disabled until a specific drug storage apparatus 312 has been selected.

Once the drug manager 188 selects the devices menu 306, they are presented with a list of known drug storage apparatuses 304. A header 330 for the list of drug storage apparatuses 304 indicates the different characteristics for the drug storage apparatuses that are displayed in the list 304. Different characteristics 330 may be displayed in different embodiments. In this embodiment, the list 304 displays a device serial #, a device location, an authorized setting, and an assigned setting, as indicated by the header 330. Using this information and the identification on the storage unit they are holding, the drug manager 188 can navigate to a specific drug storage apparatus 312 they would like to assign. They can only take charge of a specific drug storage apparatus 312 if its Assigned Value is "No" 332 and therefore is not currently being used by another drug consumer 192. An Assigned Value of Yes 334 implies the drug storage apparatus has already been assigned to another patient and could be in active use.

By selecting the "Assign Device" 314 menu button, the drug manager 188 can attempt to take charge of the drug storage apparatus 312. In some embodiments, the drug manager 188 will have to prove they are holding the storage unit in their hands. In these embodiments, a "Verify Device" 316 modal dialogue box 316 will is presented to the drug manager 188 to verify the physical device. The drug manager 188 must then enter the code displayed on the UI screen of the drug storage apparatus in the designated field 318. This code would first be sent from the central server 180 to the storage unit for display on the UI for several seconds. If the drug manager 188 enters the correct code, the "matched confirmation" button 320 is checked to indicate they were successful. They can then select "Continue" 322 to proceed to the next step or they could resend the verification code 324 to try again if they got the answer wrong. If they have the wrong machine or want to terminate the processes of assignment, they can select Cancel 326 to exit the verify device 316 modal dialogue box.

In other embodiments the storage unit might have an affixed bar code that can be scanned with a scanner. It might have an embedded RFID identification code or some other automatic identification detection method. In these embodiments, the device verification step 316 may not be required, but a scan of the storage unit's external bar identification code or QR code could be used to verify the device. Once assignment is completed, the drug manager 188 will be able to select a patient (drug consumer) to be assigned to the drug storage apparatus selected 312.

Figure 4:
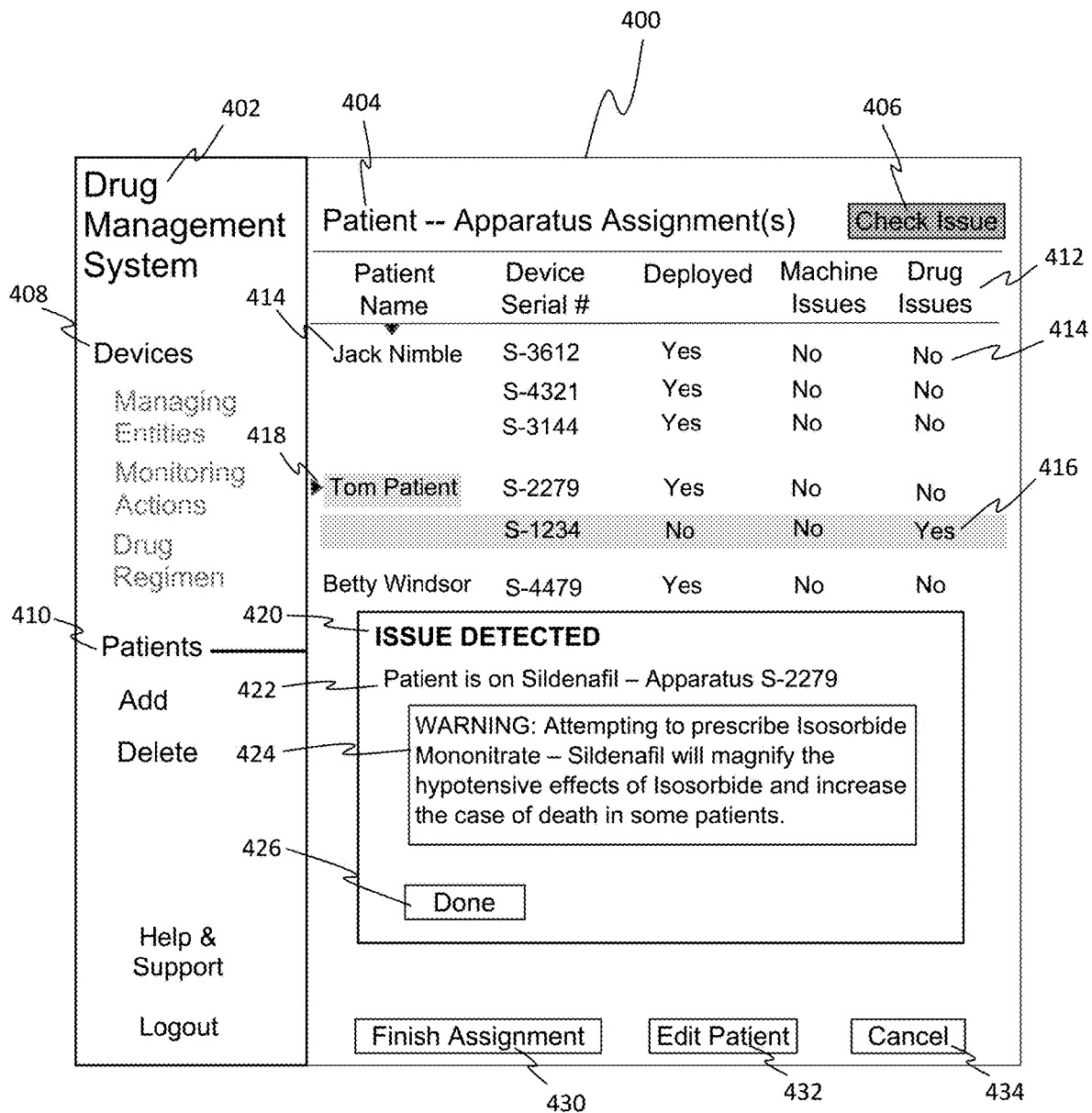
FIG. 4 shows an illustration of a user interface for listing and assigning patients to drug storage apparatuses at the central server.

Turning to FIG. 4 there is an illustration of a user interface 400 for listing and assigning patients to drug storage apparatuses at the central server 180. This listing and assigning user interface (UI) at the central server 180 represents one example embodiment for different UIs that could be built using advanced screens, graphics, options, and choices for a drug manager 188. This UI 400 is built for an authorized drug manager 188 that intends to assign a patient to a selected drug storage apparatus. In this example, this patient UI menu 410 has been entered by first staring in the Devices UI menu 408. For other purposes this patient UI menu choice 410 can also be entered directly for listing patients, adding new patients, editing patient information and deleting patients.

This UI 400 is able to show both patients with active apparatus assignments 404 and patients with no active apparatus assignments. The list 414 of patients might be sorted by placing those with assigned drug storage apparatuses first and those without assigned drug storage apparatuses second. The list of patients provides a title of different fields 412 that are included for the drug manager's 188 convenience. In other embodiments there could be additional fields 412 like the patient's gender, data of birth, health card identification numbers and many other fields.

In this embodiment the drug manager 188 has selected Tom Patient 418 for the assignment of drug storage apparatus with serial number S-1234. In some embodiments each time drugs are placed into a drug storage apparatus like S-1234, the barcode is scanned on the packaging and given to the central server 180. In other embodiments the drug manager 188 might input the drugs that are to be dispensed from the drug storage apparatus. In other embodiments the types of drugs within the packaging is shared between Pharmacy Management Software (PMS) to the central server 180. This embodiment is highlighted in FIG. 13.

In those embodiments where the central server 180 has information about the types of drugs within the drug storage apparatus, the drug manager 188 can perform advanced checking on drug interactions and other issues. By selecting the 'Check Issue' 406 button the drug manager 188 can verify if the assignment has any conflicts or concerns with other drug storage apparatuses already assigned. In this case a drug issue 416 has been detected and a warning modal box 420 has detected an issue. In this example, the patient Tom Patient 418 already has a drug storage apparatus S-2279 assigned to them with the drug Sildenafil 422. The new drug storage apparatus S-1234 being assigned contains the drug Isosorbide, which has known drug interactions with Sildenafil 424. However, the known issues are for patients with additional risk factors like obesity, hypertension and cigarette smokers. Therefore, if the drug manager 188 these secondary issues are not present, they can select Done 426 and return to the assignment screen to complete the process.

When they return the drug manger 188 can choose to Finish the Assignment 430, Edit the selected Patient 432 or Cancel 434 the process. Perhaps learning about the drug interactions 420 has raised their concern enough to talk to the patient and the original doctor who prescribed the drug.

At any time a drug manager 188 can enter the patient 410 area or select the Add or Delete button to add or remove patients from the system. They can also enter the patient area to see if a given patient is having a Machine Issue 412. For example, perhaps the drug storage apparatus is running out of batter power and the drug consumer 192 is failing to plug it in for recharging. Other situations like excessive failures to confirm the user-identity might be occurring and changes are needed there. There could also be a drug storage apparatus failure of one of the mechanical sub-systems. These types of errors can be displayed and examined in this area.

Figure 5:
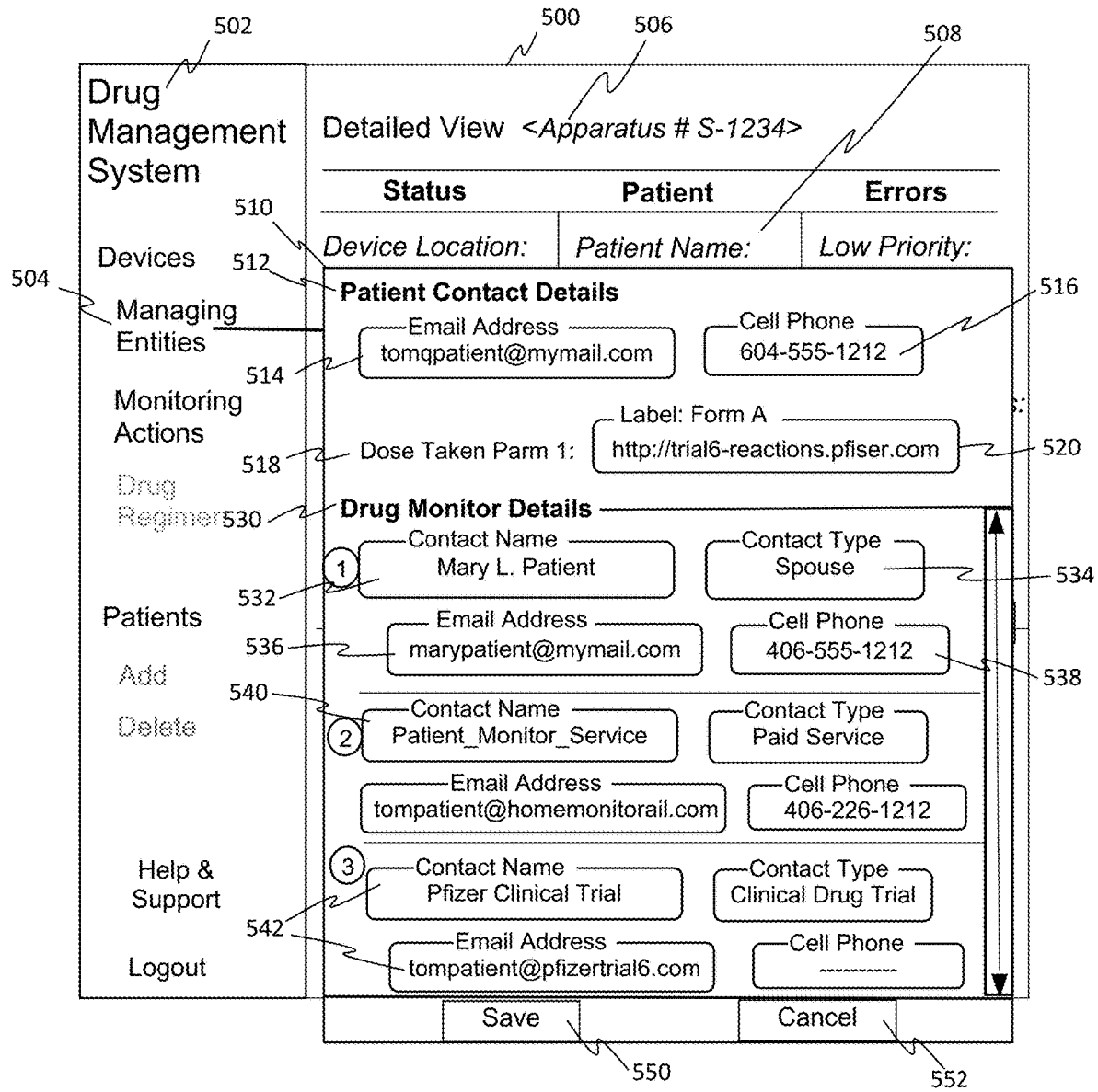
FIG. 5 shows an illustration of a user interface for inputting managing entities at the central server.

Turning to FIG. 5 there is an illustration of a user interface 500 for inputting managing entities 190, 194 at the central server 180. The detailed view of one drug storage apparatus 506 at the central server 180 represents one example embodiment for different UIs that could be built using advanced screens, graphics, options, and choices for a drug manager 188. In this example, a drug manager 188 has taken charge of an unassigned drug storage apparatus 506, they have assigned a patient and are now looking at a detailed view of the drug storage apparatus state 508.

Figure 6:
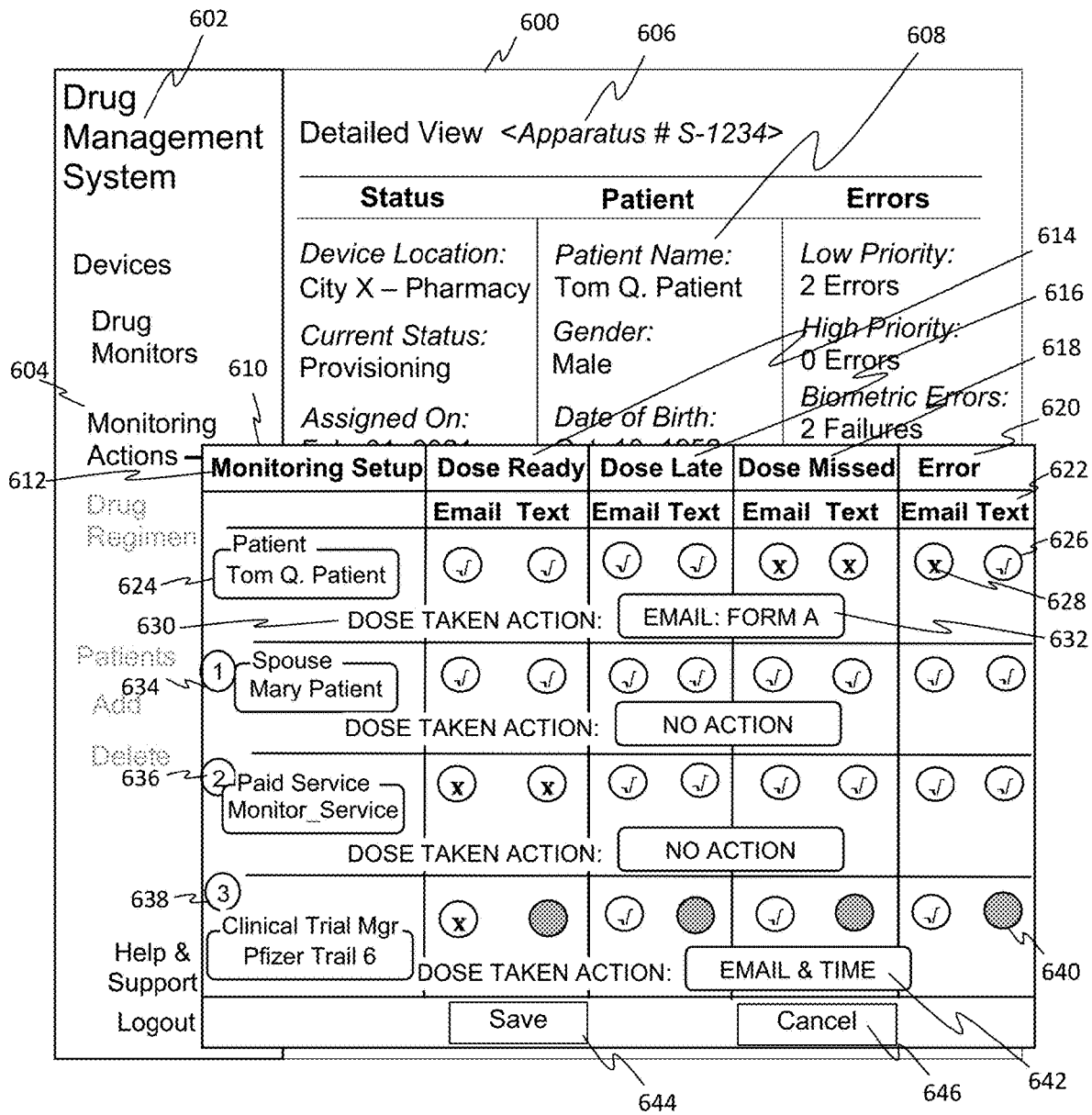
FIG. 6 shows an illustration of a user interface for selecting the monitoring actions for a defined patient and managing entities at the central server.

The data display area 508 provides the status of the drug storage apparatus, the patient identification and any errors that have occurred. Although obscured in this illustration, FIG. 6 provides greater detail of the detailed assignment area 508. There are many embodiments of information that could be presented, these choices represent a small subset for this illustration.

By selecting the Managing Entities menu 504, the drug manager 188 is presented with a modal dialogue box 510 allowing them to enter a wide range of information for patient contact information 512 and drug monitoring details 530. In this area, the managing entities 504 can be provided, including contact information for the drug consumer (patient) 514, 516. The drug consumer 192 themselves might also want to receive different types of notifications about their drug storage apparatus 506. This could be useful if they are not in the presence of the drug storage apparatus 506 and were looking for reminders about when to consumer their drug doses. These selections are highlighted in FIG. 6.

In this example, entering an email address 514 and a cell phone 516 for the patient allows them to request the reception of email alerts and alarms. Entering a cell phone 516 for the patient allows them to request the reception of SMS text messages for alerts and alarms.

In some embodiments the drug manager 188 can enter steps to be performed when a drug dose is taken 518. This is one example of the central server 180 triggering actions based on events happening in the drug storage apparatus. There can be a wide range of options in this area. In this example, a parameter 1 is defined 518 that is a form 520 that can be sent when a drug dose is taken 518. The form is labeled 'Form A' and this label can be used when setting up Notifications, as illustrated in FIG. 6. For example, this form could be created as part of a clinical drug trial being established by a large drug manufacture, e.g. Pfizer. The form might be sent to the patient when they take the drug dose to see what drug reactions they have had. Another form, not shown in this example, could be sent to a caregiver to record any external reactions a patient is having with a drug as observed by a third party. For example, they could be disoriented, agitated or confused, which the drug consumer 192 themselves might not be able to recognize.

In another embodiment there could be a last dose taken trigger configured. In this embodiment, the Label: might point a backup storage device identifier that is used to store 'extra' drug packaging. When the drug storage apparatus is empty a trigger could then be sent to a known backup storage device used for holding extra drugs safely until needed.

As an example, if a drug consumer takes a particular drug, an alert could be sent to a device to trigger an action relating to the form to input information about how the drug consumer is feeling. For clinical trials, the form may be collect trial related data. The alert can also be transmitted to other devices. An alert can be transmitted to a blood pressure device (or mobile device) to capture data for blood pressure within a time period of taking a drug dose.

In this example the form will be presented by an internet HTTP link defined as: "http://trial6-reactions.pfiser.com". In other example the form could be stored at the central server 180 in the form of an Adobe PDF file and be emailed directly to the drug consumer 192. In other embodiments the form could already be stored at the drug storage apparatus and be presented to the user when an email or SMS text message is received.

Additional configuration values can also be entered for drug monitoring entities 530. In this example, the drug manager 188 is able to enter 1 or more drug monitors 530 that act like caregivers for the drug consumer 192. In this way different management and support strategies can be created when supporting high-risk drug consumers 192 and clinical drug trial participants.

Each drug monitor added in this section 530 involves providing a drug monitor name 532, a contact type 534, an email address 536 and a cell phone number 538. The contact type 522 might indicate many different relationships to the drug consumer 192, such as doctor, pharmacist, spouse, child, loved one, paid service, clinical drug trial manager or many others. By entering an email address 536 for a drug monitor 532, the drug consumer 192 would then be able to request that drug storage apparatus 506 alerts and alarms be sent by email to that drug monitor 532. By entering a cell phone number 538, the drug consumer 192 can then request alerts and alarms be sent by SMS text messages to that drug monitor 532.

In other embodiments other type of messages could be sent. For example, a specific social media identifier may be provided and the central server 180 could send a message to a social media address. For example, with a Facebook username provided for the address of a drug monitor 532, it would be possible to send Facebook Messenger™ messages to the drug monitor 532. Although just three drug monitors shown in this section 530, there could be many more and with a scroll bar provided to see and edit them all.

In some embodiments the use of the system to support a clinical drug trial solves many known challenges when running a clinical drug trail. The system is able to provide biometric and user-identity confirmation of drug consumption, which is extremely valuable in a clinical drug trial. In this example the Pfizer clinical trial 542 number 6 is using the drug storage apparatus for feedback and for tracking exact drug consumption. By include a form to be filled out 520, additional information can be provided to support the drug trial requirements.

When complete the drug manager 188 can save the configuration 550 or cancel the configuration 552 if they run into problems. For example, they might be editing an existing set of Drug Monitor Details 530 and failed to acquire the necessary email address information or cell phone information.

Turning to FIG. 6 there is an illustration of a user interface 600 for selecting the monitoring and trigger actions for the defined patient and managing entities at the central server 180. The detailed view of one drug storage apparatus 606, and the method used to present the monitoring setup at the central server 180 represents one example embodiment for different UIs that could be built using advanced screens, graphics, options, and choices for a drug manager 188.

In this example, the drug manager 188 has taken charge of a drug storage apparatus 604, has defined drug monitors, and is now defining Monitoring Actions 604 for those drug monitors. As mentioned in FIG. 5, the detailed view of the drug storage apparatus S-1234 is shown 608 below the modal dialogue box 610.

The first part of the main screen shows a status area 608, which provides the authorization date, assignment date and the operational status for the drug storage apparatus 606. This drug storage apparatus 606 has a status of "Provisioning", which means it is not operating yet and the drug manager 188 has additional required steps before it can start dispensing drugs.

Figure 7:
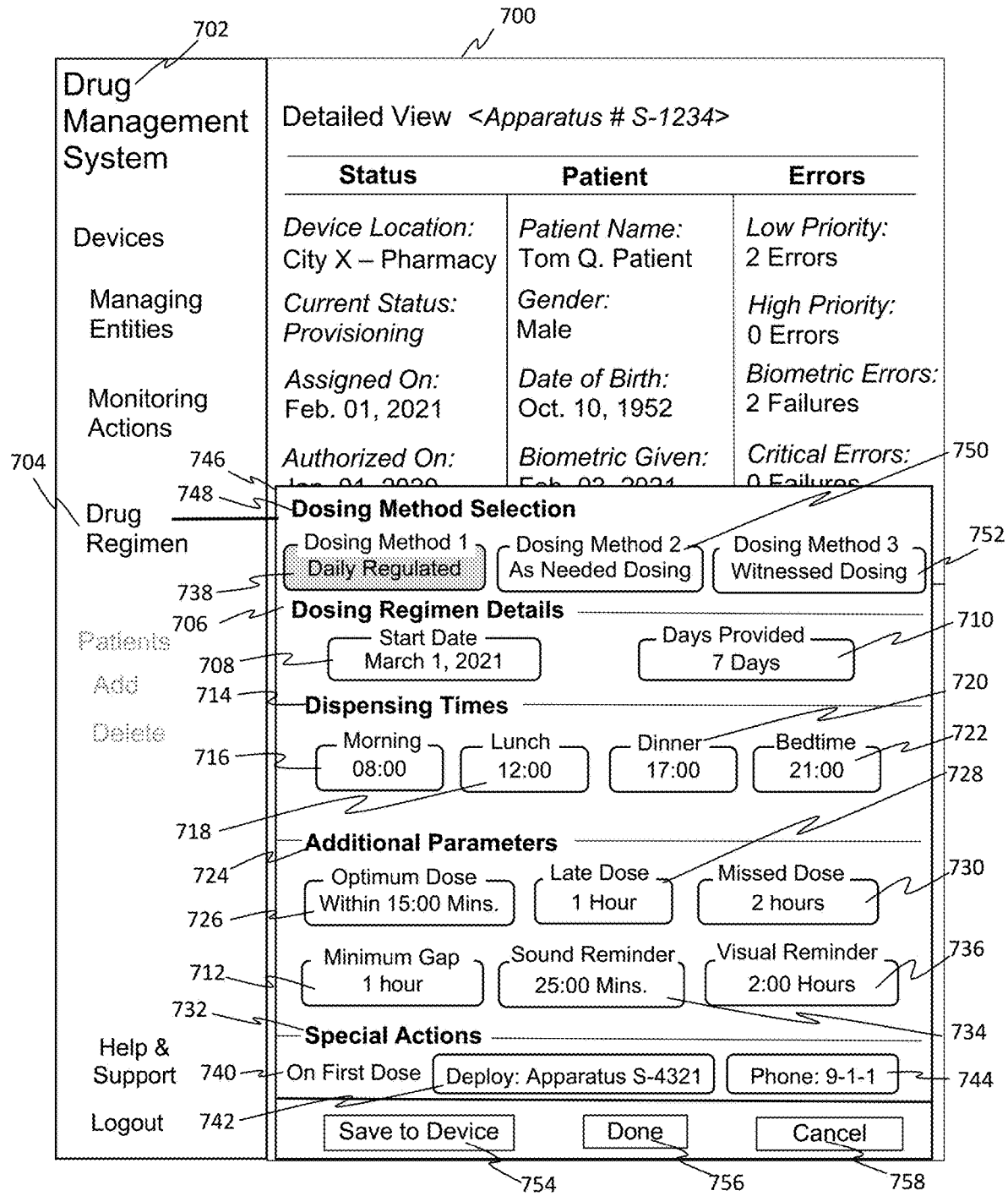
FIG. 7 shows an illustration of a user interface for defining a dosing regimen for a drug consumer.

The patient area shows the name of the patient (drug consumer 192), their gender, date of birth and if a biometric has been provided to the drug storage apparatus 608 yet (shown in FIG. 7).

The Errors area shows that 2 Low Priority errors, no High Priority errors and 2 biometric errors have occurred. Based on this information, it may be the case that during the registering of the drug consumer's 192 biometric information there were 2 minor errors that occurred in taking this information. For example, if a fingerprint biometric was being provided, they may have inadvertently moved, and several attempts were needed to acquire their fingerprint.

By selecting the monitoring actions menu 604 on the left menu within the drug management system section 602, a modal dialogue box 610 is presented. The modal box 610 represents the monitoring setup choices which are based on the earlier definition of drug monitors. The modal box 610 shows a header with three different message categories.

In this embodiment, these categories or triggers are for Dose Ready 614 messages, Dose Late 616 messages, Dose Missed 618 messages and Error 620 messages. In other embodiment there could be fewer categories or more categories. For example, there could be categories just focusing on late doses, battery and power issues, biometric input errors, and intrusion attempts. These and many other embodiments would be possible.

In this embodiment, several of the triggering actions 622 cause an email or text message to be sent to a defined patient or monitor. In other embodiments these trigger events 622 could also cause secondary drug storage apparatus to begin a deploying cycle and start dispensing drugs or other similar actions. In the case of dose taken 630, there is an example of another type of trigger action that causes a form to be sent to the patient so they can fill out information about the drug they just consumed.

In this example, the trigger action for the Dose Taken Action 630 is defined for each Drug Monitor 624, 634, 638. In this area a special action can be performed when the drug consumer 192 takes a dose of drugs as prescribed. In this example, when the Patient Tom Q. Patient 624 takes a drug dose 630 they will be emailed Form A 632 as defined by the previous configuration for drug monitors (FIG. 5).

In this example embodiment, the first category for dose ready 614 shows an example of sending notifications for when a given dose on a specific day is available for extraction. The patient 624 (drug consumer 192) may want to know where their dose is ready 614 for extraction, making this a useful feature. A positive selection is represented by a checkmark 626 in the button that lines up with the menu 614. In this example the patient's spouse 634 also wants to know when doses are ready for exaction from the drug storage apparatus. Although the patient 624 and spouse 634 want this notification, the paid monitoring service 636 and Clinical Trial Mgr (Manager) 638 do not want to be bothered by dose ready 614 notifications. To turn off the notification, the drug manager 188 selects an 'X' in the button 628 that lines up with the menu 614.

The next category is for dose late 616 indicating that if the drug consumer 192 has not taken their dose within a certain configured length of time after it is due, it is considered late. This message is perfect for patients and caregivers to help remind them that the dose is still pending. In each row for a given category, the drug manager provides a checkmark 626 below the Email Title 622 will mean that Patient or Drug Monitor would like that form of message indication. Placing a checkmark 626 below the Text Title 622 will indicate that the Patient or Drug Monitor would like that form of message indication.

The next category for dose missed 618 represents an alert drugs monitors, including the patient that a dose has been missed. In this example, the patient 624 does not want to know if they have missed a dose, but every other monitor 634, 636, 638 does want to know. If a given monitor 634, 636, 638 does not have a defined email or cell phone, the radio button is displayed in grey 640, indicating that no action can be taken for this area (email or cell phone action).

The next category defines what should happen if an Error 620 occurs on the drug storage apparatus 606. Finally, the actions related to Dose Taken Action 630 are defined for the Patient 624 and each Drug Monitor 634, 636, 638. In this example the Patient 624 receives an email containing an HTTP linked defined as Form A 632. The only other action is an Email and Dose Taken Time that is sent to the Clinical Trial Mgr.

Once the drug manager 188 has made all the necessary or desired selection choices, they can select the Save button 644 to save their work and return to the detailed view 604. Otherwise if they run into a problem or do not like their selections they can Cancel 646 to return to the detailed view 604.

Turning to FIG. 7 there is an illustration of a user interface 700 for defining a dosing regimen for a drug consumer 192. The detailed view of one drug storage apparatus, and the method used to present the dosing regimen details at the central server 180, represents one example embodiment for different UIs that could be built using advanced screens, graphics, options, and choices for a drug manager 188. In this example, the drug manager 188 has taken charge of a drug storage apparatus, has assigned a patient, and has now selected the drug regimen 704 side-bar menu item in the drug management system 702.

By selecting the drug regimen menu 704, a modal dialogue box 746 appears that shows drug dosing regimen details. There are many embodiments for the type and number of configuration choices that can be provided. This subset is presented to illustrate a good subset of choices that are easily understood and explained in this embodiment.

The first option in this modal box allows for the drug manager to make a Dosing Method Selection 748. The Dosing Method Selection 748 allows for different regimens to be established by the drug manager 188 that best suits the drug consumer 192 or that has been prescribed by a professional, like a doctor, dentist, nurse practitioner or other drug prescriber. The first illustrated Dosing Method 1 748 is for a Daily Regulated dosing method 738. The Daily Regulated method 738 sets up one or more daily times when the drug consumer 192 can extract drugs from the drug storage apparatus. In this illustration this method is shown as grey because it has been selected by the drug manager 188.

The second dosing method illustrated is the As Needed Dosing method 750. The As Needed Dosing method 750 would allow a drug consumer 192 to extract drugs as required to manage a specific health issue. One common affliction that uses this As Needed Dosing method 750 is for managing pain after a surgery or other serious condition. A different set of parameters would be presented in the lower section if this was selected by the drug manager 188. Certainly, the Minimum Gap 712 would be present as well as other potential parameters.

The final dosing method illustrated is the Witnessed Dosing method 752. This method might be used for specialized drugs, extremely costly drugs or drugs being taken for substance abuse. This method would limit the extraction of drugs to be triggered directly from the user interface. The additional parameters might be a button that simply states: 'Release One Dose'. A drug manager 188 might have to be on a voice call with the drug consumer 192 or even video call with the drug consumer 192 before making the decision to press the 'Release One Dose' button. Once on the call or video with the drug consumer, they can then enable the release of the drug and if desired watch the drug consumer placed the drug on their tongue and swallow the drug.

The next configuration item in this modal box 746 follows the selected dosing method highlighted in the Dosing Method Selection 748 and is called the Dosing Regimen Details 706. In this illustration the Daily Regulated method 738 has been selected. By selecting the Daily Regulated method 738 the drug manager 188 will be allowed to set the Dosing Start Date 708 for when daily dosing will commence. The Dosing Start Date 708 would normally be in the future from today's date. Since the deployment requires several more steps, including confirming the user's identity has been captured, this would allow time for these steps to take place. Also provided in this first section 706 is the duration of drug supply provided 710. The number of days provided 710 is calculated by the drug manager 188 to be the number of Dispensing Times 714, by the number of days. This guides the drug manager 188 when loading the packed drugs to ensure the full configured number of days are present.

The next section provides choices for drug dispensing times 714. In this example the there are four dosing times illustrated 716, 718, 720, 722. In other embodiments there could be a single dosing time each day, two dosing times a day or some other number of dosing times. This example allows the setting of a time for the morning dose 716, currently shown as 08:00 on a 24-hour clock. The second dosing time 718 shown in the lunch dosing time and it is set to 12:00. The first dosing time 720 is the dinner dosing time and it is set to 17:00. Finally, the fourth dosing time 722 illustrated is the bedtime dosing time and it is set to 21:00.

The value of setting dosing times for a drug prescriber, for example like a physician or some other trained professional, is that they know exactly when a patient should be taking their drugs and the effectiveness of the drugs when taken at specific times. This can also extend to the minimum gap interval 732 between doses to avoid complications and drug interactions. The final section 724 allows a drug prescriber or drug dispenser to future customize and tailor the dosing requirements of the drugs and the patients.

In some embodiments a Dispensing Time 714 could be left blank and the drug storage apparatus would simply skip that dispensing time 714. For example, some drug consumers 192 might only take three doses of drugs per day, but the packaging the drugs are supplied in contains pouches for four dispensing times 714. Therefore, by setting one time slot to blank the drug storage apparatus knowns to skip that dispensing pouch.

The next section illustrated in this figure is the additional parameters 724 area. This allows for finer levels of control and reporting as dosing takes place by a drug consumer 192. There are many possible parameters that could be provided for different embodiments. For example, parameters not illustrated may include dosing for as-needed dosing (PRN dosing). Such dosing can be used for pain medication and pain management.

The first parameter in this section 724, allows for the fine tuning of when the optimum dosing period 726 would be. When taking strong drugs, addictive drugs, or drugs that can interact with each other, there could be an optimum time after drug consumption is allowed when taking the drugs works best. Setting this parameter would also allow for better statistical analysis of how the patient is doing and how the drugs are affecting them. Setting this parameter indicates how long after the dosing time 716, 718, 720, 722 when the drug consumer 192 might be given a reminder to take their waiting drug dose.

The next example in this section 724 is the late dose indication value 728. This parameter allows the drug manager 188 to define an elapsed time after the dosing time 716, 718, 720, 722 when a late drug alert is sent to all monitoring entities that have been configured to receive alerts. In some embodiments, the drug consumer 192 themselves may also receive the late drug alert given its importance. In this example, the message would indicate that the drug consumer 192 is one hour late in taking their drug dose. In some situations, waiting one hour to take an important drug could be serious and even life threatening.

The next parameter is for determining when a dose is considered missed 730. In this embodiment, the value is set to two hours of elapsed time after the configured dosing times 716, 718, 720, 722. In other embodiments, the value could be set to 0, indicating that a dose is never considered missed. In some embodiments, the missed dose might be the same as the late dose value. In other embodiments a missed dose might occur only when the next dose time is reached. For example, a drug consumer 192 could be potentially so late in taking their 12:00 lunch dose 718 they reach their 5:00 pm dinner dose 720 before consuming their lunch dose 718. By setting the Missed Dose 730 parameter to 0 might result in this situation being considered a missed drug dose situation. In the case of a late dose, an alarm may be sent to all defined monitoring entities to inform them that a serious adherence issue has been detected. This configuration value combined with the late dose 728 configuration can also help to establish additional parameters for statistical analysis of drug consumption patterns.

The next parameters shown in this section 724 are to control the minimum dosing gap 726, and the durations of the sound reminders 732 and visual reminders 734. The minimum dosing gap 726 is the minimum time required between doses. For example, if a drug consumer 192 delays their 8:00 am morning dose 716 until 10:30 and the minimum dose gap is 2 hours, they will not be able to have their lunchtime dose until 12:30 pm, even if their lunchtime does is scheduled for 12:00 pm. This would be 30 minutes later than they would normally be allowed to take that 12:00 pm dose, however, adequate time gaps between doses may be necessary to ensure there is no interaction between drug doses and it may be more important to maintain spacing between doses than to ensure strict compliance with scheduled dosing times. Depending on the drugs being taken by the drug consumer 192, this may be a very important parameter to protect the drug consumer 192.

By changing the sound reminder 734 or visual reminder durations 736 the drug manager 188 can lengthen or shorten certain audio and visual reminders for the drug consumer 192. Once all the necessary parameters have been set the drug manager 188 can save the parameters 738 to the drug storage apparatus.

The final configuration section is for Special Actions 732. In some embodiments this UI section could be used when particular control is needed in the system. There can be different types of Special Actions 732 that are possible beyond the two examples that are illustrated in FIG. 7. These Special Actions 732 can be extended in many ways in other embodiments. This is where trigger actions can also be added if certain events take place within or around the drug storage apparatus. Trigger actions can be defined for On First Dose, On Last Dose, On Missed Dose, On Device Failure, On Device Intrusion Detected and many others.

The first example is an action called On First Dose 740. On First Dose 740 can be used to define an action if a drug consumer 192 decides to take a first dose from the drug storage apparatus. For example, some drugs are so demanding on a drug consumer's system that a second drug will be immediately required 742. A drug like bronchodilator (like Salbutamol) if taken for an asthma attack will require the patient to take corticosteroid (like Fluticasone). In another example, a patient taking Demerol for pain might immediately cause a drug dispensing apparatus 742 holding an anti-nauseant like Ondansetron or Metoclopramide.

The Special Actions 732 can be implemented by dosing files or code with control instructions to implement dosing regimes for drug dispensing apparatus 742 and transmit control commands between multiple devices. The dosing files and code can configure parameters to control the dispensing process, and coordinate operations between multiple components.

As an example for Special Actions 732, if medication is taken in one type or form of packaging, the code can trigger an alert for a second medication in a different type of packaging to be released. As a further example for Special Actions 732, if a particular medication is taken, the code can trigger an alert for a second medication to be taken by a defined period of time, which may be promptly after the initial medication is taken or a delay from that period. The other medication can be dispensed by the same drug dispensing apparatus 742 or a different drug dispensing apparatus 742.

As another example for Special Actions 732, if certain medication is taken then the code can automatically trigger a call to an emergency system such as 911. For example, drugs such as naloxone or nitroglycerin can automatically trigger a call to an emergency system. Access to these drugs may not be limited by user identity or fingerprints. For example, a proxy agent can access the drugs.

As a further example for Special Actions 732, if a medication dose is not taken, then the code can trigger an alert or provide access to take different medication. For example, if a medication dose for acetaminophen or oxycodone is not taken for pain, then the control code can enable access to acetaminophen or codeine for pain, which may be less potent, but will still provide some pain relief.

As another example for Special Actions 732, the control code can trigger alerts for specific contraindicated drugs after a medication dose is taken.

The other example shown is this illustration is upon taking a First Dose 740 out of the drug storage apparatus a call to 9-1-1 will be made on the drug consumer's 192 behalf. In this example a drug like Naloxone might be loaded into the drug storage apparatus and extracting even one dose would imply that a drug consumer 192 is in distress. In this example Naloxone helps to treat overdose and tainted drug supply issues that are resulting in many deaths in North America.

Other Special Actions 732 could be included for complex Dosing Regimen behaviours and effects. For example, upon using a first dose a Clinical Drug Trial manager could be informed. This would be different from the earlier message that occurs every time a dose is consumed out of the drug storage apparatus. In another embodiment there could be a Special Action 732 'On Last Dose' taken. For example, if a drug consumer 192 has been given additional packaged drugs and they have been placed in a secure holding container, then a message could be sent to allow the holding container to unlock. Once unlocked the drug consumer 192 could remove one of the packages and insert it into their drug storage apparatus to replaced the package that is exhausted its drug supply.

If the drug manager 188 forgets to save to the device 754 and presses the done button 756, the software will warn them that their changes could be lost. If they decide the information is all wrong and do not want anything sent to the device, they can select the Cancel button 758.

There are many other parameters not shown in this illustration. Other embodiments might include a maximum dosing gap between concurrent dosing periods. When present, this parameter would provide additional alerts and warnings to allow the drug manager 188 greater control over how far apart two doses can be. In some cases, the effects of life-savings drugs can wear off and so the next dose cannot be too far away to maintain a life-saving amount of the drug in a drug consumer's body.

In other embodiments, the drug manager 188 might be able to select as-needed (PRN) type dosing parameters. In these embodiments, the drug manager may then enter a Minimum Dosing Gap 732 between concurrent dosing periods. For example, if the Minimum Dosing Gap 732 is set to 12 hours and a drug consumer 192 has an 'as-needed' dose at 8:00 am on Monday morning, they would not be able to take their next potential dose until 8:00 pm on Monday night. These and many other parameters and embodiments make the parameters very useful for determining the operational behaviour of the drug storage apparatus and the locking and unlocking of the storage unit containing the drugs to be consumed.

Figure 8:
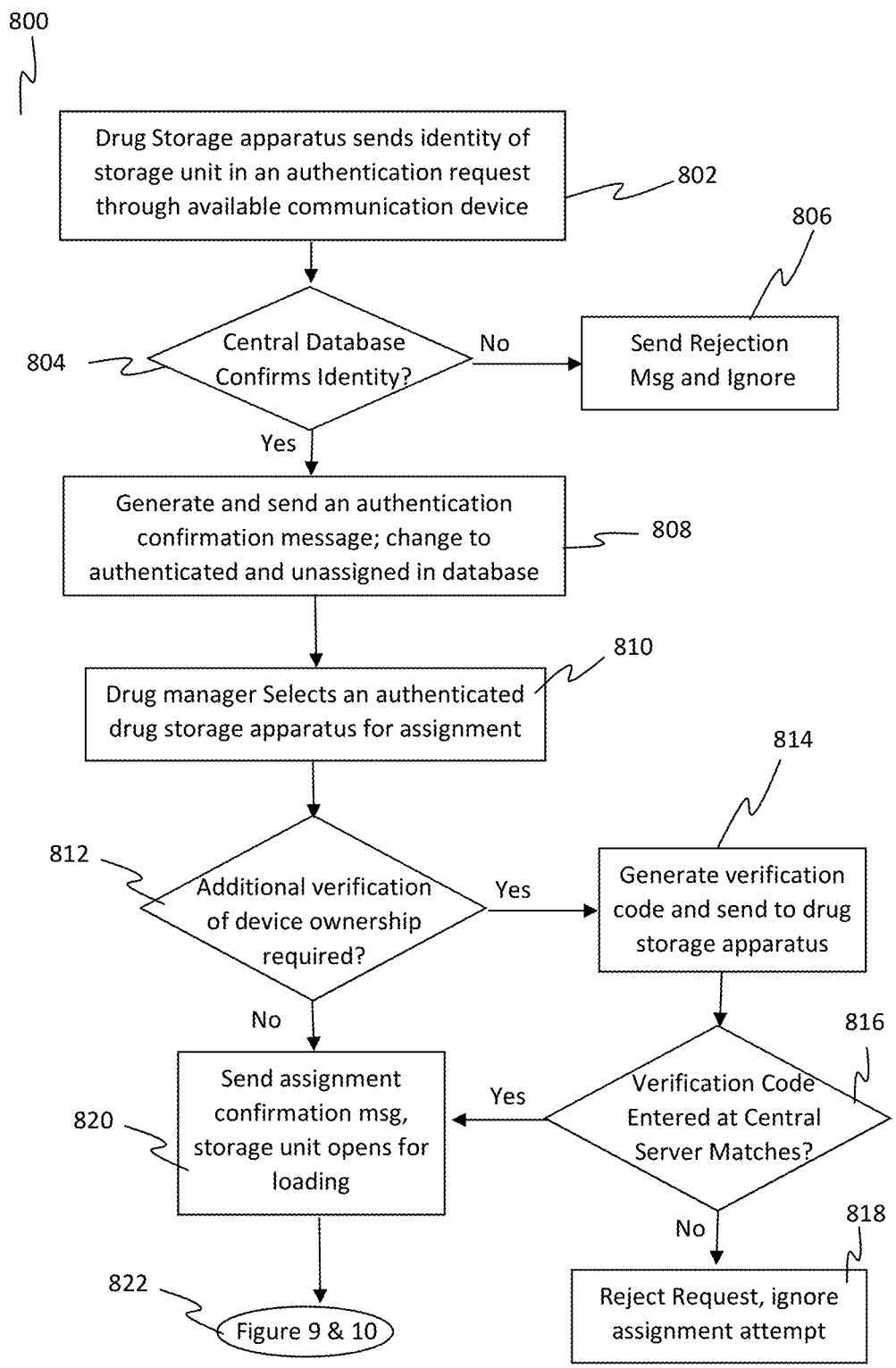
FIG. 8 shows a data flow diagram for initial steps in assigning a drug storage apparatus.

Turning to FIG. 8, there is shown a data flow diagram 800 for the initial steps in assigning a drug storage apparatus according to one embodiment of the invention. In this embodiment, the drug storage apparatus must first send the device-identity of a storage unit in an authentication request message through an available communication device 802. As discussed previously, the device-identity of the storage unit within the drug storage apparatus might be a CPU chip device-identity, a device-identity chip value, or some other private number known only to the central server 180 and stored in non-transitory memory in the central server's 180 database 184.

If the central database 184 does not confirms the device-identity 804 for the central server 180 then a rejection message is sent, and the request is ignored 806. This could be a case of a rogue drug storage apparatus trying to impersonate a real drug storage apparatus. In order to prevent such rogue devices from gaining access, it is important to maintain the privacy of the storage unit's device-identity.

If the central data 184 confirms the device-identity 804, an authentication confirmation message is sent to the drug storage apparatus and the database record for this drug storage apparatus is changed to indicate its status is authenticated and unassigned 808. When the drug manager 188 uses the UI, as discussed previously, they can see all authenticated drug storage apparatuses. They can select an authenticated and unassigned drug storage apparatus for the assignment process 810.

In some embodiments, the drug manager 188, before assigning a drug storage apparatus, may first have to verify they are in possession of the drug storage apparatus they have selected in the central server's 180 UI. If this is required, a randomized verification code is generated by the central server 180 and sent to the drug storage apparatus 814. If the correct verification code is then entered by the drug manager 188 as the central server's 180 UI 816, they will be allowed to perform an assignment of the drug storage apparatus 820. If they enter an incorrect verification code, the request is rejected and the central server 180 ignores the assignment request 818.

Figure 9:
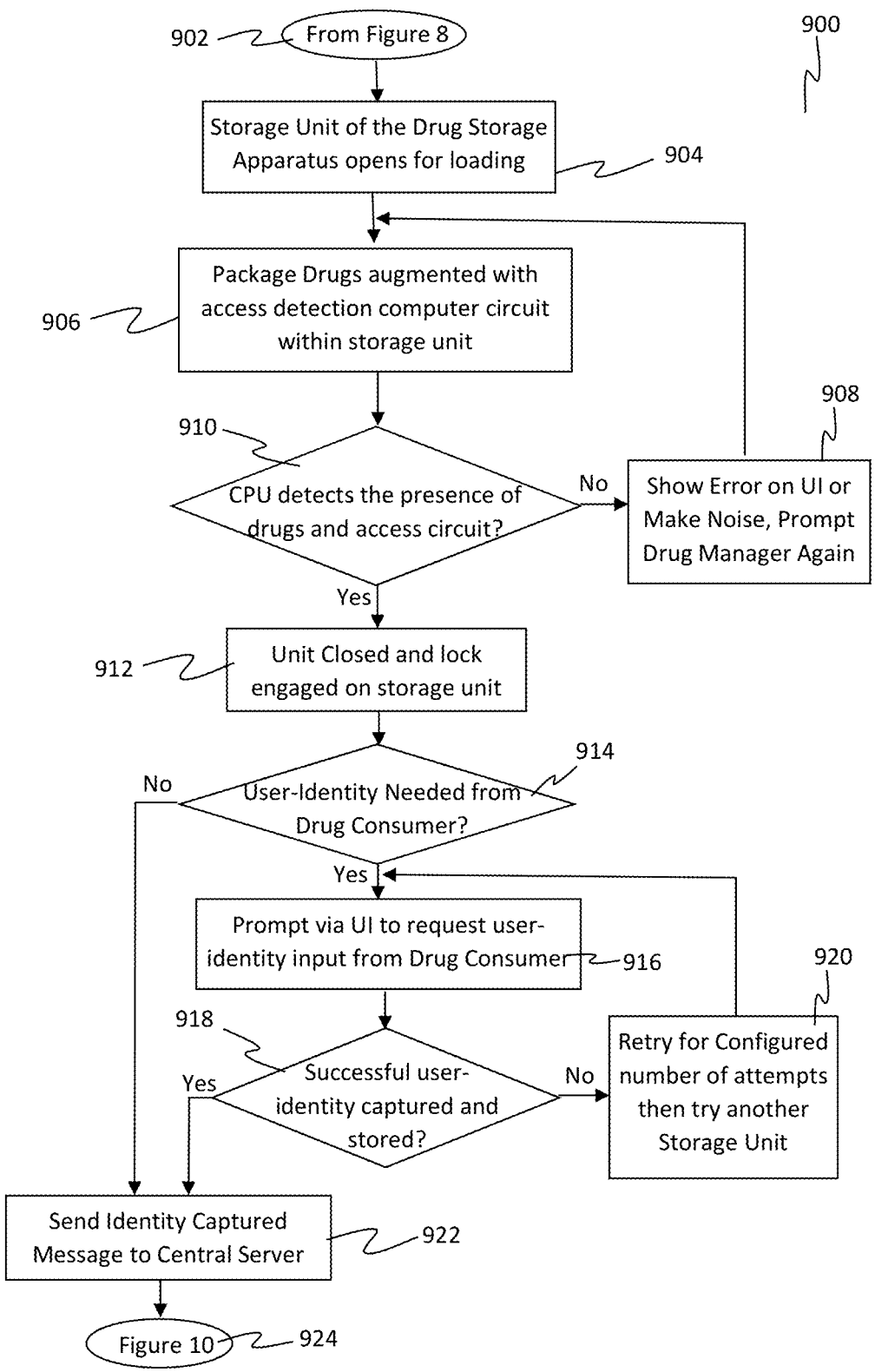
FIG. 9 shows a data flow diagram for steps required to load and prepare a drug storage apparatus for use by a drug consumer.
Figure 10:
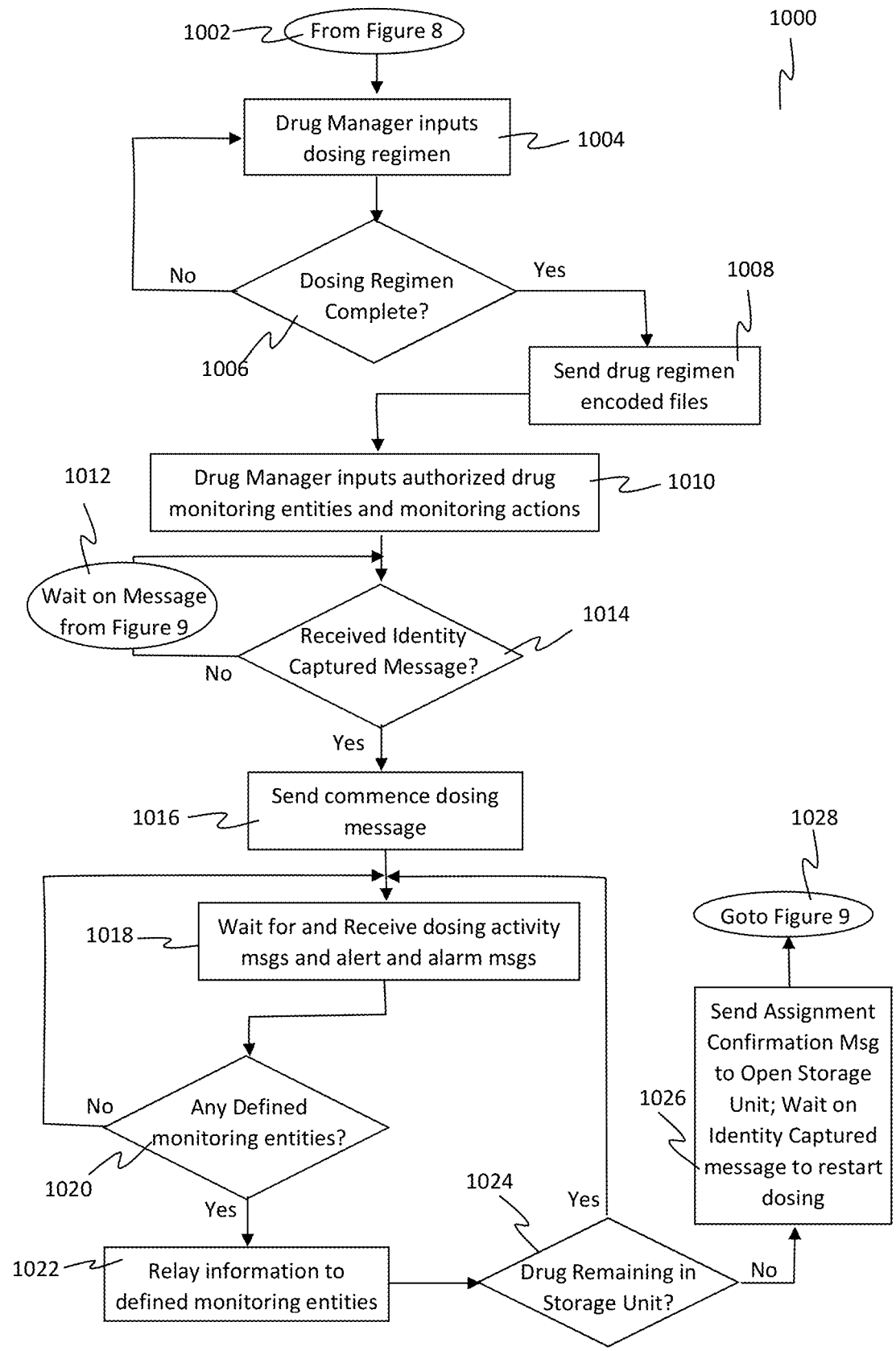
FIG. 10 shows a data flow diagram for steps to start dosing for a drug storage apparatus.

In those embodiments where a secondary verification is not required, or if the drug manager 188 passes the secondary verification, the central server sends an assignment message to the drug storage apparatus 820. This message causes the storage unit within the drug storage apparatus to open for loading 820. The data flow presentation then moves to FIGS. 9 and 10. FIG. 9 is focused on activities at the drug storage apparatus and FIG. 10 is focused on the remaining activities at the central server 180.

Turning to FIG. 9, there is shown a data flow diagram 900 for the steps for loading and preparing a drug storage apparatus for use by a drug consumer 192, according to another embodiment. Once assigned by a drug manager 188, these actions take place after the actions shown in FIG. 8 are completed 902. The drug storage area of the drug storage apparatus is now open and ready for loading 904. This could be an initial loading or it could be a reload, after the previously loaded drugs are fully consumed.

In one embodiment, the packaged drugs are first augmented with an access detection computer circuit and placed in the storage unit 906. In another embodiment, the packaged drugs already contain the augmented access detection circuit within their packaging enclosure 906. In other embodiments, the step of loading the packaged drugs into the drug storage apparatus creates an access detection computer circuit 906.

Once the drugs are placed into the storage unit, the CPU must be able to detect the presence of the drugs using the coupling associated to the access detection computer circuit 910. If the CPU is unable to detect the correct augmented packaged drugs, then an error message is shown on one or more of the UIs associated with the drug storage apparatus 908. Additionally, an error sound, beep or signal could also alert the person loading the drugs that a problem exists 908. In some embodiments, the drug manager 188 is loading the drugs. In other embodiments the drug consumer 192 could be performing a reload of the drugs and receives this error indication 908. If an error has resulted, the user can remove the augmented or non-augmented packaging and try again 906. For example, perhaps the person forgot to augment the packaged drugs and must affix the necessary access detection computer circuit.

Once the CPU detects the presence of drugs and the access detection computer circuit 910, the storage unit can be closed and locked 912. Prior to the CPU detecting the correct access detection computer circuit, the person might have closed the storage unit, but it would not have locked and my be providing notifications warning that the storage unit is not secured. With the storage unit closed and locked 912, a check is made to determine if a drug consumer 192 user-identity is required 914. A user-identity may not be required in the case of a reload of drugs, such as when all previously loaded drugs have been ejected and consumed. In this case, the user-identity may already have been acquired and stored in memory during the initial loading.

If a user-identity has not yet been acquired 914, the UI on the drug storage apparatus indicates that a user-identity input is required 916 from the drug consumer 192. Once an attempt to provide a user-identity input is made, if the collection of the user-identity input from the drug consumer 918 is unsuccessful 920 then additional attempts to acquire the user-identity input can be performed 920. In some embodiments, there is a maximum number of allowed attempts that may be performed. The number of allowed attempts may be fixed or configured at the central database 180 for a specific storage unit. In these embodiments, if too many failed attempts are reached, the process stops and the central server 180 is given a "critical failure" alarm message. In some embodiments, there may be no limit on the number of attempts that can be made to provide a user-identity input.

In some embodiments there could be more than one user-identity for drugs that require special operation. For example, the patient may need to have a backup proxy-agent to extract a dose of Naloxone from the drug storage apparatus, this proxy-agent's user-identity must also be acquired and staved in the drug storage apparatus. In other embodiments the proxy-agent used to extract the drugs could be a caregiver or loved one. The proxy-agent could be an adult extracting the drug dose for a child or an infirmed parent. A drug consumer can be a proxy agent for other users (e.g. children, seniors) and their biometrics can be authorized for multiple users.

If the acquisition attempt is successful 918 and storage takes place, or a user-identity was not required 914 because it was already acquired, the drug storage apparatus sends a "user-identity captured" message 922 to the central server 180. Once this message is sent, the process moves to FIG. 10 924, specifically at the point in FIG. 10 where it requires confirmation that a captured and stored user-identity for the drug consumer 192 exists.

Turning to FIG. 10, there is shown a data flow diagram 1000 for the final steps for when starting dosing for a drug storage apparatus according to one embodiment of the invention. The entry point into the new assignment of a drug storage apparatus comes from FIG. 8 1002. The initial steps in FIG. 10 can occur before, after, or concurrently with the steps shown in FIG. 9.

With the assignment underway as discussed in FIG. 8, the drug manager 188 is able to input the dosing regimen 1004 for this drug consumer on their specific drug storage apparatus. The dosing regimen is reviewed to ensure that all the required fields are complete 1006. The drug regimen encoded files will not be sent to the drug storage apparatus until all required fields are completed by the drug manager 188. If there are fields that still must be completed, the drug manger 188 will be directed to provide the missing information. When all fields are complete, the encoded drug regimen files are sent to the communication device within the drug storage apparatus 1008.

The drug manager 188 can then enter the authorized drug monitoring entities and the requested monitoring actions 1010. These inputs to the UI are optional as the central server 180 will maintain and present all the information received from the drug storage apparatus in its own database 184. However, to get the benefit of notification and adherence tracking one or more authorized drug monitoring entities 190, 194 can be defined 1010. These could be loved ones, trained professionals, nursing home staff members, doctors, pharmacists, the drug consumer 192 themselves, or other individuals or organizations. In some embodiments there could be monitoring services to assist with drug consumer 192 care. In other embodiments, the drug monitoring entity is collecting all the adherence data to built statistical models around adherence success rates, problems areas, and problem times. This type of data can be anonymized and can be presented back to trained professional to assist them in providing the best possible care and solutions for their patients.

Once the drug monitoring entities 190, 194 are defined, the monitoring actions can be selected for each defined monitoring entity. These actions allow for different monitoring entities to receive notifications for different events. For example, some monitoring entities, such as a doctor, may only wish to receive notifications relating to serious or life-threatening events, while other monitoring entities, such as the drug consumer 192, may want to receive less urgent reminders and concern or just casual reminders.

With the drug regimen encoded files delivered to the drug storage apparatus, the central server 180 is ready to begin the dosing process. However, it must first check to see if the "user-identity captured" message has been received from the drug storage apparatus 1014. This message indicates the user-identity of the drug consumer 192 has been captured by the drug storage apparatus 1014. If the message has not yet been received, the central server 180 waits for the message to be sent in accordance with the steps outlined in FIG. 9 1012. This is where the output of FIG. 9 data flow enters FIG. 10 data flow. This wait could be performed using hardware or software timers or some other mechanism. The central server 180 may also display messages on the UI being used by the Drug Manager 188 to remind them that this step has not yet been performed.

Once the user-identity captured message is received 1014, the central server 180 can send the "commence dosing" message to the drug storage apparatus 1016. The central server 180 then waits on dosing and activity messages from the drug storage apparatus 1018. These messages could also include alerts and alarms based on user activity, or lack of activity 1018. If there are currently no drug monitoring entities 1020, the central server 180 just saves the message locally and returns to wait for more messages 1018.

If there are defined monitoring entities with notifications enabled 1020 the messages from the drug storage apparatus are prepared and are relayed to the defined monitoring entities 1022. In some cases, calculations and interpretation is required at the central server 180. During some of these calculations and interpretations, local review of the data by the central server 180 additional actions might be required.

As a special case of such calculations, if a "drug consumed" message arrives at the central server 180, the central sever reduces the drug count to determine the total drugs remaining. If the total drugs remaining is now zero 1024, a special message can be sent 1020 to drug monitoring entities. Exhaustion of drug supply also causes an "assignment confirmation" message to be sent to the drug storage apparatus 1026.

Receiving this "assignment confirmation" message causes the storage unit controlled by the drug storage apparatus to be opened 1026, allowing more drugs to be inserted into the storage unit. Control returns to FIG. 9 1028 and the drug storage apparatus can prompt the user (drug consumer 192 or drug manager 188) to remove the empty drug package and reload new packaged drugs that are augmented with an access detection computer circuit. When this is complete, a new "user-identity captured message" is received 1012 and the central server 180 sends a "commence dosing" message 1016. The process continues as new dispensing and dosing messages are received and processed 1018.

Figure 11:
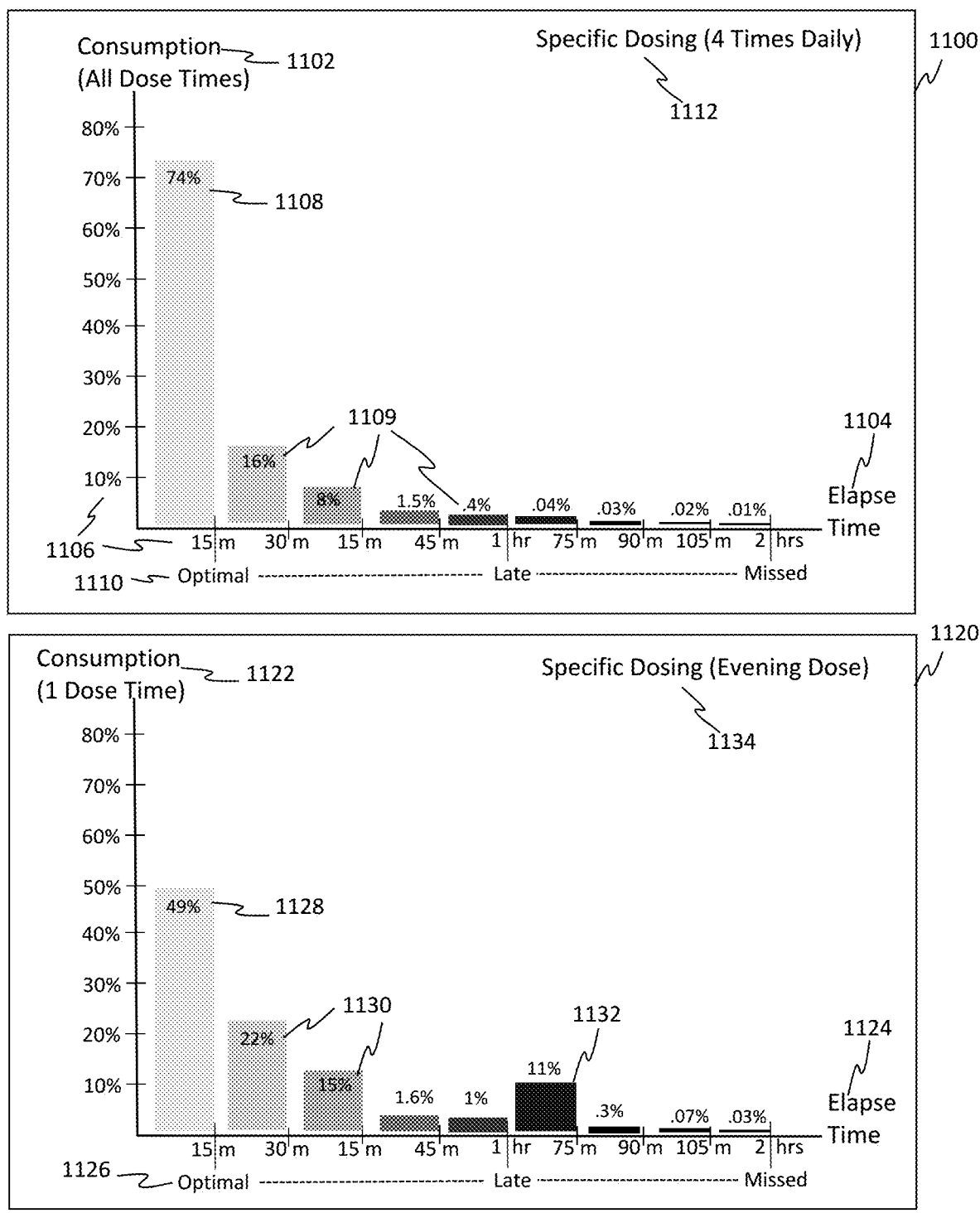
FIG. 11 shows a graphic adherence bar chart and visual elements for adherence data when specific dosing times are prescribed.

Turning to FIG. 11 there is shown adherence bar charts 1100, 1120 showing two embodiments of how adherence data can be illustrated when specific dosing times are prescribed. The two illustrated charts 1100, 1120 are provided as a limited illustration of the some of the numerous ways that adherence and drug consumption data can be used to review important information about drug consumption patterns and the effects of drug consumption. When the drug storage apparatus is used in conjunction with prepared and downloaded dosing regimen, patterns and behaviours can be tracked.

In some embodiments, the system allows trained professionals and clinical drug trial managers to establish optimal drug consumption guidelines and determine how well drug consumers are adhering to dosing times and regimen. In other embodiments, the system allows trained professionals to see how patients respond to as-needed dosing when different medications are used. These embodiments are highlighted further in FIG. 12.

There are many other embodiments where other kinds of drug prescribing guidance and drug regimen fine tuning can be attained using the system. These types of calculations can be performed at the central server by the analyzing the drug access detection signals against the various parameters established by the drug regimen parameters configured at the central server. In some embodiments, the data stored at the central server 180 can be downloaded to another device for analysis.

FIG. 11 shows two charts 1100, 1120. The first chart 1100 calculates consumption percentages 1102 for drug consumers. This chart could be related to any duration of data. For example, it could be related to a single weekly blister pack, as prescribed and delivered by the pharmacy, or it could be related to months or years of data. The chart could be for any number of drug consumers. For example, it could be for one drug consumer or millions of drug consumers. In many embodiments, anonymizing and aggregating data provides a clearer picture of drug consumption patterns.

In the first chart 1100, the total number of dosing sample ('S') is divided by number of doses consumed in a given period of time ('C') 1104. Each of these resulting numbers are multiplied by 100 to give a percentage 1102 of drug consumers that have taken their medication within that period of time, across all dosing periods for the first chart 1100. For example, if there 4,500 total samples (S) and 3,330 drug consumers consumed their dose before the 15 m mark that would calculate as: 3330/4500*100=74% (the first bar 1108). This same calculation can then be used on the remaining time periods over the total samples collected 4500 (the remaining bars 1109).

These types of bar charts can have many different types of values on their axes 1102, 1104. In the first bar chart 1100, the consumption percentage for all dosing times 1112 is shown on the Y-axis 1102 and the elapse time for a given dose is shown on the X-axis 1104. In other embodiments, there could be the number of days in the week against the success or failure to take a medication dose. Many other embodiments to chart the consumption data against the regimen data are possible.

In the embodiment shown in the first bar chart 1100, the elapse time on the X-axis shows a few important dosing-time milestones 1110. For illustration purposes, these are presented as the optimal time, late time and missed time 1110. In some embodiments, the drug manager can configure the optimal time for drug consumption through the user interface provided by the central server.

In addition, the drug manager could also configure the system to send out a "late dose" notification message when a late dose time has been reached. This could help remind the drug consumer and any caregivers that the drug dose has not yet been taken and is considered late. The effects of this wake-up notification message can be seen in the second chart 1120.

The second chart 1120 shows data for a specific dosing period of the day, this in this example the Evening Dose 1134. Narrowing in on the data for a specific dosing period can allow a drug manager to get finer levels of detail on the calculations. For example, when compared to the first chart 1100 showing data for all dosing periods, it appears that drug consumer(s) tend to take the Evening Dose 1134 later than all doses on average. The number of doses taken at the optimal time (before 15 minutes) is significantly lower 1128. Each of the four subsequent times 1130 are also lower. The data also shows an uptick for the period immediately after a "late dose" notification is sent 1132, suggesting that the notification is helpful in reminding drug consumers take their medication.

A drug clinician might then be able to speculate as to the cause of the late dosing and the reliance on the reminder. For example, the drug clinician might hypothesis that when a patient starts to consume alcohol with their meal, and possibility starts to watch television, they forgot to take their evening dose of drugs on time. This can be made possible through the use of advanced calculations and metrics as provided by comparing the drug access detection signals against the recommended drug regimen established by a drug prescribing professional.

Figure 12A:
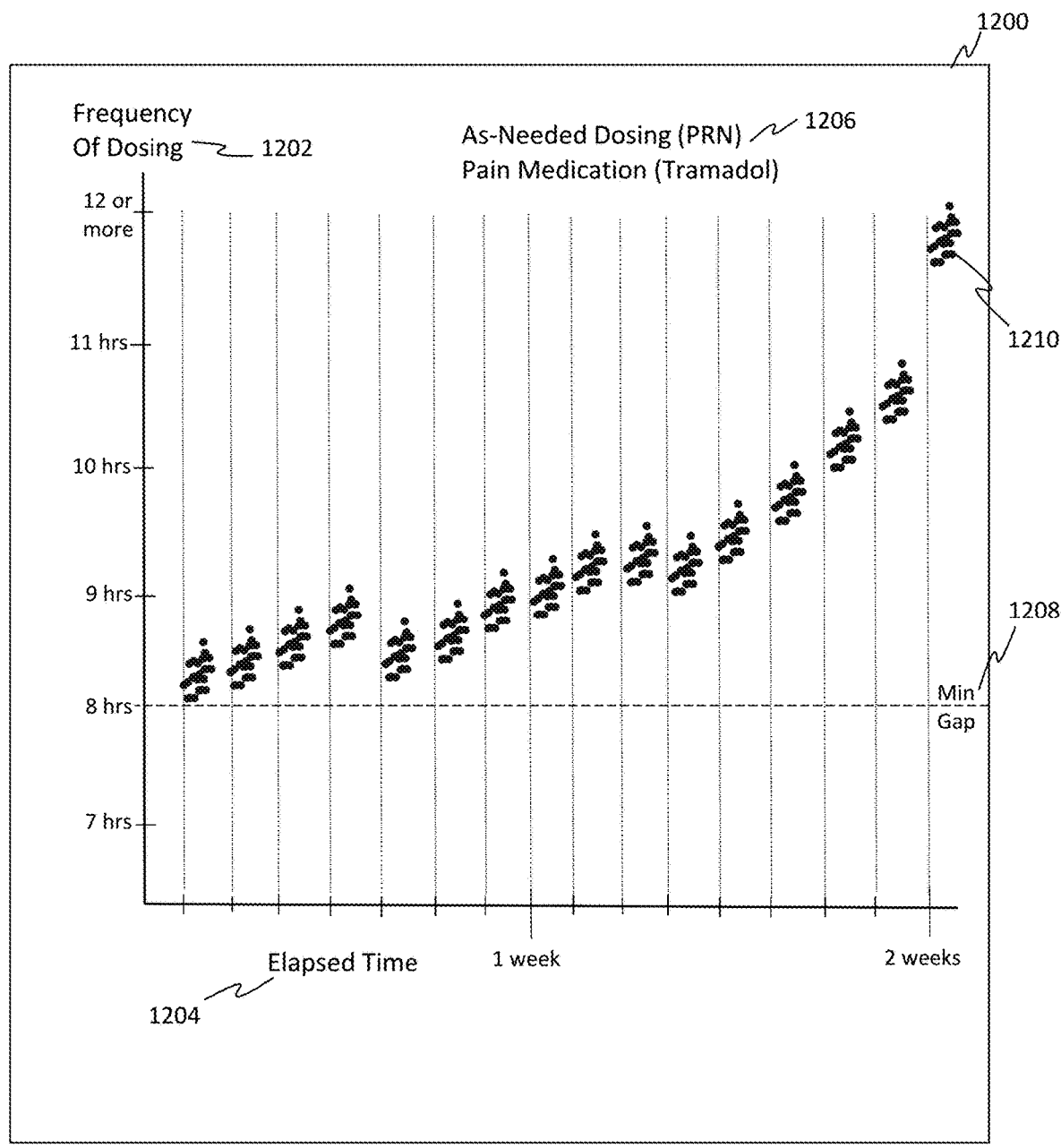
FIG. 12A shows one embodiment for creating a scatter plot showing the frequency of drug consumption over a period of time when as-needed dosing is prescribed.

Looking at FIG. 12A there is shown an illustration 1200 showing one embodiment for creating a scatter plot showing the frequency of drug consumption over a period of time when as-needed dosing is prescribed. In this embodiment, a large number of dispensed drugs are tracked and plotted on a graph based on their distance from the previously consumed dosage. Thanks to the design of the system, the user-identity based extraction of drugs can be tracked from one authenticated drug storage apparatus and plotted 1200 very precisely. In this example, the dosing method is 'as needed' (PRN) 1206. In other examples and embodiments, many other types of dosing regimen could have been followed.

To create a drug consumption frequency pattern, the hardware processor in the central server performs one or more calculations. In this embodiment, a calculation is made using a formula such as: Current-Drug-Consumption-Time (CDCT) minus Previous-Drug-Consumption-Time (PDCT), for the same drug consumer from the same authenticated drug storage apparatus. This calculates a frequency of dosing 1202. For example, if a drug consumer extracts a drug at 08:00 when they wake up and then consumes a second drug with supper at 17:00 they have a 9-hour frequency gap between those two doses.

A longer period of time represents the X-axis 1204 in this scatter plot. For this embodiment, looking over a two-week period of time provides a good basis for seeing how a drug consumer is doing with a two-week prescription. In this example, the drug that has been prescribed is Tramadol 1206, which is a strong opioid-based pain reliever. These types of drugs can be addictive in nature so tracking their frequency is very important yet often not done in the medical community.

The other advantage of the system over other systems is that the tamper-proof, tamper-detecting storage unit requires user-identity to dispense drugs. This allows the enforcement of a minimum gap time 1208. The minimum gap 1208 is extremely important with 'as-needed' dosing, especially when opioid type narcotics are prescribed.

Figure 12B:
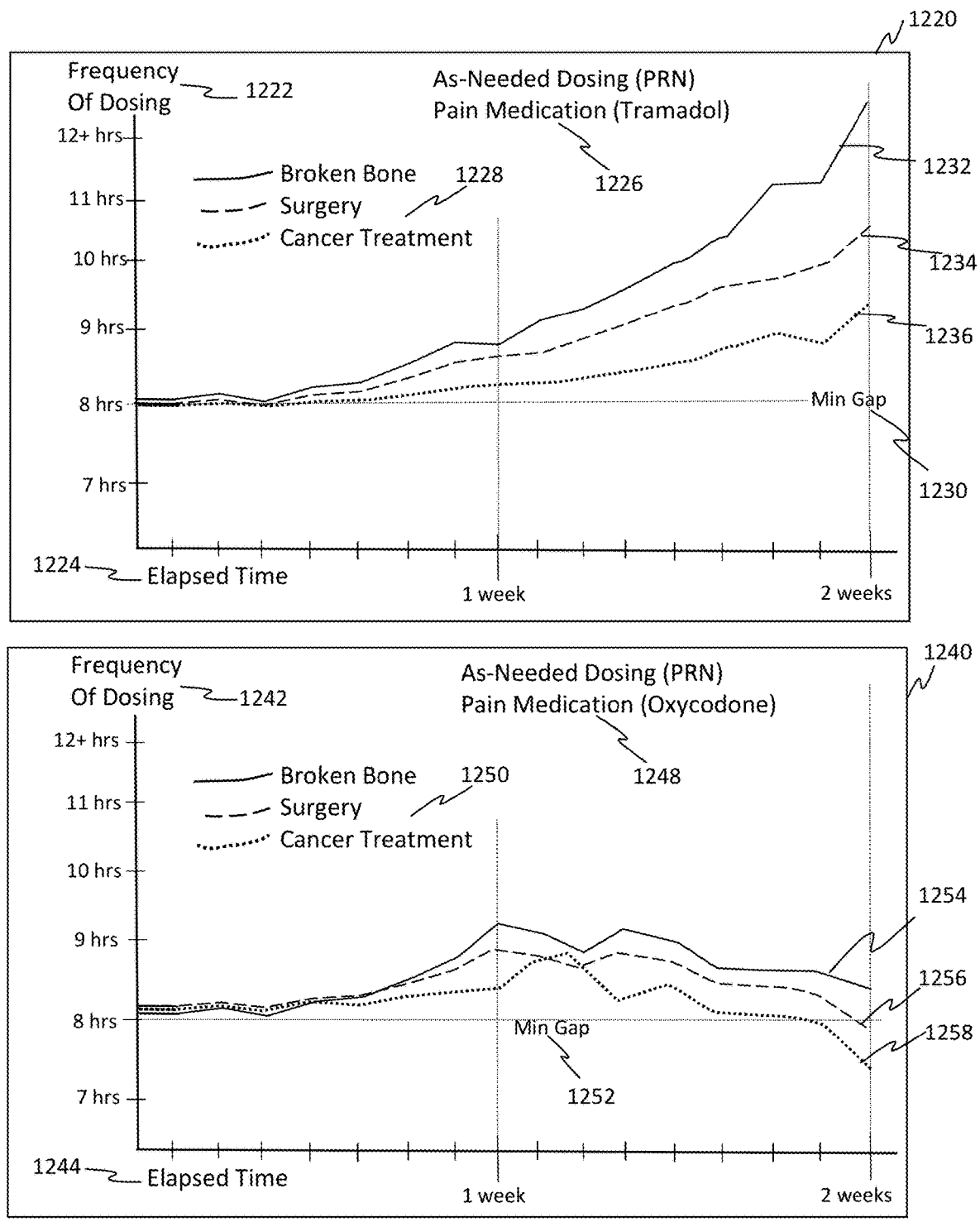
FIG. 12B shows two embodiments for creating a line chart from the scatter plot data showing the frequency of drug consumption over a period of time when as-needed dosing is prescribed.

The resulting scatter plot output 1210 illustrates a vague pattern of reduced usage and dependency of tramadol by the drug consumer. As the number of plot points increases, this type of method has limitations. Trying to plot different types of data together is also limiting and can be visually confusing. FIG. 12B shows another method with yet further calculations to allow for greater comparison of different data points.

Turning to FIG. 12B there are two illustrations 1220, 1240 showing two embodiments for creating a line chart from the scatter plot data showing the frequency of drug consumption over a period of time when as-needed dosing is prescribed. The input to these two-line charts would be similar to the scatter plot shown in FIG. 12A, but additional calculations are performed to allow a line to be created between each of the 14 days the prescription is followed.

Similar to the embodiment shown in FIG. 12A, the frequency of dosing 1222 is used on the Y-axis to look at how often a drug consumer is taking their drugs. The formula discussed earlier was: Current-Drug-Consumption-Time (CDCT) minus Previous-Drug-Consumption-Time (PDCT). In FIG. 12A, this number was just plotted and marked in the scatter plot illustration. In this example, a further step is performed to find the average for all data points on a given day. For the formula to create the average. The calculation would be: SUM(CDCT-PDCT) divided by COUNT(ALL DATA POINTS). Effectively, the average is the sum of all the values divided by the count of the values used to create the sum.

The embodiment shown in the first line chart 1220 shows the as-needed dosing for tramadol 1226 for patients who had broken bones, surgery, and cancer treatment 1228. Each of these different classes of medical need, resulting in a need for pain relief, have been charted 1220 against each other to see if the data reveals any interesting patterns. When looked over the period of two weeks 1224, about the length of a normal pain relief medication, a professional might be able to see signs of trouble. Similar to FIG. 12A a minimum gap 1230 has been used by the medical professional to ensure a drug consumer is unable to take doses of their medication too close together.

In this example, we see the line chart shows that drug consumers that are taking pain release for broken bones are able to drop off from using the drug very well 1232. By the two-week mark they are taking the pain relief drug beyond the 12-hour mark. Moving to a patient recovering from surgery, we see that pain relief is more important, and the line created on the chart 1234 does not move toward the 12+ hour mark very quickly. Finally, based on the data, patients dealing with cancer and the resulting cancer treatments, like radiation and chemotherapy, are more likely to need pain relief more often and for a longer period of time 1236.

The second line chart 1240 shows a different drug called Oxycodone 1248. This drug has a notorious history of being addictive and in many jurisdictions is no longer prescribed. If we chart a similar set of patients who are taking oxycodone for broken bones, surgery and cancer treatment 1250 we see very different result.

In this illustration, a professional could be able to see that the frequency of dose 1242, over the two-week elapsed time 1244, shows a strong tendency of growing dependency by the drug consumer. An advantage of the system is that the minimum gap time 1252 can more readily be enforced through the downloading of the drug regimen into the authenticated drug storage apparatus to limit very serious drug addiction to oxycodone 1248.

The first line 1254 indicates the drug consumer recovering from a broken bone was doing reasonably well by the 9-day mark, but after that started to take the mediation more frequently. The next line, for the drug consumer taking oxycodone for surgery 1256, shows a similar pattern up to the 8-day or 9-day mark. However, in this line, the drug consumer starts to attempt to provide their user-identity before the 8-hour minimum gap time 1252 at about the 14th day. Since the authenticated drug storage apparatus is able to detect user-identity input attempts, this information can be collected and provided as a 'failed attempt' to extract drugs.

Finally, the most serious condition for the person dealing with cancer treatment shows a dramatic plunge of the line 1258 on around the 13th day. This information might be collected for an individual drug user to track their individual health, or for a number of drug users all going through cancer treatment to determine information about overall trends. For example, if the data in the chart 1240 is for a large number of patients, based on this data, a professional might decide that, if they are going to prescribe oxycodone, it can be for no longer than 8 days.

These and many other kinds of calculations can be performed to created useful drug consumption patents for trained professionals. Other embodiments could be implemented where clinical trial drugs are housed within the authenticated drug storage apparatus. For example, a clinical drug manager might look for the effectiveness of a new drug based on consumption patterns. Each drug consumer might fill out a questionnaire after every single drug consumption and this is correlated back to when they took their drug.

Figure 13:
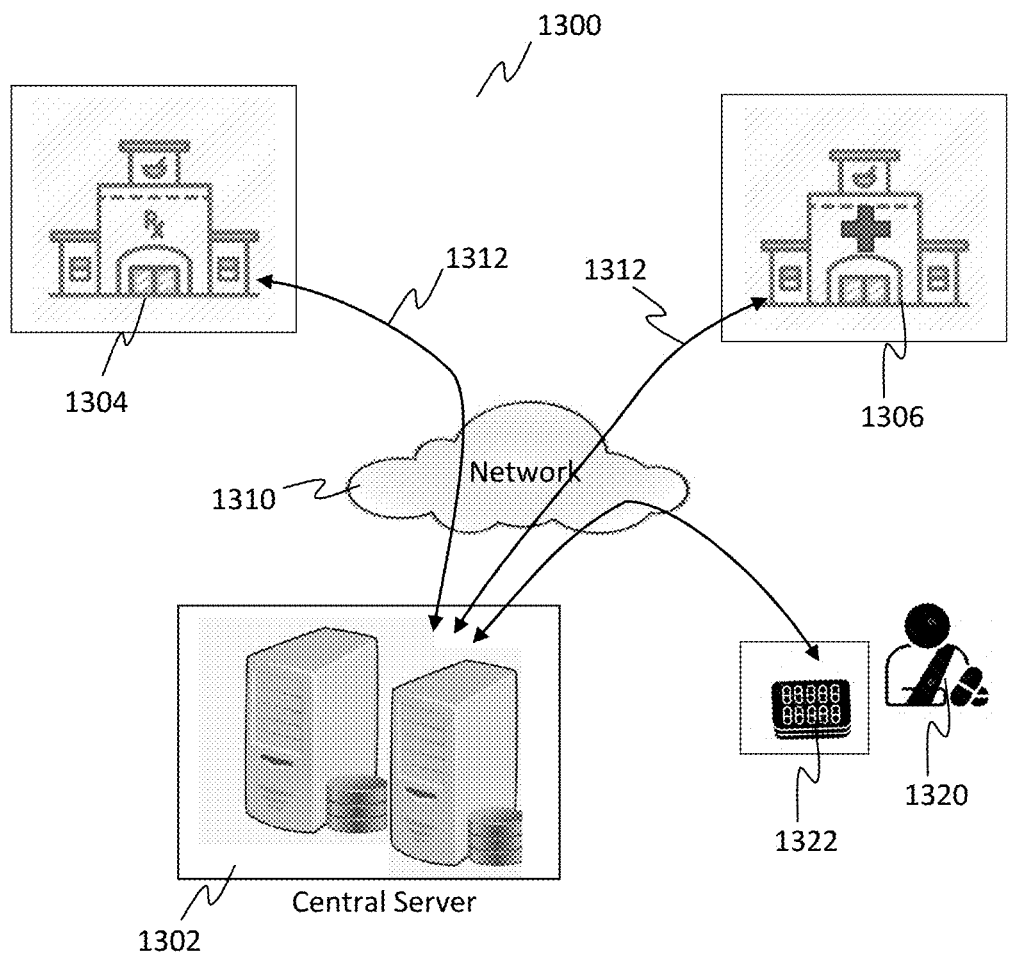
FIG. 13 shows an overview of connections made from the central server to additional external systems.

FIG. 13 provides an overview 1300 of connections made from the central server 1302 to additional external systems 1304, 1306. In some embodiments the central server 1302 can be connected 1312 to other offices 1304, 1306 through a common network 1310. Such network connections 1312 are possible through public networks 1310 like the Internet, or through private virtual private networks (VPNs) like an internal hospital system or a large drug manufacturer. These links can provide additional forms of integration with the central server 1302 to further streamline operations and usage workflows.

There can be a wide variety of external systems 1304, 1306 used to connect into the central server 1302. These systems can include Pharmacies, Doctor's offices, Hospitals, Nursing Homes, Long-term Care Home, clinical drug trial center and many others. In some embodiments these external systems 1304, 1306 can have information to assist the operation of the central server 1302. In other embodiments these external systems 1304, 1306 will receive information from the central server 1302 to assist them. In other embodiments these external systems 1304, 1306 will both provide information to the central server 1302 and accept information from the central server 1302.

Secure communications 1312 between the central server 1302 and external systems 1304, 1306 can be established using several methods. In one embodiment both server and client secure socket layer (SSL) security certificates are used to create an encrypted SSL link between the two ends. In another embodiment the two ends can negotiate an encryption key for symmetric or asymmetric encryption to be used. Over this secure link 1312 messages following a shared format can be exchanged to perform a range of functions. Such formats like Java Script Object Notation (JSON) are commonly used for such communications.

As discussed, many times of communication messages can be exchanged over the secure connection 1312. In some embodiments the central server 1302 might be able to receive dosing regimen for a given patient 1320 that is about to use a monitored drug storage apparatus 1322. Such dosing regimen could be received 1312 from an external system 1304 like a pharmacy or a clinical drug trial center 1306. In some embodiments a pharmacist within a pharmacy has accepted a paper prescription from the patient 1320 and has entered it into their local Pharmacy Management System (PMS). Within the PMS are software support methods to determine that the patient 1320 will be using a drug storage apparatus 1322 and will therefore take a copy of the prescription information and redirect it to the central server 1302 to apply to the patient 1320. Identification of a patient 1320 can be done using health card information, digital identification, driver's license information, social security number and many other methods.

With this dosing regimen received from the external system 1304, a user of the central server 1302 can use the central server's interface to assign a drug dispensing apparatus 1322 and assign the uploaded dosing regimen already present for that patient 1320. These steps of setting up the drug dispensing apparatus 1322 have been thoroughly described in previous figures. With the initial drug regimen already uploaded from the external system 1304 the user on the central server 1302 could make additional changes to adjust for the type of drug dispensing machine 1322 and the specific patient's 1320 needs.

In some embodiments the central server 1302 might be able to send drug consumption and drug adherence informational messages 1312 to external systems 1304, 1306. The external systems might be a pharmacy, doctor's office, hospital, nursing home, clinical drug trial center or many others. In some embodiments the drug consumption and drug adherence are applied to the original patient 1320 that was prescribed the drugs in the first place. In this way a professional like a pharmacist or doctor might be able to see how their patient 1320 is doing with their drug consumption requirements. Adherence information can be very valuable to treating and detecting whether drugs are affective and whether they are being used correctly. Such limitations in other systems can be solved with this closed-loop approach to prescribing and monitoring of drug consumption parameters.

In other embodiments the drug adherence information 1312 might be anonymized before used by the external system 1306. In this embodiment the information might provide valuable broad information, answering a broad range of medical questions. For example, questions around how a certain age group is performing when taking a certain type of drug could be answered. There might be questions around how individuals take morning drugs very drugs later in the day before bed. There could be questions around whether 'as needed' dosing regimen for pain medication is working or causing people to become addicted to the drugs. These are just a few small examples of the many types of questions that could be answered with information about drug adherence across a very large sampling of anonymized drug consumers 1320.

Figure 14:
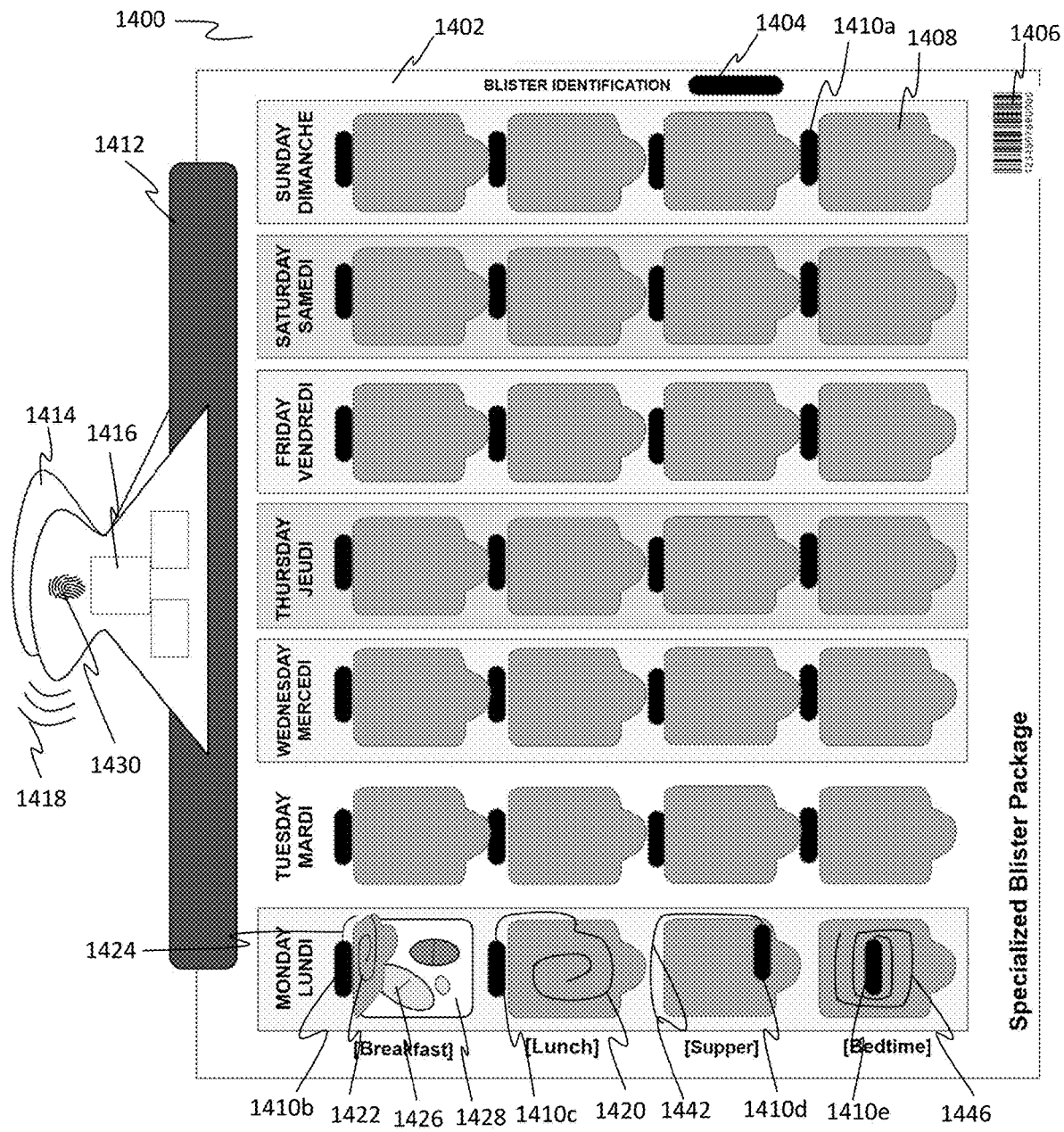
FIG. 14 shows an embodiment illustrating an RFID method for building an access detection computer circuit to detect drug access from a blister-pack storage.

The next illustration is FIG. 14 that shows an embodiment 1400 illustrating an RFID method for building an access detection computer circuit to detect drug access from a blister-pack storage. The embodiment presented in this illustration focuses on a 4-dose per day drug regimen, that lasts only 7 days 1402. The invention is not restricted to this drug regimen and can support all the other potential combinations of multiple doses per day, and shorter or longer days supported. This flexibility is essential to detect drug extraction from all types of packaged containers, including multi-pack blister containers as illustrated with this figure. The system can also work with non-blister pack containers or packaging that might have one or more drug or medication storage areas, including heat sealed drugs and others. The terms drug and medication may be used interchangeably herein.

The drug storage apparatus previous disclosed is built of several components which might include a specially constructed blister-pack 1402 with access detection computer circuits 1404, 1410, a storage unit 1414 and any associated computer systems like cell phones, tablets or wearable computers. These associations have been thoroughly discussed in previous figures.

The drug storage unit has a device-identity known only to the central server to create an authentication mechanism. When the drug storage unit is coupled with a cell phone, tablet, wearable computer, laptop or some other system the device-identity is used to create an authorized drug storage apparatus. In this embodiments any other the devices in the drug storage apparatus can provide peripherals like a fingerprint reader, a speaker system or an LCD screen. These peripherals can then be used for drug consumer identity capture and verification, for visual and audible alarms and for other purposes.

In this embodiments, packaged drugs 1426 are contained in a bottom section that is loaded with one or more medications. The bottom section is not shown in this figure but holds medications 1426 that can be prescribed drugs, vitamins, homeopathic remedies and other health supplements 1426. These are placed, into the storage area by a loved one, personal support worker (PSW), a nurse, doctor or by a professional like a pharmacist. The bottom storage unit is comprised of a collection of individual storage containment areas 1408 ("blister slots") corresponding to dosing periods and days of the week. These can vary depending on the construction and needs determined by drug consumers in the marketplace.

To secure these blister slots 1408 an access detection computer circuit 1404, 1410 is coupled to the bottom storage containment area. The access detection computer circuit 1404, 1410 acts as the blister top 1402 as shown, with corresponding individual access detection computer circuits 1410*a*, 1410*b*, 1410*c*, 1410*d*, 1410*e* that correspond to the number of individual dosing compartments 1408. The blister top secures the drugs 1426 so that the process of removing the drugs 1426 provides proof that compartment was accessed.

In other embodiments the main RFID circuit 1404 could have multiple circuit lines that run to the one or more dosing compartments. When the signal from one of the multiple circuit lines to a specific dosing compartment was broken the RFID circuit 1404 would then send back a different identification code to the RFID reader 1416. In this way the RFID circuit 1404 and the earlier circuit paper disclosure in this application can overlap in functionality.

The blister-pack 1402 might also have bar-code 1406 to complement the access detection computer circuits 1404, 1410. In this embodiment the access detection computer circuit 1404, 1410 uses a blister identification RFID 1404 that identifies the entire storage unit top that protects the bottom storage unit. This blister identification RFID 1404 can be correlated with the bar-code 1406 and the loaded medications 1426 at the time of preparation. This correlation can be used later to verify the correct drugs 1426 are going to the correct drug consumer. This association can also be shared with the central computer to be remembered and verified at various times during drug consumption.

In some embodiments the barcode 1406, the main blister RFID identification 1404, or both the barcode 1406 and main blister RFID identification 1404 can be used to identify the drug consumer that has been assigned the medications. For privacy reasons a specially designed code like the barcode or RFID can be assigned to a specific patient in place of their name to keep their identity private. This type of embodiment might be utilized in congregate living settings like long-term care home, nursing homes and senior's residences.

In these embodiments the main blister RFID 1404 or the barcode 1406 might be the same for every detectable packaged drug container received by the same patient over and over. It is common when using blister-packs for the drug consumer to be taking the same set of drugs for most of their lives.

In FIG. 14 the access detection computer circuit 1404, 1410 has 28 dosing compartments 1408, each having their own identification circuit 1410. In this embodiment the circuit is also a low-frequency, passive RFID circuit 1410. In other embodiments the use of active RFID circuits 1410 might also be advantageous for identification, power or some other design reasons.

The 28-dosing compartment circuits 1410 can also be correlated with the main blister identification RFID circuit 1404. For example, the main blister-pack identification circuit 1404 might generate a code like AB-1234-00-00 and the individual compartment circuits might be AB-1234-01-01 for the initial Monday breakfast dosing compartment 1428 RFID circuit 1410*b* to AB-1234-07-04 for the final Sunday bedtime 1408 dosing compartment circuit 1410*a*. In this embodiment the blister top 1402 is augmented with a security seal 1412 which is added after the drugs 1426 are loaded and the blister top 1402 is applied. In this same area a specialized storage unit 1414 computer has been added. The storage unit 1414 storing all the necessary hardware, memory and other circuits to enable to coupling to the access detection computer circuits 1404, 1410.

The person preparing the access detection computer circuit 1404, 1410 must select a storage unit 1414 to couple to the access detection computer circuit 1404, 1410. In this embodiment the storage unit 1414 is shown as a clip-on device. In other embodiments the storage unit 1414 could connect to another part of the blister-pack 1402, it could also be supported by a secure storage container that the blister-pack 1402 is placed inside of before and after each use.

In some embodiments the authorization for the storage unit 1414 is performed by clipping the storage unit 1414 onto a recognizable access detection computer circuit 1404, 1410 to being the flow of messages to the central server causing the assignment confirmation messages. This is then followed by setting up the dosing regimen on a provided UI either on the central server or in the drug storage apparatus. When the storage unit 1414 is coupled via Bluetooth to a mobile communications device the central server is capable of providing a secure connection and authorizing the configuration via an interface provided on the mobile communication device. The storage unit 1414 device-identity makes this authorization possible.

The use or application program interfaces (APIs) like React™, React Native™, Web API, Rest API, Angular and others is a method for bring storage unit configuration and dosing regimen creation to almost any device. The use of Internet browsers, cell phones, web connected watches, tablets and other types of computer that utilize these APIs is a way to allow the authorized storage apparatus to interact with the central server to construct dosing regimen, schedules and other types of configuration parameters to guide the operation of the storage unit 1414 and the drug storage apparatus.

The storage unit 1414 is shown with several electronic components 1416 which can include all the necessary circuitry needed to perform the functions needed for the invention. The storage unit 1416 will have a small battery to allow stand-alone operation. In some embodiments this battery might also allow for a USB type plug-in for recharging each day, week or month as recommended.

In some embodiments, the storage unit 1414 might have a lock that only opens the clip or some form of attachment system after receiving an assignment confirmation message from the central server. In other embodiments the storage unit 1414 does not have a lock and is able to couple at any time, but will only start operating after receiving an assignment confirmation message from the central server.

The storage unit 1414 would also include an RFID reader 1416 that is capable of polling the RFID circuits 1404, 1410 on the blister top to determine what RFID signals are present. These individual RFID circuits on the packaged container 1402 might be active or passive RFID circuits and in some embodiments using low-frequency (LF) RFID methods.

In some embodiments the antenna for the RFID reader 1416 is contained within a connected flap that covers the entire front or covers the entire back of the packaging area to hide and protect the pills. Extending the antenna over the entire area of the packaging area and the associated access detection computer circuit 1404, 1410 would allow for a better distribution of energy to ensure each of the individual RFID circuits 1410 powered up successfully and provided their identifications.

The storage unit 1414 would also contain some type of communication circuit that would be capable of communicating to another separate device 1418. In some embodiments the communication would be through a wireless transmission like Bluetooth, 802.11 (Wi-Fi) or cellular communications. Cellular communications can also include the use of Internet of Things (IoT) protocols and methods. In some embodiments a fixed connection might be necessary for security or quality, for example a USB type connection might be used.

The communication circuit 1416 might communicate to a range of different systems. In some embodiments the communication circuit 1416 sends and receives messages to a mobile communication device like a phone, tablet, or wearable device. This computer then relays those messages to a central server where they are acted upon based on the previous figures and disclosures. In these embodiments the cell phone can also be used to provide audio and visual alerts, prompts, notifications and alarms for medication consumption assistance.

The access detection computer circuit 1416 might also contain a biometric identity reader 1430, like a fingerprint reader circuit 1430. In some embodiments the system might employ a biometric check-in before drugs are removed from the blister-pack. Without providing this an automatic alert might be sent to registered caregivers and loved ones to indicate that drug diversion is taking place or theft of the drugs. Confirmation of the drug consumer's identity is one simply method to ensure the drugs are being accessed by the person they are intended for. In some embodiments a drug consumer's cell phone provides the biometric confirmation to ensure drug access is authenticated. This allows alerts to be raised if biometric input is absent when medications are accessed.

In some embodiments the access detection computer circuit 1416 also has various types of memory and storage capabilities. This allows for situations where the communication circuit 1416 might be out of coverage and needs to save drug extraction events to communicate with the central server. Such synchronization is valuable when dealing with communication protocols and asynchronous communication needs. Storage might also be used for storing biometric information related to the drug consumer to allow for secure verification of the drug consumer each time drugs are accessed.

Before full use of the storage unit 1414 and access detection computer circuit 1404, 1410 can take place a professional, loved one, nurse or trained user of the system assigns the storage unit 1414 to a drug consumer and associates it to an access detection computer circuit 1404, 1410. The central server facilitates this assignment using user interfaces, APIs and support tools as previously disclosed in earlier figures.

Once assigned there are several embodiments to associate the access detection computer circuit 1404, 1410 to the storage unit 1414. In one embodiment the barcode 1406 is scanned using a hand scanner and added to central server's database. In another embodiment the main blister identification RFID circuit 1404 is read and provided to the central server's database. Once assigned, medication consumption messages, missed doses and other alarms can be correlated to the correct drug consumer and passed to approved caregivers, loved ones, nurses, PSWs and even the drug consumer directly. For example, the drug consumer might just have forgotten to take their medications and a dose late reminder will provide the nudge they need to take their medications.

During the normal course of drug consumption, the drug consumer picks a storage compartment 1428 to access. In this embodiment each storage compartment 1408 has an RFID circuit 1410*a*, 1410*b*, 1410*c*, 1410*d*, 1410*e* and antenna 1420, 1422, 1442, 1446 that supports the RFID circuit 1410. In some embodiments the RFID chip 1410 and associated RFID antenna 1420, 1422, 1442, 1446 would be hidden (as shown with compartment 1408) from view and built into the top peelable flap or tab located directly above the storage area. In other embodiments these might be visible to the drug consumer.

As shown in the Monday breakfast dosing compartment 1428 the drugs 1426 are exposed the drug consumer has lifted the movable tab 1422 to expose the contents of the compartment 1428. In performing this action, the RFID antenna 1422 located inside the tab has been damaged 1424 very close to the RFID circuit 1410b resulting in enough damage that the RFID circuit 1410b can no longer receive power from the RFID reader 1416 and power up to provide its RFID identification. This process will continue when the Monday Lunch circuit 1420 is lifted and damages RFID 1410c through the lifting of the associated tab for that dosing compartment.

In other embodiments the RFID circuit 1410d is located on the liftable tab. When the drug consumer lifts the tab the antenna 1442 is broken and the RFID circuit 1410d fails to operate.

In other embodiment the entire RFID circuit 1410e and associated antenna 1446 is located completely on the moveable tab. In this embodiment the tab is completely torn off and discarded by the drug consumer. This action completely removes the RFID circuit 1410e making it impossible for the RFID reader 1414 to pick-up the presence of the RFID circuit 1410e indicating medications have been consumed from that dosing compartment. This embodiment would be well suited for an active RFID circuit 1410e where outside energy is not required for transmitting the identification.

To perform the reading of a multitude of RFID circuits, the RFID reader 1416 uses special anti-collision algorithms that enable interrogators to singulate on a specific tag. This allows the RFID reader 1416 to communicate with one tag at a time and in such a rapid succession that is appears almost instantaneous.

Progressively as the drug consumer goes through each of the dosing compartments, each of the individual RFID circuits 1410 will be damaged or removed in turn when the drugs they protect are accessed, removed and consumed. As this takes place the RFID reader 1416 detects it is unable to receive certain RFID signal identifications from the 28 individual passive RFID circuits 1410. This allows the storage unit 1414 to provide detection signals to the central server indicating precisely which dosing compartments have been accessed. This information is then communicated to the central server to allow for tracing of medication adherence, dosing times and periods and other key statistical information as previous discussed.

Figure 15:
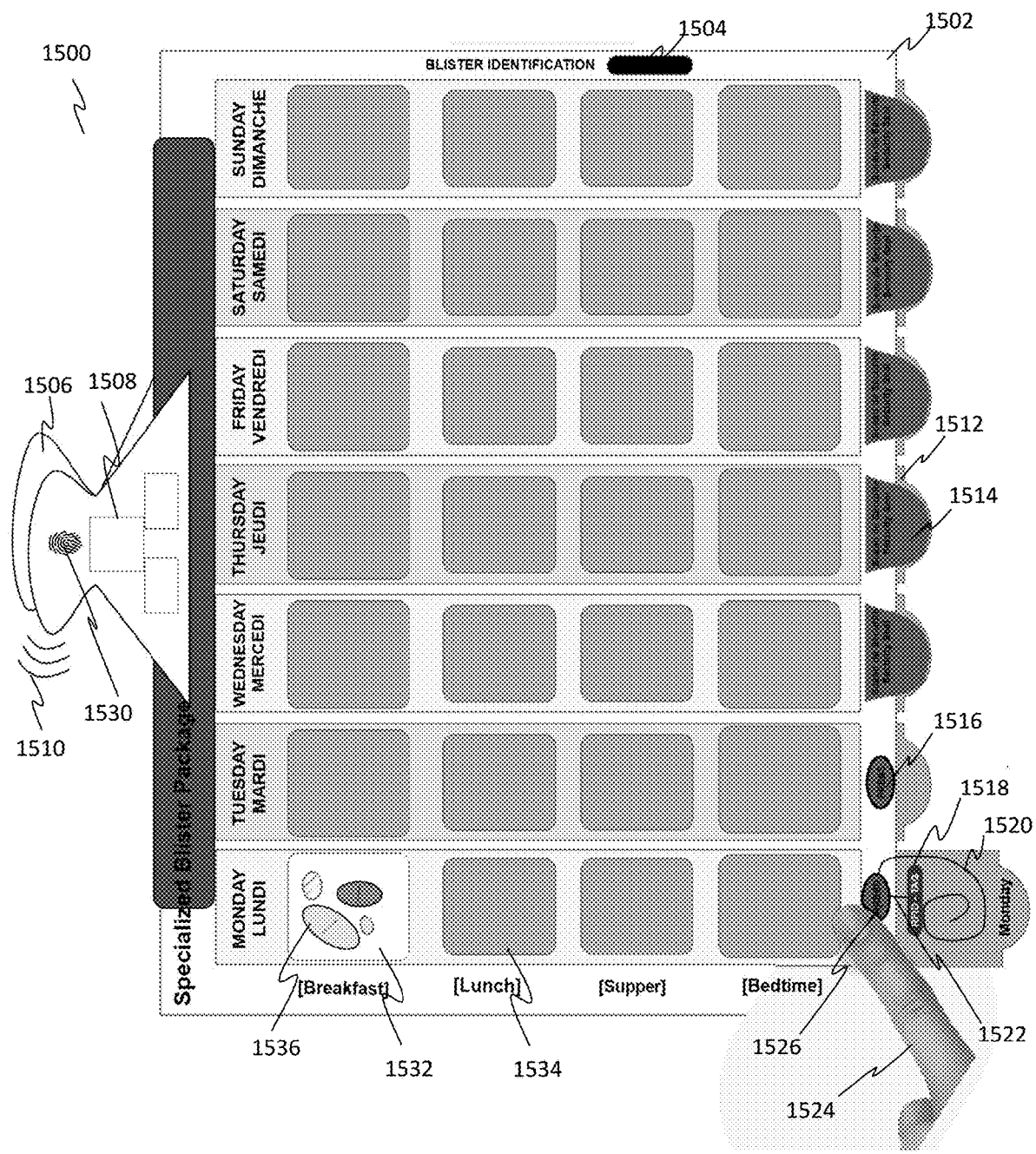
FIG. 15 shows another embodiment illustrating an RFID method for building an access detection computer circuit to detect drug access from blister-pack storage.

Moving to FIG. 15 there is provided another embodiment 1500 illustrating an RFID method for building an access detection computer circuit 1504, 1518 to detect drug access from blister-pack storage. The embodiment presented in this illustration 1500 focuses on a 4-dose per day drug regimen, that lasts only 7 days 1402. The invention is not restricted to this drug regimen and can support all the other potential combinations of multiple doses per day, and shorter or longer days supported. This flexibility is essential to detect drug extraction from all types of packaged containers, including multi-pack blister containers as illustrated with this figure.

The drug storage apparatus previous disclosed is built of several components which might include a specially constructed blister-pack 1502 with access detection computer circuits 1504, 1518, a storage unit 1506 and any associated computer systems like cell phones, tablets or wearable computers. These associations have been thoroughly discussed in previous figures.

There are many embodiments for how the storage unit 1506 couples with an access detection computer circuit 1504, 1518 to augment and detect medication extraction from a blister-pack 1502. In some embodiments the entire access detection computer circuit 1504, 1518 is placed within a secure storage unit. In other embodiments the access detection computer circuit 1504, 1518 is associated to the storage unit 1506, illustrated in this figure as a clip-on computer circuit 1506. In other embodiments the storage unit 1506 could be a slip-on, glued or affixed in some other way to create an association.

In this embodiment there is a main blister identification RFID circuit 1504. As discussed in the previous figure there could be a correlation between the main blister identification RFID circuit 1504 and each of the dosing compartment computer circuits 1518. For example, the main blister-pack identification circuit 1504 might generate a code like AB-1234-00-00 and the individual compartment circuits might be AB-1234-01-01 for the initial Monday breakfast dosing compartment 1518 to AB-1234-07-04 for the final Sunday bedtime dosing compartment circuit.

As discussed in the previous figure the storage unit 1506 can have a range of components to support the system. As previous discussed in FIG. 14, these can include some of the following components, a battery, an RFID reader 1508, locks for opening and closing, various types of memory storage, a communication circuit and biometric 1530 readers. The storage unit works with the access detection computer circuit 1504, 1518 to detect when storage compartments are accessed and provide the communication 1510 to the central server.

In this embodiment each of the storage compartments 1532, 1534 are accessed using one or more sliding elements 1512. In this embodiment each of the sliding elements 1512 correspond to a day of the week. In other embodiments the sliding elements 1512 could correspond to a dosing period of the day, for example all breakfast doses could be exposed by pulling one of the sliding elements 1512.

In this embodiment each of the one or more sliding elements 1512 are protected by a piece of security tape 1514. The security tape 1514 might have many different types of structures and properties. For example, the security tape 1514 might leave behind an indication if it has been tampered with, thus providing the drug consumer 1524. In other embodiments the security tape might not be reusable, it could leave behind a different color when removed or many other types of solutions. In this embodiment there is a specialized button 1516 located behind each of the pieces of security tape 1514. The specialized button 1516 is used in the process of a drug consumer 1524 accessing their medications 1532.

As with FIG. 14 in the process of drug consumption the drug consumer 1524 goes through a series of steps depending on which dose their wish to take. In this embodiment, following the prescribed dosing regimen the drug consumer 1524 would take four doses per day at or around breakfast time, lunch time, dinner time and bedtime. In the illustration the drug consumer 1524 has pulled the Monday sliding element 1520 and are about to take the Monday breakfast set of one or more drugs 1532. Inside of the Monday sliding element is shown an antenna 1520 connected to a RFID circuit 1518 that is associated to the Monday breakfast dose 1532. The RFID circuit 1518 might be a passive, low-frequency (LF) RFID circuit that requires its antenna to receive power for operation.

There are several possible association methods for to identify this dose. In one embodiment, as discussed in FIG.

14, the main RFID identification circuit 1504 is related to each of the individual RFID circuits 1518 using correlated identification numbers. Another embodiment would be for the RFID reader 1508 to take a reading of all individual RFIDs which could be related to each other and not the main blister identification RFID chip 1508.

After the drug consumer 1524 has pulled the Monday sliding element and taken their medications 1532 they pressed the button 1526 for the Monday dosing time 1532. The action of pressing the button 1526 results in the puncturing of the RFID antenna 1520 just before the segment 1522 that does into the RFID chip 1518 directly. Breaking the RFID antenna 1522 so close to the RFID chip 1518 results in the RFID chip 1518 being non-functional. Without the full extent of the RFID antenna 1520, the RFID chip 1518 will not be able to receive the power necessary to power up and transmit its RFID reference number.

During the process of dispensing the medication 1536 in a given containment area 1532, the storage unit 1506 will transmit 1510 signals to the central computer about what it is about to detect about the individual dosing RFID chips 1518. As each of the individual RFID circuits become sequentially disabled, messages are sent back about the consumption of drugs and the time this takes place.

In other embodiments for FIGS. 14 and 15 the central server can send various messages to the storage unit 1414, 1506 over the communication link 1418, 1530. This could include dosing regimen times and expected behaviours. This allows the storage unit 1414, 1506 or drug storage apparatus to make sounds and reminders if it does not see changes in the individual dosing RFID circuits 1518 in a timely manner. The dosing regimen might also be received into a cell phone that provides timely audible and visual reminders to the drug consumer.

In some embodiments for FIGS. 14 and 15 the central server may also send messages to request the drug consumer provide their biometric 1430, 1530. This biometric capture and confirmation might be done at the storage unit 1414, 1506, or at an associated cell phone, tablet or wearable computer system like a watch. Current communication over protocols like Bluetooth are now full secured using advanced encryption methods and techniques.

The invention claimed is:

1. A system for detecting and tracking drug extraction from one or more drug storage apparatus at a central server, the system comprising:
   one or more authenticated drug storage apparatus having:
      at least one access detection computer circuit that integrates with drug packaging containing one or more medication storage areas, the access detection computer circuit providing drug access detection trigger signals;
      a storage unit that couples to the access detection computer circuit, and has a hardware processor that receives control commands;
      an apparatus communication device for transmitting secure communication data messages, the access detection trigger signals, and an authentication request containing a device-identity value for the one or more authenticated drug storage apparatus for receiving one or more confirmation messages from a central server for verification of the authenticated drug storage apparatus and verification of assignment of the drug storage apparatus, wherein the apparatus communication device relays the one or more confirmation messages to the hardware processor;
      an user-identity input device having an identity input circuit to cause a secure user-identity captured message to be sent by the apparatus communication device to the central server confirming that a drug consumer's identity is stored in a drug storage apparatus memory to create an authorized drug consumer record for granting access permission;
   a device with a user interface for selecting an authenticated and unassigned drug storage apparatus and defining authorized drug monitoring entities and drug regimen parameters to establish a drug consumption regimen for a drug consumer by generating regimen encoded files with instructions for specific access periods for the authenticated drug storage apparatus;
   the central server having:
      a non-transitory memory storing a database of device-identity values for storage units for verifying the authentication request with the device-identity value for the storage unit one or more authenticated drug storage apparatus and generating confirmation messages for the verification of the authenticated drug storage apparatus;
      a server communication device that:
         receives the authentication request, the identity captured message and the drug access detection trigger signals from the apparatus communication device for identified access attempts;
         transmits the authentication confirmation messages for the verification of the authenticated drug storage apparatus;
         transmits the assignment confirmation message to provide the identification of an assigned drug consumer for identity capture;
         transmits the drug regimen encoded files securely to the apparatus communication device to provide the instructions for the specific access periods for the authenticated drug storage apparatus;
         transmits a commence dosing message to trigger the start of drug dosing operation when both the drug regimen encoded files are downloaded and when the identity captured message is received related to the authorized drug consumer assigned to the authenticated drug storage apparatus;
         receives the drug access detection trigger signals from the apparatus communication computer device for identified access attempts; and
      a hardware processor that relays drug consumption information and alarm messages onto the defined authorized drug monitoring entities.

2. The computer system of claim 1, further comprising a plurality of access detection computer circuits corresponding to a plurality of medication storage areas of the drug packaging, each of the medication storage areas having a corresponding access detection computer circuit.

3. The computer system of claim 2, wherein the system disables an access detection computer circuit for the corresponding medication storage area.

4. The computer system of claim 3, wherein a user action to access the medication storage area disables access detection computer circuit for the corresponding storage medication area.

5. The computer system of claim 1, wherein the central server having the hardware processor receives the drug access detection signals from the apparatus communication device and computes drug adherence and drug consumption metrics by processing the drug access detection trigger signals in relation to the drug regimen parameters for one or more authenticated drug storage apparatus.

6. The computer system of claim 1, wherein the central server having the hardware processor receives and processes activity messages from the authenticated drug storage apparatus with severity indicators that are used to select alarm messages.

7. The computer system of claim 1, further comprising a main access detection computer circuit having an overall unique identity, and a plurality of access detection computer circuits corresponding to a plurality of individual medication storage areas of the drug packaging.

8. The computer system of claim 1, wherein the authenticated drug storage apparatus has a lock to enable the storage unit in a closed locked position and the storage unit in an open unlocked position, wherein the control commands trigger the lock to enable the unlocked open position in response to an assignment confirmation message, the storage unit in the open unlocked position capable of containing the drug packaging, the lock further triggering to the closed locked position by detecting the drug packaging in the storage unit, the lock further resists and detects unauthorized access attempts using user-identity input.

9. The computer system of claim 1, wherein the authenticated drug storage apparatus has a device-identity known to the central server.

10. The computer system of claim 1, wherein the user interface further requires an authorized drug manager to enter a verification code of the authenticated storage apparatus before being allowed to assign the authenticated drug storage apparatus to a drug consumer.

11. The computer system of claim 1, wherein the drug regimen parameters are provided from an external system and exchanged with the central server.

12. The computer system of claim 1, wherein drug adherence and drug consumption information is further relayed onto external systems over a secure link for further analysis and presentation.

13. The computer system of claim 1, wherein the drug storage apparatus sends a message to trigger a secondary event; wherein the secondary event may be one or more of making an emergency call, and triggering a secondary drug storage apparatus to begin operation.

14. The computer system of claim 1, wherein the user interface receives input for a number of drugs for the drug packaging and the central servers sends the input.

15. The computer system of claim 1, wherein the access detection computer circuit further sends a secure communication message to the central server indicating a type and quantity of drugs for the drug packaging.

16. The computer system of claim 1, wherein the drug monitoring entities comprise a drug consumer computer.

17. The computer system of claim 1, further comprising a logging system that collects historical information from the drug monitoring entities to create statistical models around drug adherence by drug consumers.

18. The computer system of claim 8, wherein the lock of the storage unit can be triggered to the open unlocked position when the packaged drugs inside the storage unit are exhausted.

19. A method for detecting and tracking drug extraction from a plurality of drug storage apparatuses, the method comprising:
at one or more authenticated drug storage apparatuses, providing drug access detection trigger signals using an access detection computer circuit that integrates with drug packaging to create detectable drug packaging;
sending control commands using a hardware processor of a drug storage apparatus to trigger an assigned mode in response to an assignment confirmation message, the drug storage apparatus coupling to the detectable drug packaging, the assignment further detecting the presence of individual drug packaging compartments correlated to the detectable drug packaging;
transmitting, by a communication device, secure communication data messages, the access detection trigger signals, and an authentication request containing a device-identity value for the one or more authenticated drug storage apparatus for receiving one or more confirmation messages from a central server for verification of the authenticated drug storage apparatus and verification of assignment of the drug storage apparatus;
relaying, by the communication device, the one or more confirmation messages to the hardware processor;
sending a secure user-identity captured message by an identity input circuit and the communication device to the central server confirming that a drug consumer's identity is stored in a drug storage apparatus memory to create an authorized drug consumer record for confirming access to loaded drugs in a storage unit of the one or more authenticated drug storage apparatuses;
selecting an authenticated and unassigned drug storage apparatus and defining authorized drug monitoring entities and drug regimen parameters at a user interface of the central server to establish a drug consumption regimen for a drug consumer by generating regimen encoded files with instructions for specific access periods when drugs can be accessed from the authenticated drug storage apparatus;
storing a database of device-identity values for verifying the authentication request with the device-identity value for the one or more authenticated drug storage apparatus and generating confirmation messages for the verification of the authenticated drug storage apparatus;
receiving, at a communication interface, the authentication request, the identity captured message and the drug access detection trigger signals from the communication device for identified attempts to access the drugs within the storage unit of the one or more authenticated drug storage apparatuses;
transmitting the authentication confirmation messages for the verification of the authenticated drug storage apparatus;
transmitting the assignment confirmation message to trigger the assignment of the authenticated drug storage apparatus;
transmitting the drug regimen encoded files securely to the communication device to provide the instructions for the specific access periods when the packaged drugs should be accessed by an authorized drug consumer from the authenticated drug storage apparatus;
transmitting a commence dosing message to trigger the start of drug dosing operation when both the drug regimen encoded files are downloaded and when the identity captured message is received related to the authorized drug consumer assigned to the authenticated drug storage apparatus;
receiving the drug access detection trigger signals from the communication device for identified attempts to access the drugs within the storage unit of the one or more authenticated drug storage apparatuses;
computing, at a hardware processor, drug adherence and drug consumption data by processing the drug access detection trigger signals in relation to the drug regimen parameters for one or more authenticated drug storage apparatus;

receiving and processing activity messages from the authenticated drug storage apparatus with severity indicators that are used to select alarm messages; and relaying drug consumption data and alarm messages onto the defined authorized drug monitoring entities.

20. A system for detecting and tracking drug extractions at one or more drug storage apparatus, the system comprising:

a central server having a hardware processor and memory storing drug consumption data;

a drug storage apparatus having:
  a storage unit that couples to an access detection computer circuit that integrates with drug packaging containing one or more medication storage areas, the storage unit containing a device-identity known to the central server;

wherein central server authorizes the drug storage apparatus using the storage unit device-identity;

wherein the authorized drug storage apparatus communicates with the central server and exchanges authorization and configuration parameters;

a hardware processor having a user interface for defining drug regimen parameters to establish a drug consumption regimen for a drug consumer by generating non-transitory computer readable media storing regimen encoded files with instructions for specific access periods when drugs can be accessed from the authorized drug storage apparatus;

a communication interface for the drug storage apparatus and the central server, wherein the communication interface:
  transmits confirmation messages for the authorization of the drug storage apparatus;
  securely transmits the drug regimen encoded files to the authorized drug storage apparatus with instructions for the specific access periods when the drugs can be accessed by an authorized drug consumer from the authorized drug storage apparatus;
  transmits a commence dosing message to trigger the start of drug dosing operation when both the drug regimen encoded files are downloaded and when an identity captured message is received related to drugs held by the authorized drug storage apparatus;
  receives drug access detection trigger signals for identified attempts to access the drugs within the packaging; and
  wherein the hardware processor in the central server computes and updates the drug consumption data stored in the memory using the drug access detection trigger signals and the dosing regimen encoded files and relays drug consumption information onto the defined authorized drug monitoring entities.

* * * * *